US011932865B2

(12) United States Patent
Ostlie et al.

(10) Patent No.: US 11,932,865 B2
(45) **Date of Patent: *Mar. 19, 2024**

(54) ACETYL CO-ENZYME A CARBOXYLASE HERBICIDE RESISTANT PLANTS

(71) Applicant: COLORADO WHEAT RESEARCH FOUNDATION, INC., Fort Collins, CO (US)

(72) Inventors: Michael Hal Ostlie, Carrington, ND (US); Scott Haley, Fort Collins, CO (US); Philip Westra, Fort Collins, CO (US); Victoria Ashley Anderson, Fort Collins, CO (US)

(73) Assignee: COLORADO WHEAT RESEARCH FOUNDATION, INC., Fort Collins, CO (US)

( * ) Notice: Subject to any disclaimer, the term of this patent is extended or adjusted under 35 U.S.C. 154(b) by 67 days.

This patent is subject to a terminal disclaimer.

(21) Appl. No.: 17/446,776

(22) Filed: Sep. 2, 2021

(65) Prior Publication Data

US 2022/0002745 A1 Jan. 6, 2022

Related U.S. Application Data

(63) Continuation of application No. 16/453,359, filed on Jun. 26, 2019, now Pat. No. 11,130,962, which is a continuation of application No. 15/401,500, filed on Jan. 9, 2017, now Pat. No. 10,370,678, which is a continuation of application No. 13/981,373, filed as application No. PCT/US2012/023298 on Jan. 31, 2012, now Pat. No. 9,578,880.

(60) Provisional application No. 61/553,830, filed on Oct. 31, 2011, provisional application No. 61/438,294, filed on Feb. 1, 2011.

(51) Int. Cl.

| | |
|---|---|
| ***C12N 15/82*** | (2006.01) |
| ***A01H 5/10*** | (2018.01) |
| ***A01H 6/46*** | (2018.01) |
| ***A01N 43/54*** | (2006.01) |
| ***C12N 9/00*** | (2006.01) |
| ***C12Q 1/6895*** | (2018.01) |

(52) U.S. Cl.

CPC .......... *C12N 15/8274* (2013.01); *A01H 5/10* (2013.01); *A01H 6/4678* (2018.05); *A01N 43/54* (2013.01); *C12N 9/93* (2013.01); *C12N 15/8218* (2013.01); *C12Q 1/6895* (2013.01); *C12Y 604/01002* (2013.01); *C12Q 2600/13* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 5,559,220 A | 9/1996 | Roessier et al. | |
| 5,756,290 A | 5/1998 | Haselkorn et al. | |
| 6,222,099 B1 | 4/2001 | Gengenbach et al. | |
| 6,306,636 B1 | 10/2001 | Haselkorn et al. | |
| 6,414,222 B1 | 7/2002 | Gengenbach et al. | |
| 9,578,880 B2 | 2/2017 | Ostlie et al. | |
| 2004/0194172 A1 | 9/2004 | Edge, III et al. | |
| 2004/0216190 A1 | 10/2004 | Kovalic | |
| 2005/0009163 A1 | 1/2005 | Tong et al. | |
| 2006/0211087 A1 | 9/2006 | Roosild | |
| 2010/0081178 A1 | 4/2010 | Roberts | |
| 2010/0293628 A1* | 11/2010 | Tuinstra | C12N 15/8274 800/300 |

FOREIGN PATENT DOCUMENTS

| | | |
|---|---|---|
| WO | 2005123946 A1 | 12/2005 |
| WO | 2008089061 A2 | 7/2008 |
| WO | 2009155580 A1 | 12/2009 |
| WO | 2011028832 A2 | 3/2011 |
| WO | 2011028833 A2 | 3/2011 |
| WO | 2011028836 A3 | 3/2011 |

OTHER PUBLICATIONS

Song, Q. J., et al. "Development and mapping of microsatellite (SSR) markers in wheat." Theoretical and applied genetics 110.3 (2005): 550-560. (Year: 2005).*

Song et al., "Development and mapping of microsatellite (SSR) markers in wheat", Theoretical and applied genetics 110.3, pp. 550-560 2005.

EMBL Accession No. AM408430, http://www.ebi.ac.uk/Tools/dbfetch?style=html&id=AM408430 [retried from the Internet May 5, 2012], 8 pages May 5, 2012.

Colorado Wheat Research Foundation, Inc., PCT/US12/23298 filed Jan. 31, 2012, "The International Search Report and the Written Opinion of the International Searching Authority, or the Declaration", dated May 18, 2012. May 18, 2012.

Chalupska, D., et al. "Acc homoeoloci and the evolution of wheat genomes", PNAS, vol. 105, No. 28, pp. 9691-9696, Jul. 15, 2008.

Liu et al., "Single-site mutations in the carboxyltransferase domain of plastid acetyl-CoA carboxylase confer resistance to grass-specific herbicides", PNAS, vol. 104, No. 9, pp. 3627-3632, Feb. 27, 2007.

(Continued)

*Primary Examiner* — Weihua Fan

(74) *Attorney, Agent, or Firm* — McKee, Voorhees & Sease, PLC

(57) ABSTRACT

The present invention provides for compositions and methods for producing crop plants that are resistant to herbicides. In particular, the present invention provides for wheat plants, plant tissues and plant seeds that contain altered acetyl-CoA carboxylase (ACCase) genes and proteins that are resistant to inhibition by herbicides that normally inhibit the activity of the ACCase protein.

9 Claims, 11 Drawing Sheets

Specification includes a Sequence Listing.

(56) References Cited

OTHER PUBLICATIONS

Zagnitko, O., et al. "An isoleucine/leucine residue in the carboxyltransferase domain of acetyl-CoA carboxylase is critical for interaction with aryloxyphenoxypropionate and cyclohexanedione inhibitors", PNAS, vol. 98, No. 12, pp. 6617-6622, Jun. 5, 2001.

* cited by examiner

FIG. 3

Hatcher A genome (non-mutant) - SEQ ID NO:1

GTGTTGGATGGTCTGATGATGGCAGCCCTGAACGTGGGTTTCAGTACATTTATCTGACTGAAGAAGACCATGCT
CGTATTAGCACTTCTGTTATAGCGCACAAGATGCAGCTTGATAATGGTGAAATTAGGTGGGTTATTGATTCTGTT
GTGGGGAAGGAGGATGGGCTAGGTGTGGAGAACATACATGGAAGTGCTGCTATTGCCAGTGCCTATTCTAGGG
CCTATGAGGAGACATTTACGCTTACATTTGTGACTGGACGGACTGTTGGAATAGGAGCATATCTTGCTCGACTTG
GCATACGGTGCATACAGCGTACTGACCAGCCCATTATCCTAACCGGGTTCTCTGCTTTGAACAAGCTTCTTGGCC
GGGAAGTGTACAGCTCCCACATGCAGTTGGGTGGCCCCAAAATTATGGCGACAAACGGTGTTGTCCATCTGACA
GTTTCAGATGACCTTGAAGGTGTGTCTAATATATTGAGGTGGCTCAGCTATGTTCCTGCCAACATTGGTGGACCT
CTTCCTATTACAAAATCTTTGGACCCACCTGACAGACCCGTTGCATATATCCCTGAGAATACATGTGATCCTCGTG
CAGCCATCAGTGGCATTGATGATAGCCAAGGGAAATGGTTGGGGGGCATGTTCGACAAAGACAGTTTTGTGGA
GACATTTGAAGGATGGGCGAAGTCAGTAGTTACTGGCAGAGCGAAACTCGGAGGGATTCCGGTGGGTGTTATA
GCTGTGGAGACACAGACTATGATGCAGCTCATCCCTGCTGATCCAGGCCAGCTTGATTCCCATGAGCGGTCTGTT
CCTCGTGCTGGGCAAGTCTGGTTTCCAGATTCAGCTACTAAGACAGCTCAAGCAATGCTGGACTTCAACCGTGAA
GGATTACCTCTGTTCATCCTTGCTAACTGGAGAGGCTTCTCTGGTGGGCAAAGAGATCTTTTTGAAGGAATCCTT
CAGGCTGGGTCAACAATTGTTGAGAACCTTAGGACATACAATCAGCCTGCCTTTGTATATATCCCCAAGGCTGCA
GAGCTACGTGGAGGGGCTTGGGTCGTGATTGATAGCAAGATAAATCCAGATCGAATTGAGTTCTATGCTGAGA
GGACTGCAAAGGG

Protein - SEQ ID NO:7

VGWSDDGSPERGFQYIYLTEEDHARISTSVIAHKMQLDNGEIRWVIDSVVGKEDGLGVENIHGSAAIASAYSRAYEE
TFTLTFVTGRTVGIGAYLARLGIRCIQRTDQPIILTGFSALNKLLGREVYSSHMQLGGPKIMATNGVVHLTVSDDLEGV
SNILRWLSYVPANIGGPLPITKSLDPPDRPVAYIPENTCDPRAAISGIDDSQGKWLGGMFDKDSFVETFEGWAKSVV
TGRAKLGGIPVGVIAVETQTMMQLIPADPGQLDSHERSVPRAGQVWFPDSATKTAQAMLDFNREGLPLFILANWR
GFSGGQRDLFEGILQAGSTIVENLRTYNQPAFVYIPKAAELRGGAWVVIDSKINPDRIEFYAERTAK

FIG. 4A

Mutant A genome sequence (consensus) - SEQ ID NO:4

GATGAAGTAAAATCGTGCTTC-
GTGTTGGATGGTCTGATGATGGCAGCCCTGAACGTGGGTTTCAGTACATTTATCTGACTGAAGAAGACCATGCT
CGTATTAGCACTTCTGTTATAGCGCACAAGATGCAGCTTGATAATGGTGAAATTAGGTGGGTTATTGATTCTGTT
GTGGGGAAGGAGGATGGGCTAGGTGTGGAGAACATACATGGAAGTGCTGCTATTGCCAGTGCCTATTCTAGGG
CCTATGAGGAGACATTTACGCTTACATTTGTGACTGGACGGACTGTTGGAATAGGAGCATATCTTGCTCGACTTG
GCATACGGTGCATACAGCGTACTGACCAGCCCATTATCCTAACCGGGTTCTCTGCTTTGAACAAGCTTCTTGGCC
GGGAAGTGTACAGCTCCCACATGCAGTTGGGTGGCCCCAAAATTATGGCGACAAACGGTGTTGTCCATCTGACA
GTTTCAGATGACCTTGAAGGTGTGTCTAATATATTGAGGTGGCTCAGCTATGTTCCTGCCAACATTGGTGGACCT
CTTCCTATTACAAAATCTTTGGACCCACCTGACAGACCCGTTGCATATATCCCTGAGAATACATGTGATCCTCGTG
CAGCCATCAGTGGCATTGATGATAGCCAAGGGAAATGGTTGGGGGGCATGTTCGACAAAGACAGTTTTGTGGA
GACATTTGAAGGATGGGCGAAGTCAGTAGTTACTGGCAGAGCGAAACTCGGAGGGATTCCGGTGGGTGTTATA
GCTGTGGAGACACAGACTATGATGCAGCTCATCCCTGCTGATCCAGGCCAGCTTGATTCCCATGAGCGGTCTGTT
CCTCGTGCTGGGCAAGTCTGGTTTCCAGATTCAGTTACTAAGACAGCTCAAGCAATGCTGGACTTCAACCGTGAA
GGATTACCTCTGTTCATCCTTGCTAACTGGAGAGGCTTCTCTGGTGGGCAAAGAGATCTTTTTGAAGGAATCCTT
CAGGCTGGGTCAACAATTGTTGAGAACCTTAGGACATACAATCAGCCTGCCTTTGTATATATCCCCAAGGCTGCA
GAGCTACGTGGAGGGGCTTGGGTCGTGATTGATAGCAAGATAAATCCAGATCGAATTGAGTTCTATGCTGAGA
GGACTGCAAAGGGTAATGTTCTTGAACCTCAAGGGTTGATTGAGATACCAG

Protein - SEQ ID NO:8

*SKIVLRVGWSDDGSPERGFQYIYLTEEDHARISTSVIAHKMQLDNGEIRWVIDSVVGKEDGLGVENIHGSAAIASAY
SRAYEETFTLTFVTGRTVGIGAYLARLGIRCIQRTDQPIILTGFSALNKLLGREVYSSHMQLGGPKIMATNGVVHLTVS
DDLEGVSNILRWLSYVPANIGGPLPITKSLDPPDRPVAYIPENTCDPRAAISGIDDSQGKWLGGMFDKDSFVETFEG
WAKSVVTGRAKLGGIPVGVIAVETQTMMQLIPADPGQLDSHERSVPRAGQVWFPDSVTKTAQAMLDFNREGLPL
FILANWRGFSGGQRDLFEGILQAGSTIVENLRTYNQPAFVYIPKAAELRGGAWVVIDSKINPDRIEFYAERTAKGNVL
EPQGLIEIP

FIG. 4B

Hatcher B genome (non-mutant) - SEQ ID NO:2

CGTGTTGGATGGTCTGATGATGGCAGCCCTGAACGTGGGTTTCAGTACATTTATCTGACTGAAGAAGACCATGC
TCGTATTAGCACTTCTGTTATAGCGCACAAGATGCAGCTTGATAATGGTGAAATTAGGTGGGTTATCGATTCTGT
TGTGGGGAAGGAGGATGGGCTAGGTGTGGAGAACATACATGGAAGTGCTGCTATTGCCAGTGCCTATTCTAGG
GCCTATGAGGAGACATTTACGCTTACATTTGTGACTGGACGGACTGTTGGAATAGGAGCATATCTTGCTCGACTT
GGCATACGGTGCATACAGCGTACTGACCAGCCCATTATCCTAACTGGGTTCTCTGCCTTGAACAAGCTTCTTGGC
CGGGAAGTTTACAGCTCCCACATGCAGTTGGGTGGCCCCAAAATTATGGCGACAAACGGTGTTGTCCATCTGAC
AGTTTCAGATGACCTTGAAGGTGTATCTAATATATTGAGGTGGCTCAGCTATGTTCCTGCCAACATTGGTGGACC
TCTTCCTATTACAAAATCTTTGGACCCACCTGACAGACCCGTTGCTTACATCCCTGAGAATACATGCGATCCTCGT
GCTGCCATCAGTGGCATTGATGATAGCCAAGGGAAATGGTTGGGGGGCATGTTCGACAAAGACAGTTTTGTGG
AGACATTTGAAGGATGGGCGAAGTCAGTTGTTACTGGCAGAGCTAAACTCGGAGGGATTCCGGTGGGTGTTAT
AGCTGTGGAGACACAGACTATGATGCAGCTCATCCCTGCTGATCCAGGCCAGCTTGATTCCCATGAGCGGTCTGT
TCCTCGTGCTGGGCAAGTCTGGTTTCCAGATTCAGCTACTAAGACAGCGCAGGCAATGCTGGACTTCAACCGTGA
AGGATTACCTCTGTTCATCCTTGCTAACTGGAGAGGCTTCTCTGGTGGACAAAGAGATCTTTTTGAAGGAATCCT
TCAGGCTGGGTCAACAATTGTTGAGAACCTTAGGACATACAATCAGCCTGCCTTTGTATATATCCCCAAGGCTGC
AGAGCTACGTGGAGGGGCTTGGGTCGTGATTGATAGCAAGATAAATCCAGATCGCATTGAGTTCTATGCTGAG
AGGACTGCAAAGGGCAATGTTCTCGAACCTCAAGGG

Protein - SEQ ID NO:9

RVGWSDDGSPERGFQYIYLTEEDHARISTSVIAHKMQLDNGEIRWVIDSVVGKEDGLGVENIHGSAAIASAYSRAYE
ETFTLTFVTGRTVGIGAYLARLGIRCIQRTDQPIILTGFSALNKLLGREVYSSHMQLGGPKIMATNGVVHLTVSDDLEG
VSNILRWLSYVPANIGGPLPITKSLDPPDRPVAYIPENTCDPRAAISGIDDSQGKWLGGMFDKDSFVETFEGWAKSV
VTGRAKLGGIPVGVIAVETQTMMQLIPADPGQLDSHERSVPRAGQVWFPDSATKTAQAMLDFNREGLPLFILANW
RGFSGGQRDLFEGILQAGSTIVENLRTYNQPAFVYIPKAAELRGGAWVVIDSKINPDRIEFYAERTAKGNVLEPQG

FIG. 4C

Mutant B genome sequence (consensus) - SEQ ID NO:5

GGCATAGCAGATGAAGTAGAGTCTTGCTTCCGTGTTGGATGGTCTGATGATGGCAGCCCTGAACGTGGGTTTCA
GTACATTTATCTGACTGAAGAAGACCATGCTCGTATTAGCACTTCTGTTATAGCGCACAAGATGCAGCTTGATAA
TGGTGAAATTAGGTGGGTTATCGATTCTGTTGTGGGGAAGGAGGATGGGCTAGGTGTGGAGAACATACATGG
AAGTGCTGCTATTGCCAGTGCCTATTCTAGGGCCTATGAGGAGACATTTACGCTTACATTTGTGACTGGACGGAC
TGTTGGAATAGGAGCATATCTTGCTCGACTTGGCATACGGTGCATACAGCGTACTGACCAGCCCATTATCCTAAC
TGGGTTCTCTGCCTTGAACAAGCTTCTTGGCCGGGAAGTTTACAGCTCCCACATGCAGTTGGGTGGCCCCAAAAT
TATGGCGACAAACGGTGTTGTCCATCTGACAGTTTCAGATGACCTTGAAGGTGTATCTAATATATTGAGGTGGCT
CAGCTATGTTCCTGCCAACATTGGTGGACCTCTTCCTATTACAAAATCTTTGGACCCACCTGACAGACCCGTTGCT
TACATCCCTGAGAATACATGCGATCCTCGTGCTGCCATCAGTGGCATTGATGATAGCCAAGGGAAATGGTTGGG
GGGCATGTTCGACAAAGACAGTTTTGTGGAGACATTTGAAGGATGGGCGAAGTCAGTTGTTACTGGCAGAGCT
AAACTCGGAGGGATTCCGGTGGGTGTTATAGCTGTGGAGACACAGACTATGATGCAGCTCATCCCTGCTGATCC
AGGCCAGCTTGATTCCCATGAGCGGTCTGTTCCTCGTGCTGGGCAAGTCTGGTTTCCAGATTCAGTTACTAAGAC
AGCGCAGGCAATGCTGGACTTCAACCGTGAAGGATTACCTCTGTTCATCCTTGCTAACTGGAGAGGCTTCTCTGG
TGGACAAAGAGATCTTTTTGAAGGAATCCTTCAGGCTGGGTCAACAATTGTTGAGAACCTTAGGACATACAATC
AGCCTGCCTTTGTATATATCCCCAAGGCTGCAGAGCTACGTGGAGGGGCTTGGGTCGTGATTGATAGCAAGATA
AATCCAGATCGCATTGAGTTCTATGCTGAGAGGACTGCAAAGGGCAATGTTCTCGAACCTCAAGGGTTGATTGA
GATG

Protein - SEQ ID NO:10

GIADEVESCFRVGWSDDGSPERGFQYIYLTEEDHARISTSVIAHKMQLDNGEIRWVIDSVVGKEDGLGVENIHGSAA
IASAYSRAYEETFTLTFVTGRTVGIGAYLARLGIRCIQRTDQPIILTGFSALNKLLGREVYSSHMQLGGPKIMATNGVVH
LTVSDDLEGVSNILRWLSYVPANIGGPLPITKSLDPPDRPVAYIPENTCDPRAAISGIDDSQGKWLGGMFDKDSFVET
FEGWAKSVVTGRAKLGGIPVGVIAVETQTMMQLIPADPGQLDSHERSVPRAGQVWFPDSVTKTAQAMLDFNREG
LPLFILANWRGFSGGQRDLFEGILQAGSTIVENLRTYNQPAFVYIPKAAELRGGAWVVIDSKINPDRIEFYAERTAKGN
VLEPQGLIEM

FIG. 4D

Hatcher D genome (non-mutant) - SEQ ID NO:3

ATCTTGCTTCCGTGTTGGATGGTCTGATGATGGCAGCCCTGAACGTGGGTTTCAATATATTTATCTGACTGAAGA
AGACCATGCTCGTATTAGCGCTTCTGTTATAGCGCACAAGATGCAGCTTGATAATGGTGAAATTAGGTGGGTTA
TTGATTCTGTTGTAGGGAAGGAGGATGGGCTAGGTGTGGAGAACATACATGGAAGTGCTGCTATTGCCAGTGC
CTATTCTAGGGCCTATGAGGAGACATTTACGCTTACATTTGTGACTGGAAGGACTGTTGGAATAGGAGCATATC
TTGCTCGACTTGGCATACGGTGCATTCAGCGTACTGACCAGCCCATTATCCTAACTGGGTTTTCTGCCTTGAACAA
GCTTCTTGGCCGGGAAGTGTACAGCTCCCACATGCAGTTGGGTGGCCCCAAAATTATGGCCACAAACGGTGTTG
TCCATCTGACAGTTTCAGATGACCTTGAAGGTGTATCTAATATATTGAGGTGGCTCAGCTATGTTCCTGCCAACA
TTGGTGGACCTCTTCCTATTACAAAATCTTTGGACCCACCTGACAGACCCGTTGCTTACATCCCTGAGAATACATG
TGATCCTCGTGCAGCCATCAGTGGCATTGATGATAGCCAAGGGAAATGGTTGGGGGGCATGTTCGACAAAGAC
AGTTTTGTGGAGACATTTGAAGGATGGGCGAAGTCAGTAGTTACTGGCAGAGCGAAACTCGGAGGGATTCCGG
TGGGTGTTATAGCTGTGGAGACACAGACTATGATGCAGCTCATCCCTGCTGATCCAGGTCAGCTTGATTCCCATG
AGCGGTCTGTTCCTCGTGCTGGGCAAGTCTGGTTTCCAGATTCAGCTACTAAGACAGCGCAGGCAATGCTGGAC
TTCAACCGTGAAGGATTACCTCTGTTCATCCTTGCTAACTGGAGAGGCTTCTCTGGTGGGCAAAGAGATCTTTTT
GAAGGAATCCTTCAGGCTGGGTCAACAATTGTTGAGAACCTTAGGACATACAATCAGCCTGCCTTTGTATATATC
CCCAAGGCTGCAGAGCTACGTGGAGGGGCTTGGGTCGTGATTGATAGCAAGATAAATCCAGATCGCATTGAGT
TCTATGCTGAGAGGACTGCAAAGGGCAATGTTCT-GAACCTCAAGGG

Protein - SEQ ID NO:11

SCFRVGWSDDGSPERGFQYIYLTEEDHARISASVIAHKMQLDNGEIRWVIDSVVGKEDGLGVENIHGSAAIASAYSR
AYEETFTLTFVTGRTVGIGAYLARLGIRCIQRTDQPIILTGFSALNKLLGREVYSSHMQLGGPKIMATNGVVHLTVSDD
LEGVSNILRWLSYVPANIGGPLPITKSLDPPDRPVAYIPENTCDPRAAISGIDDSQGKWLGGMFDKDSFVETFEGWA
KSVVTGRAKLGGIPVGVIAVETQTMMQLIPADPGQLDSHERSVPRAGQVWFPDSATKTAQAMLDFNREGLPLFILA
NWRGFSGGQRDLFEGILQAGSTIVENLRTYNQPAFVYIPKAAELRGGAWVVIDSKINPDRIEFYAERTAKGNVLNLK

FIG. 4E

Mutant D genome sequence (consensus) - SEQ ID NO:6

**TGAAGTAAAATCTTGCTTCCGTGTTGGATGGTCTGATGATGGCAGCCCTGAACGTGGGTTTCAATATATTTATCT
GACTGAAGAAGACCATGCTCGTATTAGCGCTTCTGTTATAGCGCACAAGATGCAGCTTGATAATGGTGAAATTA
GGTGGGTTATTGATTCTGTTGTAGGGAAGGAGGATGGGCTAGGTGTGGAGAACATACATGGAAGTGCTGCTAT
TGCCAGTGCCTATTCTAGGGCCTATGAGGAGACATTTACGCTTACATTTGTGACTGGAAGGACTGTTGGAATAG
GAGCATATCTTGCTCGACTTGGCATACGGTGCATTCAGCGTACTGACCAGCCCATTATCCTAACTGGGTTTTCTGC
CTTGAACAAGCTTCTTGGCCGGGAAGTGTACAGCTCCCACATGCAGTTGGGTGGCCCCAAAATTATGGCCACAA
ACGGTGTTGTCCATCTGACAGTTTCAGATGACCTTGAAGGTGTATCTAATATATTGAGGTGGCTCAGCTATGTTC
CTGCCAACATTGGTGGACCTCTTCCTATTACAAAATCTTTGGACCCACCTGACAGACCCGTTGCTTACATCCCTGA
GAATACATGTGATCCTCGTGCAGCCATCAGTGGCATTGATGATAGCCAAGGGAAATGGTTGGGGGGCATGTTC
GACAAAGACAGTTTTGTGGAGACATTTGAAGGATGGGCGAAGTCAGTAGTTACTGGCAGAGCGAAACTCGGA
GGGATTCCGGTGGGTGTTATAGCTGTGGAGACACAGACTATGATGCAGCTCATCCCTGCTGATCCAGGTCAGCT
TGATTCCCATGAGCGGTCTGTTCCTCGTGCTGGGCAAGTCTGGTTTCCAGATTCAGTTACTAAGACAGCGCAGGC
AATGCTGGACTTCAACCGTGAAGGATTACCTCTGTTCATCCTTGCTAACTGGAGAGGCTTCTCTGGTGGGCAAAG
AGATCTTTTTGAAGGAATCCTTCAGGCTGGGTCAACAATTGTTGAGAACCTTAGGACATACAATCAGCCTGCCTT
TGTATATATCCCCAAGGCTGCAGAGCTACGTGGAGGGGCTTGGGTCGTGATTGATAGCAAGATAAATCCAGATC
GCATTGAGTTCTATGCTGAGAGGACTGCAAAGGGCAATGTTCTTGAACCTCAAGGGTTGATTGAGATGC**

Protein - SEQ ID NO:12

EVKSCFRVGWSDDGSPERGFQYIYLTEEDHARISASVIAHKMQLDNGEIRWVIDSVVGKEDGLGVENIHGSAAIASAYS
RAYEETFTLTFVTGRTVGIGAYLARLGIRCIQRTDQPIILTGFSALNKLLGREVYSSHMQLGGPKIMATNGVVHLTVSDDL
EGVSNILRWLSYVPANIGGPLPITKSLDPPDRPVAYIPENTCDPRAAISGIDDSQGKWLGGMFDKDSFVETFEGWAKSV
VTGRAKLGGIPVGVIAVETQTMMQLIPADPGQLDSHERSVPRAGQVWFPDSVTKTAQAMLDFNREGLPLFILANWR
GFSGGQRDLFEGILQAGSTIVENLRTYNQPAFVYIPKAAELRGGAWVVIDSKINPDRIEFYAERTAKGNVLEPQGLIEM

*FIG. 4F*

| | |
|---|---|
| Hatcher A genome<br>SEQ ID NO:1 | GGTTTCCAGATTCAG[illegible]TACTAAGACAGC[illegible]CA[illegible]GCAATGCTGG |
| Mutant A genome<br>SEQ ID NO:4 | GGTTTCCAGATTCAG[illegible]TACTAAGACAGC[illegible]CA[illegible]GCAATGCTGG |
| Hatcher B genome<br>SEQ ID NO:2 | GGTTTCCAGATTCAG[illegible]TACTAAGACAGCGCAGGCAATGCTGG |
| Mutant B genome<br>SEQ ID NO:5 | GGTTTCCAGATTCAG[illegible]TACTAAGACAGCGCAGGCAATGCTGG |
| Hatcher D genome<br>SEQ ID NO:3 | GGTTTCCAGATTCAG[illegible]TACTAAGACAGCGCAGGCAATGCTGG |
| Mutant D genome<br>SEQ ID NO:6 | GGTTTCCAGATTCAG[illegible]TACTAAGACAGCGCAGGCAATGCTGG |

*FIG. 7*

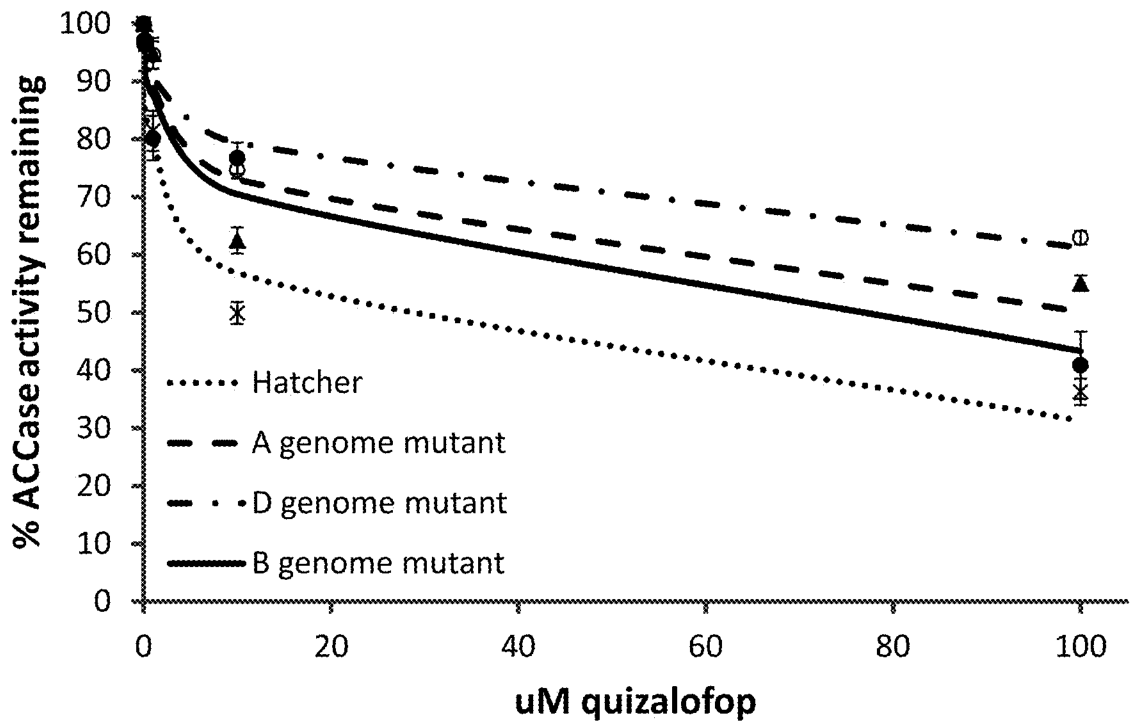

*FIG. 8*

ACETYL CO-ENZYME A CARBOXYLASE HERBICIDE RESISTANT PLANTS

CROSS REFERENCE TO RELATED APPLICATION

This application is a Continuation Application of Ser. No. 16/453,359, filed Jun. 26, 2019, which is a continuation of U.S. Ser. No. 15/401,500, filed Jan. 9, 2017, now U.S. Pat. No. 10,370,678, issued Aug. 6, 2019, which is a continuation of U.S. Ser. No. 13/981,373, filed Sep. 24, 2013, now U.S. Pat. No. 9,578,880, issued Feb. 28, 2017, which is a National Phase application of PCT/US12/23298 filed Jan. 31, 2012 which claims priority under 35 U.S.C. § 119 to U.S. Provisional Application Nos. 61/553,830 filed Oct. 31, 2011, and 61/438,294 filed Feb. 1, 2011, all of which are hereby incorporated herein by reference in their entirety.

FIELD OF THE INVENTION

The present invention provides for compositions and methods for producing crop plants that are resistant to herbicides. In particular, the present invention provides for wheat plants, plant tissues and plant seeds that contain modified acetyl-CoA carboxylase (ACCase) genes and proteins and are resistant to inhibition by herbicides that normally inhibit the activity of the ACCase protein.

BACKGROUND OF THE INVENTION

Wheat is grown worldwide and is the most widely adapted cereal. Common wheats are used in a variety of food products such as bread, cookies, cakes, crackers, and noodles. In general the hard wheat classes are milled into flour used for breads and the soft wheat classes are milled into flour used for pastries and crackers. Wheat starch is used in the food and paper industries, as laundry starches, and in other products.

The primary threat to commercial wheat production is weed competition, resulting in decreased grain yields and inferior grain quality. Although cultivation can be used to eliminate weeds, soil from tilled fields is highly vulnerable to wind and water erosion. Due to ease of application and effectiveness, herbicide treatment is the preferred method of weed control. Herbicides also permit weed control in reduced tillage or direct seeded cropping systems designed to leave high levels of residue on the soil surface to prevent erosion. The most significant weed competition in wheat comes from highly related grasses, such as wild oat and jointed goatgrass, and it is difficult to devise effective chemical control strategies for problematic weed species related to the cultivated crop since they tend to share herbicide sensitivities. One approach to solving this problem involves the development of herbicide resistant varieties. In this system, herbicide-is applied “in-crop” to control weeds without injuring the herbicide-tolerant crop plants.

The development of herbicide resistance in plants offers significant production and economic advantages; as such the use of herbicides for controlling weeds or plants in crops has become almost a universal practice. However, application of such herbicides can also result in death or reduced growth of the desired crop plant, making the time and method of herbicide application critical or in some cases unfeasible.

Of particular interest to farmers is the use of herbicides with greater potency, broad weed spectrum effectiveness and rapid soil degradation. Plants, plant tissues and seeds with resistance to these compounds would provide an attractive solution by allowing the herbicides to be used to control weed growth, without risk of damage to the crop. One such class of broad spectrum herbicides are those compounds that inhibit the activity of the acetyl-CoA carboxylase (ACCase) enzyme in a plant. Such herbicides are included in the aryloxyphenoxypropionate (FOP) and cyclohexanedione (DIM) chemical families. For example, wheat is susceptible to many ACCase inhibiting herbicides that target monocot species, making the use of these herbicides to control grassy weeds almost impossible.

Due to the importance of wheat as a crop plant on the world stage, there is a need for wheat hybrids that are resistant to the inhibitory effects of ACCase herbicides, thereby allowing for greater crop yield when these herbicides are used to control grassy weeds.

SUMMARY OF THE INVENTION

The present invention provides for compositions and methods for producing wheat plants that are resistant to herbicides. In particular, the present invention provides for wheat plants, varieties, lines, and hybrids, as well as plant tissues and plant seeds that contain altered acetyl-CoA carboxylase (ACCase) genes and proteins that are resistant to inhibition by herbicides that normally inhibit the activity of the ACCase protein.

Cultivated wheat is susceptible to many ACCase inhibiting herbicides that target monocot or grassy weed species. However, as described herein a wheat genotype was created that exhibits tolerance to ACCase inhibiting herbicides. Genetic analysis has identified genetic differences within a mutant wheat germplasm that results in an ACCase herbicide resistance phenotype.

In one embodiment, the present invention provides for one or more wheat plants whose germplasm comprises a mutation that renders the plant tolerant to ACCase herbicides. Moreover, in further embodiments the invention relates to the offspring (e.g., F1, F2, F3, etc.) of a cross of said plant wherein the germplasm of said offspring has the same mutation as the parent plant. Therefore, embodiments of the present invention provide for wheat varieties/hybrids whose germplasm contains a mutation, such that the phenotype of the plants is ACCase herbicide resistant. In some embodiments, said offspring (e.g., F1, F2, F3, etc.) are the result of a cross between elite wheat lines, at least one of which contains a germplasm comprising a mutation that renders the plant tolerant to ACCase herbicides.

In one embodiment, the present invention provides a wheat plant wherein said wheat plant germplasm confers resistance to inhibition by one or more acetyl-CoA carboxylase herbicides at levels of said one or more herbicides that would normally inhibit the growth of a wheat plant. In some embodiments, said one or more acetyl-CoA carboxylase herbicides are from aryloxyphenoxypropionate (FOP) and cyclohexanedione (DIM) chemical families. In some embodiments, said wheat plant germplasm that confers resistance to inhibition by one or more acetyl-CoA carboxylase herbicides comprises one or more mutations in the acetyl-CoA carboxylase gene as found in AF28-A, AF26-B and/or AF10-D, (ATCC Nos. P In another embodiment, the present invention provides a method of controlling weeds in the vicinity of a wheat plant or population of plants, comprising providing one or more acetyl-CoA carboxylase herbicides, applying said one or more acetyl-CoA carboxylase herbicides to a field comprising a wheat plant or population of wheat plants, and controlling weeds in the vicinity of said wheat plant or population of wheat plants such that weed growth is adversely affected by the application of said one or more herbicides and growth of said wheat plant or population thereof is not adversely affected. In some embodiments, said one or more acetyl-CoA carboxylase herbicides are from aryloxyphenoxypropionate (FOP) and cyclohexanedione (DIM) chemical families. In some embodiments, said wheat plant or populations of wheat plants comprise one or more mutations in the acetyl-CoA carboxylase gene as found in AF28-A, AF26-B and/or AF10-D, (ATCC Nos. PTA-123074, PTA-123076 and PTA-123075).

In another embodiment, the present invention provides a wheat hybrid, line or variety, wherein said wheat hybrid, line or variety comprises germplasm comprising one or more mutations in the acetyl-CoA carboxylase gene such that resistance to one or more acetyl-CoA carboxylase herbicides is conferred to said hybrid, line or variety. In some embodiments, said wheat hybrid, line or variety is created by introgression of a wheat germplasm that comprises said one or more mutations for conferring resistance to one or more acetyl-CoA carboxylase herbicides. In some embodiments, said wheat hybrid, line or variety is created by incorporation of a heterologous gene comprising one or more mutations for conferring resistance to one or more acetyl-CoA carboxylase herbicides.

In another embodiment, the present invention provides a method for producing a wheat hybrid, line or variety resistant to one or more acetyl-CoA carboxylase herbicides comprising identifying a germplasm conferring said herbicide resistance, wherein said herbicide resistant germplasm derives from an herbicide resistant wheat plant, and introducing said germplasm into an elite wheat plant hybrid, line or variety. In some embodiments, said introducing of said germplasm into said elite wheat plant hybrid, line or variety is by introgression. In some embodiments, said introducing of said germplasm into said elite wheat plant hybrid, line or variety is by introduction of a heterologous gene.

In yet another embodiment, the present invention provides a wheat hybrid, line or variety wherein the germplasm of said hybrid, line or variety comprises conferred resistance to one or more acetyl-CoA carboxylase herbicides and resistance to one or more compounds from one or more herbicide groups that are not acetyl-CoA carboxylase inhibitors.

In yet another embodiment, the present invention provides a method for identifying wheat plant lines resistant to acetyl-CoA carboxylase herbicides comprising supplying a nucleic acid sample from a wheat plant, providing amplification primers for amplifying a region of a wheat plant's genome corresponding to an acetyl-CoA carboxylase gene present in said nucleic acid sample, applying said amplification primers to said nucleic acid sample such that amplification of said region of said acetyl-CoA carboxylase gene occurs, and identifying wheat plants resistant to acetyl-CoA carboxylase herbicides based on the presence of one or more mutations that confer acetyl-CoA carboxylase herbicide resistance present in said amplified nucleic acid sample.

In still another embodiment, the present invention provides for wheat seeds wherein said germplasm of said seeds comprises a mutant acetyl-CoA carboxylase gene such that said mutation confers resistance to inhibition by acetyl-CoA carboxylase herbicides. In some embodiments, the germplasm of said wheat seeds comprise a mutant acetyl-CoA carboxylase gene as found in AF28-A, AF26-B and/or AF10-D, (ATCC Nos. PTA-123074, PTA-123076 and PTA-123075). In some embodiments, the present invention provides for wheat plants grown from said seeds and further plant parts that comprise said wheat plants grown from said seeds. In some embodiments, the mutant acetyl-CoA carboxylase gene is a functional fragment of the gene as found in AF28-A, AF26-B and/or AF10-D, (ATCC Nos. PTA-123074, PTA-123076 and PTA-123075), such that the gene fragment encodes a protein fragment that is sufficient to confer resistance to inhibition by acetyl-CoA carboxylase herbicides to a wheat plant. In some embodiments, the present invention provides for wheat plants that grow from said seeds and further plant parts that comprise said wheat plants grown from said seeds.

In some embodiments, the present invention provides purified and isolated nucleic acid sequences from wheat which encode acetyl-CoA carboxylase. According to the invention, wild-type sequences encoding acetyl-CoA carboxylase have been identified from the B, D, and A genome, (SEQ ID NOS: 1, 2, and 3, respectively). Further, mutations each genome have been identified which provide resistance to acetyl-CoA carboxylase herbicide, SEQ ID NOS: 4, 5, and 6, respectively. The mutation represents a change from Ala to Val at amino acid position 2004 (as referenced by standard black grass references gi|199600899|emb|AM408429.1| and gi|199600901|emb|AM408430.1Sequence ID NOS:13, 14 15 and 16, see also FIG. 9) for the each genome, A genome, (SEQ ID NO: 8); B genome, (SEQ ID NO: 10), D genome, (SEQ ID NO: 12). The invention also includes amino acids encoded by these sequences, including SEQ ID NO: 7, 8, 9, 10, 11 or 12, as well as conservatively modified variants, and fragments which retain ACCase activity as well as the mutants which provide resistance to acetyl-CoA carboxylase herbicide.

Thus compositions of the invention include an isolated polypeptide comprising an amino acid sequence selected from the group consisting of: (a) the amino acid sequence comprising SEQ ID NO:7, 9 or 11 and SEQ ID NOS 8, 10, or 12 and (b) the amino acid sequence comprising at least 90%, 95% or 99% sequence identity to SEQ ID NO:7, 9, 11 or SEQ ID NOS: 8, 10, or 12 wherein said polypeptide has ACCase activity or provides resistance to acetyl-CoA carboxylase herbicide.

The invention also includes a wheat plant that comprises a heterologous nucleotide sequence that is at least 70% homologous, at least 80% homologous, at least 85% homologous, at least 90% homologous, at least 95% homologous, at least 97% homologous, or at least 99% homologous to the acetyl-CoA carboxylase sequence of SEQ ID NO:1, 2, 3, 4, 5, or 6 or as found in AF28-A, AF26-B, and/or AF10-D (ATCC Nos. PTA-123074, PTA-123076 and PTA-123075). In some embodiments, the acetyl-CoA carboxylase sequence encodes or comprises one or more amino acid substitutions, for example Ala2004Val as found in SEQ ID NO: 8, as found in SEQ ID NO:10 or as found in SEQ ID NO:12.

In one embodiment, the present invention further provides for wheat hybrid plants that have all the physiological and morphological characteristics of said wheat plant grown from said wheat seed. In further embodiments, the present invention provides for tissue cultures and regenerated tissue cultures that arise from said wheat seed or said wheat plant part that comprises a mutation in said acetyl-CoA carboxylase gene as found in AF28-A, AF26-B and/or AF10-D, (ATCC Nos. PTA-123074, PTA-123076 and PTA-123075).

In one embodiment, the present invention provides a method of producing wheat seed comprising crossing a plant comprising a mutant acetyl-CoA carboxylase gene as found in AF28-A, AF26-B and/or AF10-D, (ATCC Nos. PTA- 123074, PTA-123076 and PTA-123075) with itself or a second wheat plant and collecting said seed from said cross. In some embodiments, the methods for producing said wheat seed comprises planting a parent seed wheat line wherein said parent seed line comprises a germplasm that confers resistance to acetyl-CoA carboxylase herbicides with a parent pollinator wheat line wherein said pollinator and/or seed line germplasm comprises a germplasm that confers resistance to acetyl-CoA carboxylase herbicides, growing said parent seed and pollinator wheat plants together, allowing for the said parent seed plants to be pollinated by said parent pollinator plants, and harvesting the seed that results from said pollination.

In yet another embodiment, the invention provides for genetically modified wheat plants incorporating a heterologous nucleotide construct including SEQ ID NOS: 1, 2, 3, 4, 5, or 6 operably linked to regulatory sequences such as expression cassettes, inhibition constructs, plants, plant cells, and seeds. The genetically modified plants, plant cells, and seeds of the invention may exhibit phenotypic changes, such as modulated ACCase or mutant ACCase levels.

Methods are provided for reducing or eliminating the activity of an ACCase polypeptide in a plant, comprising introducing into the plant a selected polynucleotide. In specific methods, providing the polynucleotide decreases the level of ACCase in the plant.

Methods are also provided for increasing the level of a mutant ACCase polypeptide in a plant either constitutively or at specifically regulated times and tissues comprising introducing into the plant a selected polynucleotide with appropriate regulatory elements. In specific methods, expression of the mutant ACCase polynucleotide improves the plant's tolerance to ACCase herbicides.

DESCRIPTION OF THE FIGURES

FIG. 3 is a photograph of a dose response study exhibiting the increased tolerance of selected mutant plants to quizalofop herbicide in the M3 generation compared to non-mutagenized Hatcher winter wheat. Column 1, 3, and 4 are plants selected for increased herbicide tolerance; column 2 is non-mutagenized Hatcher winter wheat.

FIGS. 4A-4F are the sequences of the ACCase genes from the A, B and D genomes and the mutant AF28 A ACCase gene, the mutant AF26-B and mutant AF10-D gene.

FIG. 7 is a graph showing a comparison of wild type and mutant ACCase sequences in wheat A, B, D genomes, including a newly discovered non-synonymous single nucleotide polymorphism (SNP) in each mutant sequence.

FIG. 8 is a graph showing a comparison of ACCase enzyme tolerance to increasing quizalofop concentrations.

DEFINITIONS

Figure 1:
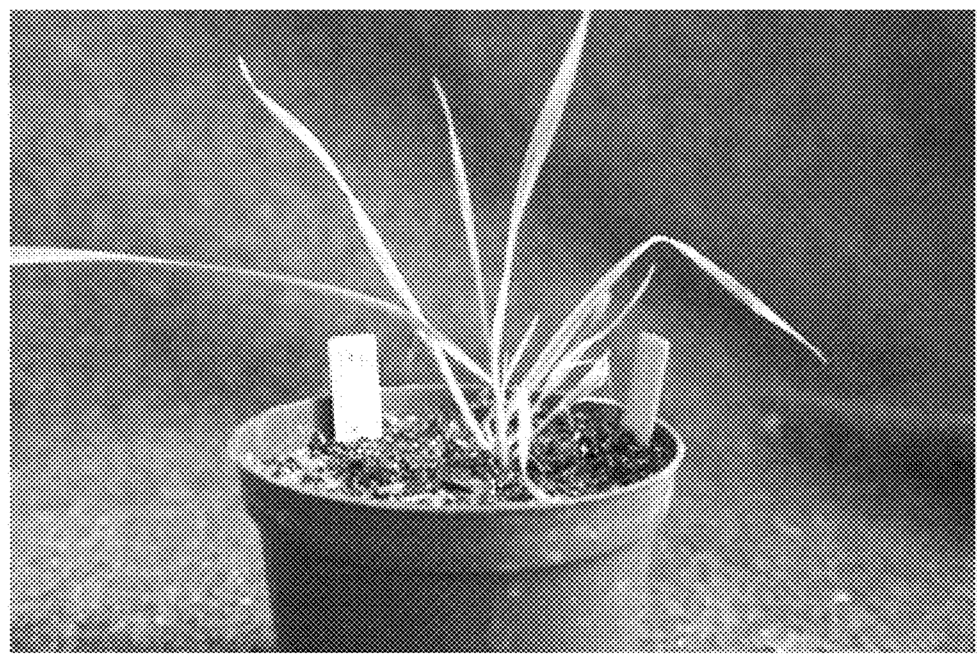
FIG. 1 is a photograph of the first herbicide tolerant plant discovered. This plant survived two lethal applications of clethodim herbicide.

In order to provide a clear and consistent understanding of the specification and the claims, including the scope given to such terms, the following definitions are provided. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

The term "conservatively modified variants" applies to both amino acid and nucleic acid sequences. With respect to particular nucleic acid sequences, conservatively modified variants refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company. Reference to any sequence herein shall be interpreted to include conservatively modified variants.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)).

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or cDNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., Molecular Cloning—A Laboratory Manual, 2nd ed., Vol. 1-3 (1989); and Current Protocols in Molecular Biology, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Unless otherwise stated, the term "ACCase nucleic acid" means a nucleic acid comprising a polynucleotide (an "ACCase polynucleotide") encoding an ACCase polypeptide with ACCase activity and includes all conservatively modified variants, homologs paralogs and the like. An "ACCase gene" is a gene of the present invention and refers to a heterologous genomic form of a full-length ACCase polynucleotide.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley, and millet.

As used herein, "polynucleotide" or includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of post-translation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" or "genetically modified" includes reference to a cell or vector, that has been altered by the introduction of a heterologous nucleic acid or that the cell is derived from a cell so modified. Thus, for example, recombinant or genetically modified cells express genes that are not found in identical form within the native (non-recombinant) form of the cell or express native genes that are otherwise abnormally expressed, under-expressed or not expressed at all as a result of deliberate human intervention. The term "recombinant" or "genetically modified" as used herein does not encompass the alteration of the cell or vector by naturally occurring events (e.g., spontaneous mutation, natural transformation/transduction/transposition) such as those occurring without deliberate human intervention.

As used herein, a "expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C. for 20 minutes.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with .gtoreq.90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, 4, 5, or 6° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acids Probes, Part I, Chapter 2, Ausubel, et al., Eds., Greene Publishing and Wiley-Interscience, New York (1995). In general a high stringency wash is 2× 15 min in 0.5×SSC containing 0.1% SDS at 65° C.

As used herein, "transgenic plant" or "genetically modified plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of an expression cassette. "Transgenic" or "genetically modified" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" or "genetically modified" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information www.hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters can be employed alone or in combination.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "variety" and "cultivar" refers to plants that are defined by the expression of the characteristics resulting from a given genotype or combination of genotypes, distinguished from any other plant grouping by the expression of at least one of the characteristics and considered as a unit with regard to its suitability for being propagated unchanged.

As used herein, the term "hybrid" refers to the offspring or progeny of genetically dissimilar plant parents or stock produced as the result of controlled cross-pollination as opposed to a non-hybrid seed produced as the result of natural pollination.

As used herein, the term "progeny" refers to generations of a plant, wherein the ancestry of the generation can be traced back to said plant. As used herein, the term "progeny" of an herbicide resistant plant includes both the progeny of that herbicide resistant plant, as well as any mutant, recombinant, or genetically engineered derivative of that plant, whether of the same species or a different species, where the herbicide resistant characteristic(s) of the original herbicide resistant plant has been transferred to the progeny plant.

As used herein, the term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, and a cell. In some embodiments of the present invention transgenic plants are crop plants. As used herein, the terms "crop" and "crop plant" are used in their broadest sense. The term includes, but is not limited to, any species of plant edible by humans or used as a feed for animal or fish or marine animal, or consumed by humans, or used by humans, or viewed by humans, or any plant used in industry or commerce or education.

As used herein, the term "elite germplasm" in reference to a plant refers to hereditary material of proven genetic superiority.

As used herein, the term "elite plant," refers to any plant that has resulted from breeding and selection for superior agronomic performance.

As used herein, the term "trait" refers to an observable and/measurable characteristic of an organism. For example, the present invention describes plants that are resistant to FOP and DIM herbicides.

As used herein, the terms "marker" and "DNA marker" and "molecular marker" in reference to a "selectable marker" refers to a physiological or morphological trait that may be determined as a marker for its own selection or for selection of other traits closely linked to that marker. For example, such a marker could be a gene or trait that associates with herbicide tolerance including, but not limited to, simple sequence repeat (SSR), single nucleotide polymorphism (SNP), genetic insertions and/or deletions and the like.

As used herein, the terms "introgress" and "introgressing" and "introgression" refer to conventional (i.e. classic) pollination breeding techniques to incorporate foreign genetic material into a line of breeding stock. For example, the present invention provides for wheat crop plants introgressed with a mutant ACCase gene for herbicide tolerance by crossing two plant generations.

As used herein, the terms "wild-type" when made in reference to a gene refer to a functional gene common throughout a plant population. A functional wild-type gene is that which is most frequently observed in a population and is thus arbitrarily designated the "normal" or "wild-type" form of the gene.

As used herein, the term "mutant" or "functional mutant" when made in reference to a gene or to a gene product refers, respectively, to a gene or to a gene product which displays modifications in sequence and/or functional properties (i.e., altered characteristics) when compared to the wild-type gene or gene product. Thus, the terms "modified" and "mutant" when used in reference to a nucleotide sequence refer to an nucleic acid sequence that differs by one or more nucleotides from another, usually related nucleotide acid sequence and the term "functional mutant" when used in reference to a polypeptide encodes by said "modified" or "mutant" nucleic acid refers to the protein or polypeptide that retains activity. In the present application, the ACCase mutant protein, "or functional mutant" thereof is an ACCase gene that retains its native activity to create essential amino acids. Additionally, a "modified" nucleotide sequence is interpreted as that found in the degenerate genetic code as known by those skilled in the art. For example, the genetic code is degenerate as there are instances in which different codons specify the same amino acid; a genetic code in which some amino acids may each be encoded by more than one codon. It is contemplated that the present invention may comprise such degeneracy (e.g., wherein a wheat hybrid comprises an ACCase gene that is at least 70% homologous, at least 80% homologous, at least 85% homologous, at least 90% homologous, at least 95% homologous, at least 97% homologous, or at least 99% homologous to SEQ ID NO: 1, 2, 3, 4, 5, or 6 or that found in AF28-A, AF26-B and/or AF10-D, (ATCC Nos. PTA-123074, PTA-123076 and PTA-123075) as found in, for example, the wheat germplasm.

DETAILED DESCRIPTION OF THE INVENTION

Acetyl-CoA carboxylase (ACC) is a biotinylated enzyme that catalyzes the carboxylation of acetyl-CoA to produce malonyl-CoA. This carboxylation is a two-step, reversible reaction consisting of the ATP-dependent carboxylation of the biotin group on the carboxyl carrier domain by biotin-carboxylase activity followed by the transfer of the carboxyl group from biotin to acetyl-CoA by carboxyl-transferase activity (Nikolau et al., 2003, Arch. Biochem. Biophys. 414:211-22). Acetyl-CoA carboxylase is not only a key enzyme in plants for biosynthesis of fatty acids, a process that occurs in chloroplasts and mitochondria, but ACCase also plays a role in the formation of long-chain fatty acids and flavonoids, and in malonylation that occurs in the cytoplasm. There are two isoforms of ACCase with the chloroplastic ACCase accounting for more than 80% of the total ACCase activity (Herbert et al., 1996, Biochem. J. 318:997-1006). Aryloxyphenoxypropionate (FOP) and cyclohexanedione (DIM) are two classes of chemicals that are known to selectively inhibit chloroplastic ACCase in grasses (Rendina et al., 1990, J. Agric. Food Chem. 38:1282-1287).

Seeds from a wheat variety were exposed to the chemical mutagen ethane methylsulfonate (EMS) and were planted and evaluated for tolerance to ACCase herbicides. One of the genotypes, AF28-A, (SEQ ID NO:4) expressed high levels of tolerance to each of the herbicides tested. It was further demonstrated herein that crossing the AF28-A, AF26-B and/or AF10-D, with elite parent lines yielded good seed set and ACCase herbicide resistance in progeny plants.

As such, one embodiment of the present invention provides a plant germplasm that contains altered ACCase genes and proteins. In some embodiments, the present invention provides for the use of ACCase herbicides in fields of hybrid plants to reduce the amount of monocot weed plants present in said crop field, wherein said hybrid germplasm comprises an altered ACCase enzyme that confers resistance to ACCase herbicides and said weed plants are ACCase herbicide susceptible. Preferred plants include wheat, rice and barley or other monocot cereal plants with an analogous mutation.

In one embodiment, the present invention provides a plant with resistance to inhibition by ACCase herbicides, singly or in conjunction with other resistance traits, for example insect resistance against the spotted stem borer *Chilo partellus* (Girijashankar et al., 2005, Plant Cell Rep. 24:513-522, incorporated herein in its entirety). In some embodiments, for example, a wheat hybrid whose germplasm comprises a synthetic cryl Ac gene from *Bacillus thuringiensis* (Bt) is introgressed into a wheat line whose germplasm confers resistance to ACCase herbicides. As well, the incorporation of ACCase herbicide resistance and insect resistance is accomplished via plant transgenesis into the same wheat hybrid. One skilled in the art will recognize the various techniques as described herein that are applicable to the incorporation of two or more resistance attributes into the same plant.

In one embodiment, the present invention provides ACCase herbicide resistance in plants comprising, for example, an ACCase germplasm designated AF28-A, AF26-B and/or AF10-D, ATCC Nos. PTA-123074, PTA-123076 and PTA-123075, incorporated into elite varieties through plant breeding and selection, thereby providing for the development of herbicide tolerant plants that will tolerate the use of ACCase inhibiting herbicides for weed control. Deployment of this herbicide tolerance trait in the aforementioned plants allows use of these herbicides to control monocot weeds that grow in the presence of these crops. In some embodiments, the incorporation of the ACCase resistance trait into elite lines is via introgression, or classical breeding methods. In some embodiments, the incorporation of the ACCase resistance gene into elite lines is via heterologous gene transgenesis with expression or inhibition constructs. In some embodiments, the invention provides a plant preferably wheat, wherein at least one ancestor of the wheat plant comprises an ACCase resistant gene from germplasm designated AF28-A, deposited under ATCC accession No: In some embodiments, the ACCase resistant herbicide gene includes a nucleic acid sequence that is at least 70% homologous, at least 80% homologous, at least 85% homologous, at least 90% homologous, at least 95% homologous, at least 97% homologous, or at least 99% homologous to SEQ ID NO:4, or the ACCase resistant herbicide gene as found in the AF28-A, deposited under ATCC accession No: PTA-123074. In some embodiments, the ACCase resistant herbicide gene is at least 70% homologous, at least 80% homologous, at least 85% homologous, at least 90% homologous, at least 95% homologous, at least 97% homologous, or at least 99% homologous SEQ ID NO:4 or the ACCase resistant herbicide gene as found in the AF28-A, deposited under ATCC accession No: PTA-123074, comprising an amino acid substitution Ala2004Val.

In some embodiments, ACCase herbicide resistant germplasm is introgressed into an elite plant line using classic breeding techniques. Examples of classical breeding methods for wheat, barley, rice and other monocot cereal plants can be found in, for example, Sleper and Poehlman, 2006, Breeding Field Crops, Fifth Edition, Blackwell Publishing, incorporated herein in its entirety.

In one embodiment, the ACCase herbicide resistant germplasm is introgressed into a plant, preferably wheat that provides food for human consumption. In some embodiments, the ACCase herbicide resistant germplasm is introgressed into wheat plants that provide food for livestock (e.g., poultry, cattle, swine, sheep, etc). In some embodiments, the ACCase herbicide resistant germplasm is introgressed into wheat plants that are used in industrial processes such as ethanol production. In one embodiment, the ACCase herbicide resistant gene is introduced into the plant genome via transgenesis using vectors and technologies known in the art.

In some embodiments, the present invention provides an ACCase resistant germplasm of a wheat plant part of line AF28-A, deposited under ATCC accession No: PTA-123074, and said wheat plant part is one or more of a pollen, an ovule, a tissue, a pod, a seed, and a cell. In one embodiment, the present invention provides an F1 hybrid whose germplasm comprises an ACCase resistance gene as described herein. In some embodiments, the F1 hybrid is a cross between two elite wheat lines, at least one of which contains a germplasm comprising an ACCase resistance gene as described herein.

In one embodiment, the present invention provides methods for controlling weeds in a population of plants. In some embodiments, controlling the weeds comprises applying an ACCase herbicide to said population of plants, such that weed growth is inhibited but plant growth is not adversely affected. In some embodiments, the ACCase herbicide being applied is from the aryloxyphenoxypropionate (FOP) herbicide family including, but not limited to, clodinafop-propargyl, cyhalofop-butyl, diclofop-methyl, fenoxaprop-p-ethyl, fluazifop-b-butyl, haloxyfop-ethoxyethyl, haloxyfop-etotyl, haloxyfop-R-methyl, propaquizafop, quizalofop-p-ethyl and quizalo-P-refuryl compounds. In some embodiments, the ACCase herbicide being applied is from the cyclohexanediones (DIM) herbicide family including, but not limited to, alloxydim, butroxydim, clefoxydim, clethodim, cycloxydim, profoxydim, sethoxydim, tepraloxydim and tralkoxydim compounds. In some embodiments, the ACCase herbicide being applied comprises a combination of compounds from both FOP and DIM ACCase herbicide families as disclosed herein. However, the present application is not limited to the ACCase herbicide used, and a skilled artisan will appreciate that new ACCase herbicides are being discovered at any given time that inhibit the ACCase enzyme.

In one embodiment, the present invention provides for a plant (e.g., F1, F2, F3, F4, etc.) whose germplasm confers resistance to ACCase herbicides and resistance to one or more additional herbicides from one or more different herbicide groups. For example, additional herbicide groups used to inhibit weed growth, include, but are not limited to, inhibitors of lipid synthesis (e.g., aryloxyphenoxypropionates, cyclohexanodeiones, benzofuranes, chloro-carbonic acids, phosphorodithioates, thiocarbamates), inhibitors of photosynthesis at photosystem II (e.g., phenyl-carbamates, pyridazinones, triazines, triazinones, triazolinones, uracils, amides, ureas, benzothiadiazinones, nitriles, phenyl-pyridines), inhibitors of photosynthesis at photosystem I (e.g., bipyridyliums), inhibitors of protoporphyrinogen oxidase (e.g., diphenylethers, N-phenylphthalimides, oxadiazoles, oxyzolidinediones, phenylpyrazoles, pyrimidindiones, thiadiazoles), inhibitors of carotenoid biosynthesis (e.g., pyridazinones, pyridinecarboxamides, isoxazolidinones, triazoles), inhibitors of 4-hydroxyphenyl-pyruvate-dioxygenase (e.g., callistemones, isoxazoles, pyrazoles, triketones), inhibitors of EPSP synthase (e.g., glycines), inhibitors of glutamine synthetase (e.g., phosphinic acids), inhibitors of dihydropteroate synthase (e.g., carbamates), inhibitors of microtubule assembly (e.g., benzamides, benzoic acids, dinitroanilines, phosphoroamidates, pyridines), inhibitors of cell division (e.g., acetamides, chloroacetamides, oxyacetamides), inhibitors of cell wall synthesis (e.g., nitriles, triazolocarboxamides) and inhibitors of auxin transport (e.g., phthalamates, semicarbazones). In some embodiments, the present invention provides F1 hybrids from elite plant lines that comprise resistance to one or more ACCase herbicides alone, or in conjunction with, herbicide resistance to one or more of the aforementioned herbicide groups.

In one embodiment, the present invention provides use of a heterologous nucleotide sequence comprising SEQ ID NOS: 1, 2, 3, 4, 5, or 6 encoding a wild-type or mutant ACCase protein (SEQ ID NOS 7, 8, 9, 10, 11 or 12) for providing the selected agronomic trait of ACCase herbicide resistance. In one embodiment, the nucleotide sequence comprises a mutant ACCase gene as found in the germplasm designated AF28-A, AF26-B and/or AF10-D, deposited under ATCC accession Nos. PTA-123074, PTA-123076 and PTA-123075. In some embodiments, the nucleotide sequence is at least 70% homologous, at least 80% homologous, at least 85% homologous, at least 90% homologous, at least 95% homologous, at least 97% homologous, or at least 99% homologous to the SEQ ID NO:1, SEQ ID NO:2, SEQ ID NO:3, SEQ ID NO:4, SEQ ID NO:5, or SEQ ID NO:6. In some embodiments, the ACCase nucleotide sequence is operably linked to a promoter sequence and forms part of an expression or inhibition construct, and in some embodiments the ACCase nucleotide sequence is at least 70% homologous, at least 80% homologous, at least 85% homologous, at least 90% homologous, at least 95% homologous, at least 97% homologous, or at least 99% homologous to the ACCase resistant herbicide gene as found in the AF28-A, AF26-B and/or AF10-D, or SEQ ID NO:4, SEQ ID NO:5 and/or SEQ ID NO:6 comprising an amino acid substitution Ala 2004 Val in the A, B, or D genome.

Classical Breeding of Wheat

Field crops have been classically bred through techniques that take advantage of the plants method(s) of pollination. A plant is considered "self-pollinating" if pollen from one flower can be transmitted to the same or another flower on the same plant, whereas plants are considered "cross-pollinated" if the pollen has to come from a flower on a different plant in order for pollination to occur. Plants that are self-pollinated and selected over many generations become homozygous at most, if not all, of their gene loci, thereby producing a uniform population of true breeding progeny. A cross between two homozygous plants from differing backgrounds or two different homozygous lines will produce a uniform population of hybrid plants that will more than likely be heterozygous at a number of the gene loci. A cross of two plants that are each heterozygous at a number of gene loci will produce a generation of hybrid plants that are genetically different and are not uniform.

Wheat plants are self-pollinating plants, but they can also be bred by cross-pollination. The development of wheat hybrids requires the development of pollinator parents (fertility restorers) and seed parent inbreds using the cytoplasmic male sterility-fertility restorer system, the crossing of seed parents and pollinator parents, and the evaluation of the crosses. Wheat hybrids may also be developed using chemical hybridizing agents that are used to provide male sterility of the female parent of the hybrid. Pedigree breeding programs combine desirable traits; in the present application the desirable trait being plant resistance to ACCase herbicides. This trait is put into the breeding pool from one or more lines, such that new inbred lines are created by crossing, followed by selection of plants with the desired trait, followed by more crossing, etc. New inbreds are crossed with other inbred lines (e.g., elite plant lines like those described herein).

Pedigree breeding starts with the crossing of two genotypes, such as AF28-A, AF26-B and/or AF10-D, and an elite wheat line. If the original two parents do not provide all of the desired characteristics, then other sources can be included in the breeding population. For example, if a hybrid is desired such that both ACCase herbicide resistance and resistance to another herbicide group as described herein was desirous, then plants with both these attributes could be crossed using classical breeding techniques. In the pedigree method, superior plants are self-pollinated and selected in successive generations. In the succeeding generations, the heterozygous condition gives way to homogeneous lines of homozygous plants as a result of self-pollination and selection. Typically, in the pedigree method, five or more generations of selfing and selection are practiced (e.g., S1, S2, S3, S4, S5, etc.).

Backcrossing is used to improve a plant line. Backcrossing transfers one or more specific desirable traits from one source to another that lacks the traits. This is accomplished by, for example, crossing a donor (e.g., AF28-A) to an elite inbred line (e.g., an elite line). The progeny of this cross is then crossed back (i.e. backcrossing) to the elite inbred line, followed by selection in the resultant progeny for the desired trait (e.g., resistance to ACCase herbicides). Following five or more backcross generations with selection for the desired trait the progeny are typically heterozygous for the locus (loci) controlling the desired phenotype, but will be like the elite parent for the other genetic traits. The last backcrossing then is typically selfed in order to give a pure breeding progeny for the gene or genes being transferred.

In current hybrid wheat breeding programs, new parent lines are developed to be either seed-parent lines or pollen-parent lines depending on whether or not they contain fertility restoring genes; the seed-parent lines do not have fertility restoring genes and are male-sterile in certain cytoplasms (also known as "A" line plants) and male-fertile in other cytoplasms (also known as "B" line plants), whereas the pollen-parent lines are not male sterile and do contain fertility restoring genes (also known as "R" line plants). The seed-parent lines are typically created to be cytoplasmically male sterile such that the anthers are minimal to non-existent in these plants thereby requiring cross-pollination. The seed-parent lines will only produce seed, and the cytoplasm is transmitted only through the egg. The pollen for cross pollination is furnished through the pollen-parent lines that contain the genes necessary for complete fertility restoration in the F1 hybrid, and the cross combines with the male sterile seed parent to produce a high-yielding single cross hybrid with good grain quality.

Typically, this cytoplasmic male sterility-fertility restorer system is performed for the production of hybrid seed by planting blocks of rows of male sterile (seed-parent) plants and blocks of rows of fertility restorer (pollen-parent) plants, such that the seed-parent plants are wind pollinated with pollen from the pollen-parent plant. This process produces a vigorous single-cross hybrid that is harvested and planted by the consumer. Male sterile, seed-parent plants can also be created by genetically breeding recessive male-sterile nuclear genes into a particular population, however the cytoplasmic male sterility-fertility restorer system is typically the system used for breeding hybrid wheat, though chemically-induced male sterility has also been widely used. Sleper and Poehlman, 2006, Breeding Field Crops, Fifth Ed., Blackwell Publishing provides a good review of current wheat breeding procedures and is incorporated herein in its entirety.

The present invention is not limited to the wheat lines listed, and one skilled in the art will recognize that any elite wheat line would be equally amenable to the compositions and methods as described herein.

Plant Transgenics

Compositions of the present invention include the sequences for wheat nucleotide sequences which have been identified as ACCase encoding sequences that are involved in plant response to ACCase herbicides. In particular, the present invention provides for isolated nucleic acid molecules comprising nucleotide sequences encoding the amino acid sequences shown in SEQ ID NOs: 5, 6, 7, 8, and 9. Further provided are polypeptides having an amino acid sequence encoded by a nucleic acid molecule described herein, for example those nucleotide sequences set forth in SEQ ID NOs: 1, 2, 3, 4, 5, or 6.

The compositions of the invention can be used in a variety of methods whereby the protein products can be expressed in crop plants to function as herbicide resistant proteins. Such expression results in the alteration or modulation of the level, tissue, or timing of expression to achieve improved resistance to ACCase herbicides. The compositions of the invention may be expressed in the same species from which the particular ACCase originates, or alternatively, can be expressed in any plant of interest. In this manner, the coding sequence for the ACCase can be used in combination with a promoter that is introduced into a crop plant. In one embodiment, a high-level expressing constitutive promoter may be utilized and would result in high levels of expression of the ACC. In other embodiments, the coding sequence may be operably linked to a tissue-specific promoter to direct the expression to a plant tissue known to be susceptible to ACCase herbicides such as leaves. Likewise, manipulation of the timing of expression may be utilized. For example, by judicious choice of promoter, expression can be enhanced early in plant growth to prime the plant to be responsive to herbicide treatment.

In specific embodiments, methods for increasing herbicide tolerance in a plant comprise stably transforming a plant with a DNA construct comprising a nucleotide sequence of the invention operably linked to a promoter that drives expression in a plant.

Transformed plants, plant cells, plant tissues and seeds thereof are additionally provided.

The methods of the invention can be used with other methods available in the art for enhancing other traits in plants. It is recognized that such second nucleotide sequences may be used in either the sense or antisense orientation depending on the desired outcome.

It is this over-expression of mutant ACCase nucleotide sequences (SEQ ID NO:4, 5, and/or 6) that would be the preferred method of use of the mutant nucleotide sequences The various advantages and disadvantages of using different promoters to drive such over-expression is well known by those skilled in the art. However, by way of example, a constitutive promoter could drive the expression, but a more ideal promoter would target tissues, such as the leaves.

Sequences of the invention, as discussed in more detail below, encompass coding sequences, antisense sequences, and fragments and variants thereof. Expression of the sequences of the invention can be used to modulate or regulate the expression of corresponding ACCase proteins. The invention encompasses isolated or substantially purified nucleic acid or protein compositions.

Fragments and variants of the disclosed nucleotide sequences and proteins encoded thereby are also encompassed by the present invention. "Fragment" means a portion of the nucleotide sequence or a portion of the amino acid sequence and hence protein encoded thereby. Fragments of a nucleotide sequence may encode protein fragments that retain the biological activity of the native protein and hence have ACC-like activity and thereby affect herbicide response. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a ACCase nucleotide sequence that encodes a biologically active portion of a ACCase protein of the invention will encode at least 15, 25, 30, 50, 100, 150, 200, or 250 contiguous amino acids, or up to the total number of amino acids present in a full-length protein of the invention The nucleotide sequences of the invention can be used to isolate corresponding sequences from other organisms, particularly other plants, more particularly other monocots. In this manner, methods such as polymerase chain reaction (PCR), hybridization, and the like can be used to identify such sequences based on their sequence homology to the sequences set forth herein. Sequences isolated based on their sequence identity to the entire ACCase sequences set forth herein or to fragments thereof are encompassed by the present invention. Such sequences include sequences that are orthologs of the disclosed sequences. "Orthologs" means genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in, for example, Sambrook. See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the ACCase sequences of the invention. Methods for preparation of probes for hybridization and for construction of cDNA and genomic libraries are generally known in the art and are disclosed in Sambrook.

Biological activity of the ACCase polypeptides (i.e., influencing the ACCase herbicide response) can be assayed by any method known in the art and disclosed herein.

The nucleic acid sequences of the present invention can be expressed in a host cell such as bacteria, yeast, insect, mammalian, or preferably plant cells. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

The sequences of the invention are provided in expression cassettes or DNA constructs for expression in the plant of interest. The cassette will include 5' and 3' regulatory sequences operably linked to a ACCase sequence of the invention. The cassette may additionally contain at least one additional gene to be cotransformed into the organism. Alternatively, the additional gene(s) can be provided on multiple expression cassettes.

Such an expression cassette is provided with a plurality of restriction sites for insertion of the ACCase sequence to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the invention, a translational termination region and, optionally, a transcriptional termination region functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other.

While it may be preferable to express the sequences using heterologous promoters, the native promoter sequences may be used. Such constructs would change expression levels of ACCase in the host cell (i.e., plant or plant cell). Thus, the phenotype of the host cell (i.e., plant or plant cell) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) PNAS USA 86:6126-6130); potyvirus leaders, for example, TEV leader (Tobacco Etch Virus) (Allison et al. (1986) Virology 154: 9-20); and human immunoglobulin heavy-chain binding protein (BiP), (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968. Other methods known to enhance transcription can also be utilized.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate, glyphosate, ammonium, bromoxynil, imidazolinones, and 2,4-dichlorophenoxyacetate (2,4-D). See generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724; and WO Publication Nos. 02/36782. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); PEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Just as expression of an ACCase polypeptides of the invention may be targeted to specific plant tissues or cell types through the use of appropriate promoters, it may also be targeted to different locations within the cell through the use of targeting information or "targeting labels". Unlike the promoter, which acts at the transcriptional level, such targeting information is part of the initial translation product. Depending on the mode of infection of the pathogen or the metabolic function of the tissue or cell type, the location of the protein in different compartments of the cell may make it more efficacious against a given pathogen or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene.

There are many signal peptides described in the literature, and they are largely interchangeable (Raikhel N, Chrispeels M J (2000) Protein sorting and vesicle traffic. In B Buchanan, W Gruissem, R Jones, eds, Biochemistry and Molecular Biology of Plants. American Society of Plant Physiologists, Rockville, Md., pp 160-201, herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the pathogen and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to affect phenotypic changes in the organism. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al. (1986) Proc. Natl. Acad. Sci. USA 83:5602-5606), *Agrobacterium*-mediated transformation (Townsend et al., U.S. Pat. No. 5,563,055 and Zhao et al., U.S. Pat. No. 5,981,840), direct gene transfer (Paszkowski et al. (1984) EMBO J. 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923-926). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In vitro Cell Dev. Biol. 27P: 175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, New York), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic. One of skill will recognize that after the recombinant expression cassette is stably incorporated in transgenic plants and confirmed to be operable, it can be introduced into other plants by sexual crossing. Any of number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plans that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant are also contemplated.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena sativa*), barley (*Hordeum vulgare*), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the present invention include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true first such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, barley, rice, millet, tobacco, etc.).

Prokaryotic cells may be used as hosts for expression. Prokaryotes most frequently are represented by various strains of *E. coli*, however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) Nature 198:1056), the tryptophan (trp) promoter system (Goeddel et al. (1980) Nucleic Acids Res. 8:4057) and the lambda derived P L promoter and N-gene ribosome binding site (Shimatake et al. (1981) Nature 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) Gene 22:229-235 and Mosbach et al. (1983) Nature 302:543-545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention. Such antimicrobial proteins can be used for any application including coating surfaces to target microbes. In this manner, target microbes include human pathogens or microorganisms.

Synthesis of heterologous nucleotide sequences in yeast is well known. Sherman, F., et al. (1982) Methods in Yeast Genetics, Cold Spring Harbor Laboratory is a well-recognized work describing the various methods available to produce a protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques, radioimmunoassay, or other standard immunoassay techniques.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The present invention further provides a method for modulating (i.e., increasing or decreasing) the concentration or composition of the polypeptides of the present invention in a plant or part thereof. Increasing or decreasing the concentration and/or the composition of polypeptides in a plant can affect modulation. For example, increasing the ratio of polypeptides of the invention to native polypeptides can affect modulation. The method comprises: introducing a polynucleotide of the present invention into a plant cell with a recombinant expression cassette as described above to obtain a transformed plant cell, culturing the transformed plant cell under appropriate growing conditions, and inducing or repressing expression of a polynucleotide of the present invention in the plant for a time sufficient to modulate the concentration and/or the composition of polypeptides in the plant or plant part.

Increasing the Activity and/or Level of a ACCase Polypeptide

Methods are provided to increase the activity and/or level of the ACCase mutant polypeptides to increase tolerance to ACCase herbicides. An increase in the level and/or activity of the ACCase mutant polypeptide can be achieved by providing to the plant a ACCase polypeptide. The polypeptide can be provided by introducing mutant ACCase polypeptide into the plant, introducing into the plant a nucleotide sequence encoding a mutant ACCase polypeptide or alternatively by modifying a genomic locus encoding the ACCase polypeptide of the invention.

As discussed elsewhere herein, many methods are known in the art for providing a polypeptide to a plant including, but not limited to, direct introduction of the polypeptide into the plant, introducing into the plant (transiently or stably) a polynucleotide construct encoding a polypeptide having enhanced ACCase activity. It is also recognized that the methods of the invention may employ a polynucleotide that is not capable of directing, in the transformed plant, the expression of a protein or an RNA. Thus, the level and/or activity of a ACCase mutant polypeptide may be increased by altering the gene encoding the mutant ACCase polypeptide or its promoter. See, e.g., Kmiec, U.S. Pat. No. 5,565,350; Zarling, et al., PCT/US93/03868. Therefore mutagenized plants that carry mutations in ACCase genes, where the mutations increase expression of the mutant ACCase gene or increase the activity of the encoded polypeptide are provided.

Reducing the Activity and/or Level of an ACCase Polypeptide

Methods are also provided to reduce or eliminate the activity of an ACCase polypeptide by transforming a plant cell with an expression cassette that expresses a polynucleotide that inhibits the expression of the ACC. The polynucleotide may inhibit the expression of the ACCase directly, by preventing transcription or translation of the ACCase synthase messenger RNA, or indirectly, by encoding a polypeptide that inhibits the transcription or translation of an ACCase gene encoding an ACCase polypeptide. Methods for inhibiting or eliminating the expression of a gene in a plant are well known in the art, and any such method may be used in the present invention to inhibit the expression of the ACCase polypeptide. Many methods may be used to reduce or eliminate the activity of an ACCase synthase polypeptide. In addition, more than one method may be used to reduce the activity of a single ACCase polypeptide.

1. Polynucleotide-Based Methods:

In some embodiments of the present invention, a plant is transformed with an expression cassette that is capable of expressing a polynucleotide that inhibits the expression of an ACCase synthase polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one ACCase synthase polypeptide is an expression cassette capable of producing an RNA molecule that inhibits the transcription and/or translation of at least one ACCase synthase polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an ACCase synthase polypeptide include sense Suppression/Cosuppression, where an expression cassette is designed to express an RNA molecule corresponding to all or part of a messenger RNA encoding an ACCase synthase polypeptide in the "sense" orientation and over expression of the RNA molecule can result in reduced expression of the native gene; Antisense Suppression where the expression cassette is designed to express an RNA molecule complementary to all or part of a messenger RNA encoding the ACCase synthase polypeptide and over expression of the antisense RNA molecule can result in reduced expression of the native gene; Double-Stranded RNA Interference, where a sense RNA molecule like that described above for cosuppression and an antisense RNA molecule that is fully or partially complementary to the sense RNA molecule are expressed in the same cell, resulting in inhibition of the expression of the corresponding endogenous messenger RNA, Hairpin RNA Interference and Intron-Containing Hairpin RNA Interference, where the expression cassette is designed to express an RNA molecule that hybridizes with itself to form a hairpin structure that comprises a single-stranded loop region and a base-paired stem, Small Interfering RNA or Micro RNA, where the expression cassette is designed to express an RNA molecule that is modeled on an endogenous miRNA gene.

2. Polypeptide-Based Inhibition of Gene Expression

In one embodiment, the polynucleotide encodes a zinc finger protein that binds to a gene encoding an ACCase polypeptide, resulting in reduced expression of the gene, Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication Nos. 2003/0037355; each of which is herein incorporated by reference.

3. Polypeptide-Based Inhibition of Protein Activity

In some embodiments of the invention, the polynucleotide encodes an antibody that binds to at least one ACCase and reduces the activity of the ACCase synthase polypeptide. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present invention, the activity of an ACCase synthase polypeptide is reduced or eliminated by disrupting the gene encoding the ACCase synthase polypeptide. The gene encoding the ACCase synthase polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced ACCase activity.

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, (SEQ ID NOS: 1, 2, 3, 4, 5, or 6), or with other genes implicated in herbicide resistance. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409)); barley high lysine (Williamson et al. (1987) Eur. J. Biochem. 165:99-106; and WO 98/20122); and high methionine proteins (Pedersen et al. (1986) J. Biol. Chem. 261:6279; Kirihara et al. (1988) Gene 71:359; and Musumura et al. (1989) Plant Mol. Biol. 12: 123)); increased digestibility (e.g., modified storage proteins (U.S. application Ser. No. 10/053,410, filed Nov. 7, 2001)); and thioredoxins (U.S. application Ser. No. 10/005,429, filed Dec. 3, 2001), the disclosures of which are herein incorporated by reference.

The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) Gene 48:109); lectins (Van Damme et al. (1994) Plant Mol. Biol. 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene and GAT gene)); and traits desirable for processing or process products such as high oil (U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (U.S. Pat. No. 5,602,321); beta-ketothiolase, polyhydroxybutyrate synthase, and acetoacetyl-CoA reductase (Schubert et al. (1988) J. Bacteriol. 170:5837-5847), which facilitate expression of polyhydroxyalkanoates (PHAs)), the disclosures of which are herein incorporated by reference. One could also combine the polynucleotides of the present invention with polynucleotides providing agronomic traits such as male sterility (see U.S. Pat. No. 5,583,210), stalk strength, flowering time, or transformation technology traits such as cell cycle regulation or gene targeting (see, WO 99/61619; WO 00/17364; WO 99/25821), the disclosures of which are herein incorporated by reference.

These stacked combinations can be created by any method including, but not limited to, polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., Plant Molecular Biology: A Laboratory Manual, Chapter 7, Clark, Ed., Springer-Verlag, Berlin (1997). For molecular marker methods, see generally, The DNA Revolution by Andrew H. Paterson 1996 (Chapter 2) in: Genome Mapping in plants (Ed., Andrew H. Paterson) by Academic Press/R. G. Lands Company, Austin, Tex., pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes hybridize, under selective hybridization conditions, to a gene encoding a polynucleotide of the present invention. In preferred embodiments, the probes are selected from polynucleotides of the present invention. Typically, these probes are cDNA probes or restriction enzyme treated (e.g., PST I) genomic clones. The length of the probes is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome compliment. Some exemplary restriction enzymes employed in RFLP mapping are EcoRI, EcoRV, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present invention of the genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample, preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The following examples are provided in order to demonstrate and further illustrate certain preferred embodiments and aspects of the present invention and are not to be construed as limiting the scope thereof.

Example 1

An Acetyl Co-Enzyme a Carboxylase Inhibitor Tolerant Wheat (*Triticum aestivum* L.) for Use in a Herbicide Tolerant Cropping System A winter wheat (*Triticum aestivum* L.) with tolerance to the Acetyl Co-Enzyme A Carboxylase (ACC) inhibitor class of herbicides was developed via the following method:

Winter wheat seed, variety Hatcher, was subjected to a potent chemical mutagen (non-transgenic method), ethane methylsulfonate (EMS), at a rate of 0.75% for 2.5 hours. This seed is hereby denoted M1, each subsequent generation of seed will be denoted with a sequentially increasing numeral following the M. This resulted in a mutation frequency in the wheat genome of about 1 mutation per 96 kb (calculated in the M2 generation). This wheat was planted in February and harvested July. The resulting M2 seed was planted in the field in September at a total population of 2.5 million plants.

In May the following year, the field was divided into two sections; one section was treated with a lethal dose of quizalofop (~1 millions plants) and the other section was treated with a lethal dose of clethodim (~1.5 million plants). Quizalofop and clethodim are highly effective ACCase inhibitors (lipid synthesis inhibitor). The quizalofop portion of the field was treated a second time in June. 46 quizalofop and 167 clethodim survivors' heads were collected from the field July.

Concurrently a small portion of M2 seed was planted in the greenhouse from January-April. Approximately 75,000 and 175,000 plants were screened with lethal doses of quizalofop and clethodim respectively. After application, a small subset of clethodim survivors (7 plants) that appeared healthier than the rest were screened a second time. This was the first documented incidence of improved herbicide tolerance in our mutant population (FIG. 1), May. In total, 26 quizalofop and 42 clethodim survivors were harvested from these sets of plants.

Figure 2:
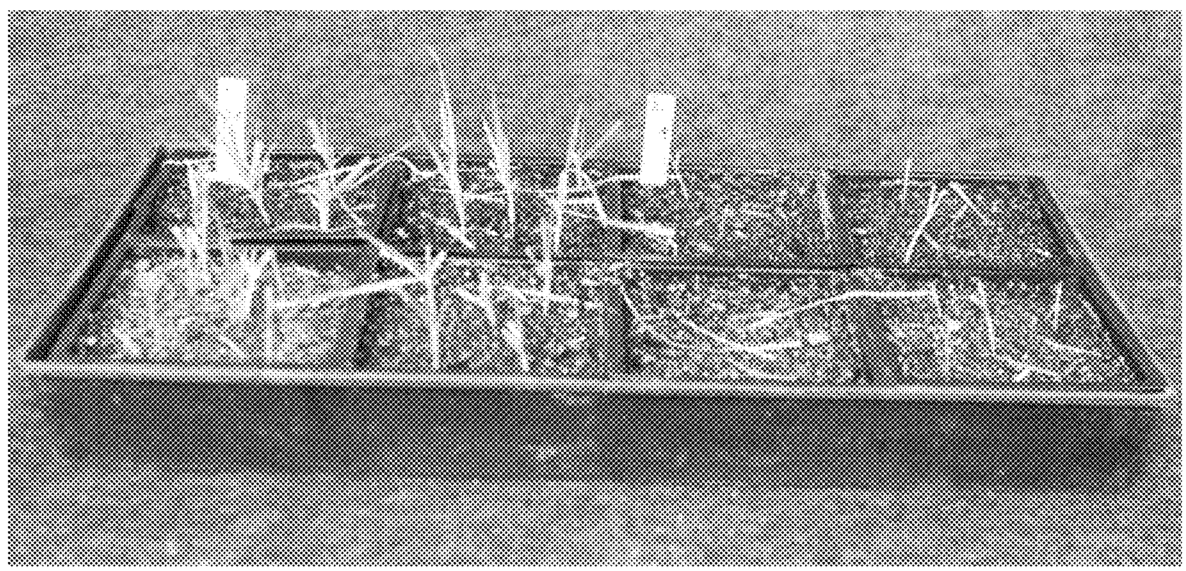
FIG. 2 is a photograph of M3 plants grown from seed of two M2 parents. Plants were treated with two sequential rates of a lethal dose of quizalofop. The plants on the left survived both herbicide applications; the plants on the right died after one application.
Figure 3:
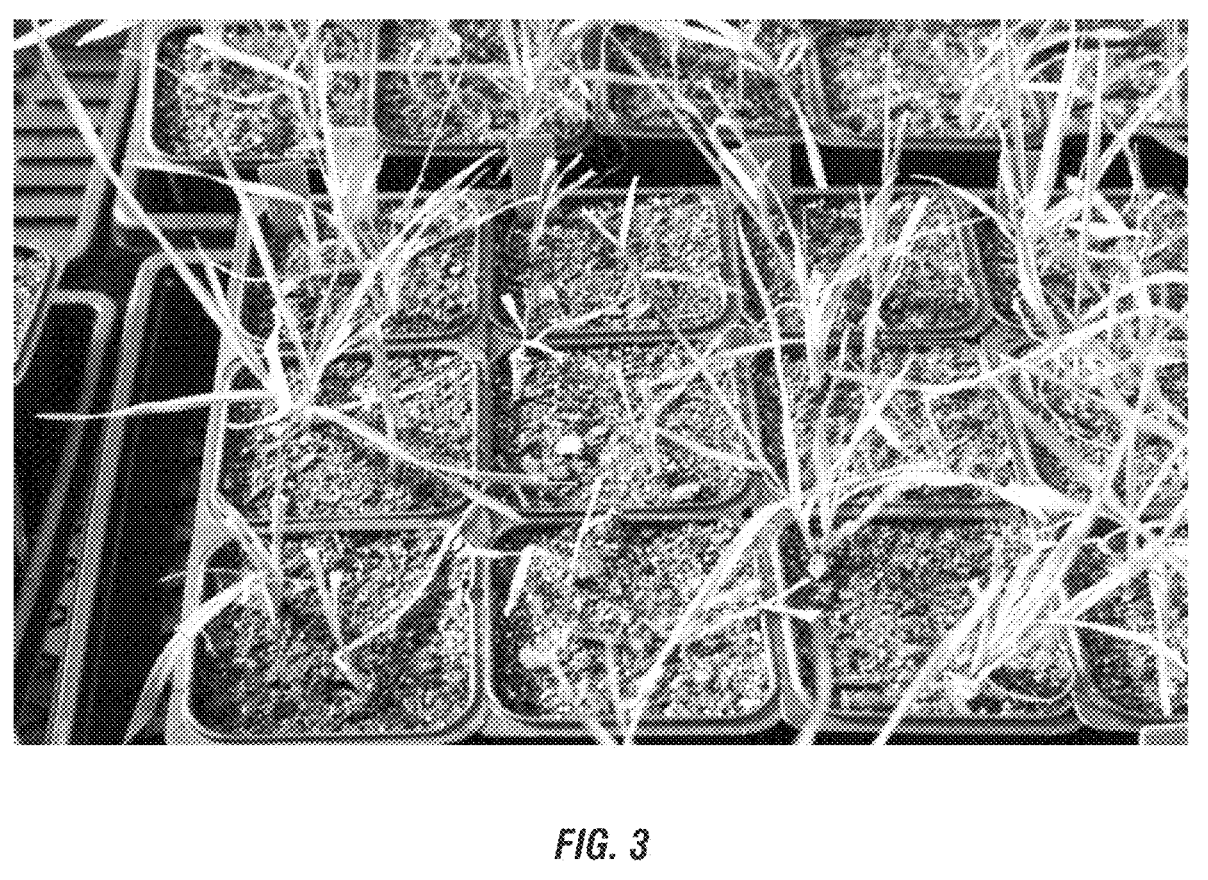

The M3 generation collected from the field has now been screened in the greenhouse (August-October) for quizalofop and clethodim with two sequential rates of a lethal dose of herbicide (FIG. 2). Some accessions exhibited a high survival rate compared to other mutant plants and the un-mutagenized check. Some preliminary characterization studies investigating the various mutations have begun. FIG. 3 shows some M3 ACCase tolerant accessions compared to the un-mutagenized check.

These screenings provide clear evidence that this wheat has acquired ACCase resistance that is inheritable and functional.

Example 2

An Acetyl Co-Enzyme a Carboxylase Inhibitor Tolerant Wheat (*Triticum aestivum* L.) for Use in a Herbicide Tolerant Cropping System A winter wheat (*Triticum aestivum* L.) with tolerance to the Acetyl Co-Enzyme A Carboxylase (ACC) inhibitor class of herbicides was characterized via the following methods:

Plants exhibiting an increased tolerance to quizalofop herbicide were screened with multiple methods for identifying and characterizing the cause of increase. Plants were screened for visual injury, whole-plant quizalofop tolerance differences, cross-resistance to other herbicides, and evaluated genotypically and enzymatically.

Figure 5:
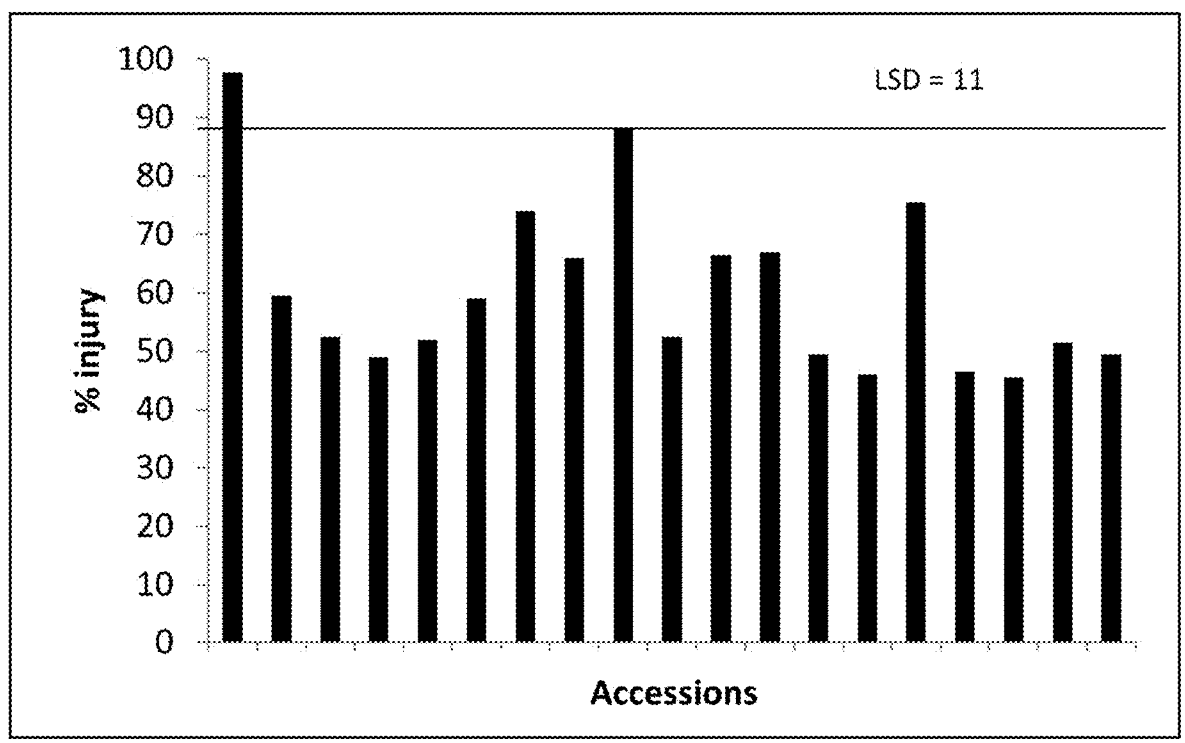
FIG. 5 is a graph depicting visual injury of M2-derived M3 mutants screened with quizalofop. Values below the horizontal line are different than the non-mutagenized Hatcher check, represented by the far left bar.

Visual evaluation. 18 quizalofop-tolerant accessions were treated with 21.05 g ai $ha^{-1}$ quizalofop, a discriminating dose based on previous studies. Plants were evaluated 28 days after treatment (DAT) for visible injury to quizalofop on a scale of 0 to 100%, with 0 being no injury and 100 being complete desiccation. Nearly all accessions evaluated in this study appeared more tolerant to quizalofop than non-mutant Hatcher wheat (FIG. 5). The accessions contained few completely dead plants, with the exception of the one accession not different than the background.

Figure 6:
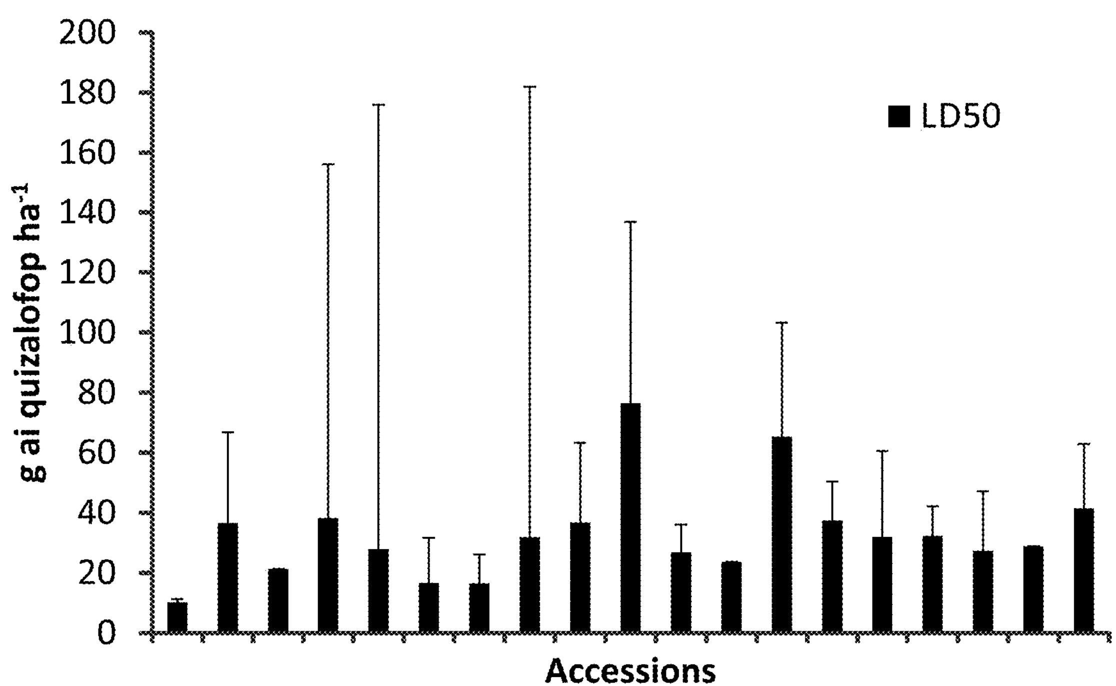
FIG. 6 is a graph depicting a dose response trial with quizalofop comparing the non-mutagenized Hatcher check, represented by the left bar, with M2-selected M3 accessions.
Figure 9:
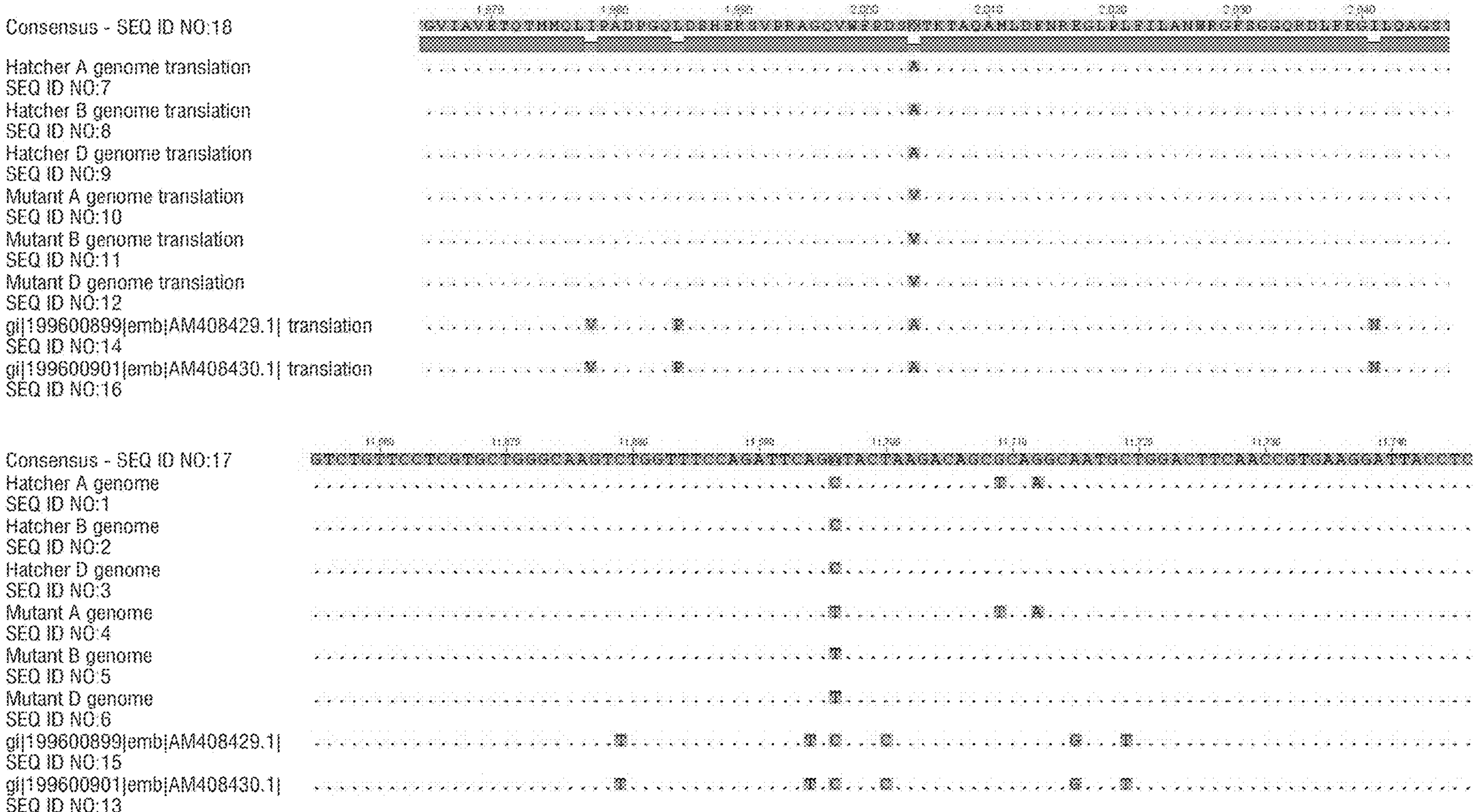
FIG. 9 shows alignment of the sequences of the invention to black grass reference sequence and to each other.

Dose response. A dose response study was completed with 11, 23, 46, 92, and 184 g quizalofop $ha^{-1}$. Seven DAT the tops of plants were cut off above the newest above-ground growing point. Binomial evaluation of plant survival was performed 28 DAT. Differences were uncovered in the whole plant sensitivity to increasing application rates of quizalofop. $LD_{50}$'s ranged from 10 g ai $ha^{-1}$, with the non-treated, to 76 g ai $ha^{-1}$ (FIG. 6). Resistant to susceptible ratios for this experiment ranged from 1.6 to 7.5 based on survival/death of the plants.

Cross-resistance. A cross-resistance study was conducted within the ACCase herbicide mode of action using herbicides normally lethal to wheat. Clethodim, sethoxydim, and fluazifop were used at rates of 65, 264, and 361 g ai $ha^{-1}$, plus a treatment of clethodim and 10.5 g ai $ha^{-1}$ quizalofop. Seven DAT the tops of plants were cut off above the newest above-ground growing point. Binomial evaluation of plant survival was performed 28 DAT. Tolerance of quizalofop mutants to clethodim and sethoxydim was low (Table 1). The presence of any cross tolerance presents evidence that combining multiple homoeologous resistant ACCase genes into a single plant could lead to resistance to additional herbicides. At this stage only a third of the total ACCase in the plant would have a mutation and contain tolerance to ACCase inhibitors if the mutation is target-site-based.

DNA sequencing. DNA was collected from 26 quizalofop-tolerant phenotypes. Genome-specific primers were developed to amplify sequences from the A, B, and D ancestral wheat genomes. Sequence results were compared to previously cloned non-mutant wheat sequences to determine the presence of nucleotide substitutions. When comparing sequences from non-mutant Hatcher to mutant phenotypes, three non-synonymous mutations were revealed in the ACCase carboxyltransferase domain, all at position 2004 in the *Alopecurus myosuroides* amino acid numbering system. This mutation on the A genome was found in eight accessions, on the B genome in nine accessions, and on the D genome in nine accessions. No accession had more than one of these SNPs. The mutation was a C to T substitution resulting in an alanine to valine change in the amino acid sequence (FIG. 7). Each accession with higher survival than the background contained one of these SNPs. Based on the chromatograph patterns, the majority these SNPs are also believed to be homozygous in the plant.

ACCase enzyme characterization. An in-vitro enzyme assay was conducted to observe ACCase in conjunction with quizalofop directly to determine if the presence of ACCase mutations decreases the ability of herbicides to inhibit ACCase activity. Four quizalofop concentrations of 0.1, 1, 10, and 100 μM were included in the assay along with a non-treated control. The experiment included four accessions which included a representative from the three mutations detected and non-mutagenized wheat. Non-mutagenized Hatcher winter wheat had greater sensitivity to quizalofop than the mutant accessions (FIG. 8). Plants with the B and D genome nucleotide substitution resulted in higher than background levels of tolerance to quizalofop at the 10 μM, and plants with the A and D genome nucleotide substitution had higher than background tolerance at the 100 μM concentration, with LSD's ($\alpha$=0.05) of 14.5 and 21.6, respectively. Calculated at the 125 level, the resistant to susceptible value for the A genome was 4.57, the B genome was 3.57 and the D genome was 10.86.

Based on these experiments, the largest factor in plant tolerance to quizalofop is the presence of a C to T nucleotide substitution at position 2004.

TABLE 1

Quizalofop tolerant mutant survival after application of other ACCase herbicides. Accession 0 is the non-mutant check.

| | Herbicide treatment | | | |
|---|---|---|---|---|
| Accession | Clethodim | Sethoxydim | Fluazifop | Cleth. + quiz. |
| Nos. | % | % | % | % |
| 0 | 0 | 0 | 0 | 0 |
| 1 | 10 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 25 | 0 | 0 | 0 |
| 9 | 17 | 0 | 0 | 0 |
| 10 | 0 | 0 | 0 | 0 |
| 11 | 0 | 8 | 0 | 0 |
| 12 | 17 | 8 | 0 | 0 |
| 13 | 0 | 0 | 0 | 0 |
| 14 | 0 | 0 | 0 | 0 |
| 15 | 0 | 0 | 0 | 0 |
| 16 | 0 | 0 | 0 | 0 |
| 17 | 0 | 0 | 0 | 0 |
| LSD = 16 | | | | |

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

DEPOSIT STATEMENT

A deposit of seed of wheat variety AF28, AF26, and A10 disclosed herein, is and has been maintained by Colorado State University, Ft. Collins, Colorado 80523 since prior to the filing date of this application and all provisional applications referenced and incorporated herein. Access to this deposit will be available during the pendency of the application to the Commissioner of Patents and Trademarks and persons determined by the Commissioner to be entitled thereto upon request. Upon allowance of any claims in the application, the Applicant(s) will make available to the public without restriction a deposit of at least 2500 seeds of each variety or line with the American Type Culture Collection (ATCC), Rockville, Maryland, 20852. The seeds deposited with the ATCC will be taken from the same deposit maintained at Colorado State University as described above. Additionally, Applicant(s) will meet all the requirements of 37 C.F.R. § 1.801-1.809, including providing an indication of the viability of the sample when the deposit is made. This deposit of the aforementioned wheat varieties will be maintained in the ATCC Depository, which is a public depository, for a period of 30 years, or 5 years after the most recent request, or for the enforceable life of the patent, whichever is longer, and will be replaced if it ever becomes nonviable during that period. Applicant will impose no restrictions on the availability of the deposited material from the ATCC; however, Applicant has no authority to waive any restrictions imposed by law on the transfer of biological material or its transportation in commerce.

What is claimed is:

1. A method of screening a population of plants for resistance to acetyl-CoA carboxylase inhibiting herbicides comprising:

a) applying one or more acetyl-CoA carboxylase inhibiting herbicides to the population of plants;

b) obtaining a nucleic acid sample from a plant of the population that is resistant to the acetyl-CoA carboxylase inhibiting herbicide; and c) assaying said nucleic acid sample for the presence of a nucleic acid sequence which encodes an acetyl-CoA carboxylase protein that includes a mutation at a position corresponding to position 2004 of the black grass reference sequence, SEQ ID NOS: 14 or 16.

2. The method of claim 1, wherein said one or more mutations comprise an amino acid substitution Ala2004Val when referenced to black grass, SEQ ID NOS: 14 or 16.

3. The method of claim 1, wherein the assaying comprises PCR or DNA hybridization.

4. The method of claim 1, wherein the plant is a monocot cereal plant.

5. The method of claim 4, wherein the monocot cereal plant is selected from wheat, barely, triticale, rice, or maize.

6. The method of claim 1, wherein said acetyl-CoA carboxylase inhibiting herbicides are selected from aryloxyphenoxypropionates, cyclohexanediones, and phenylpyrazolin (DENs).

7. The method of claim 1, wherein the nucleic acid sample comprises one or more mutations in the acetyl-CoA carboxylase gene as found in AF28-A, AF26-B and/or AF10-D, wherein representative samples of seeds of AF28-A, AF26-B and AF10-D have been deposited under ATCC Nos PTA-123074, PTA-123076, and PTA-123075, respectively.

8. The method of claim 1, wherein said nucleic acid sample comprises SEQ ID NO: 4, 5, or 6.

9. The method of claim 1, wherein said nucleic acid sample comprises a nucleic acid sequence encoding SEQ ID NO: 8, 10, or 12.

* * * * *

SEQUENCE LISTING

<160> NUMBER OF SEQ ID NOS: 18

<210> SEQ ID NO 1
<211> LENGTH: 1152
<212> TYPE: DNA
<213> ORGANISM: Triticum aestivum

<400> SEQUENCE: 1
cgtgttggat ggtctgatga tggcagccct gaacgtgggt ttcagtacat ttatctgact 60
gaagaagacc atgctcgtat tagcacttct gttatagcgc acaagatgca gcttgataat 120
ggtgaaatta ggtgggttat cgattctgtt gtggggaagg aggatgggct aggtgtggag 180
aacatacatg gaagtgctgc tattgccagt gcctattcta gggcctatga ggagacattt 240
acgcttacat ttgtgactgg acggactgtt ggaataggag catatcttgc tcgacttggc 300
atacggtgca tacagcgtac tgaccagccc attatcctaa ctgggttctc tgccttgaac 360
aagcttcttg gccgggaagt ttacagctcc cacatgcagt tgggtggccc caaaattatg 420
gcgacaaacg gtgttgtcca tctgacagtt tcagatgacc ttgaaggtgt atctaatata 480
ttgaggtggc tcagctatgt tcctgccaac attggtggac ctcttcctat tacaaaatct 540
ttggacccac ctgacagacc cgttgcttac atccctgaga atacatgcga tcctcgtgct 600
gccatcagtg gcattgatga tagccaaggg aaatggttgg ggggcatgtt cgacaaagac 660
agttttgtgg agacatttga aggatgggcg aagtcagttg ttactggcag agctaaactc 720
ggagggattc cggtgggtgt tatagctgtg gagacacaga ctatgatgca gctcatccct 780
gctgatccag gccagcttga ttcccatgag cggtctgttc ctcgtgctgg gcaagtctgg 840
tttccagatt cagctactaa gacagcgcag gcaatgctgg acttcaaccg tgaaggatta 900
cctctgttca tccttgctaa ctggagaggc ttctctggtg gacaaagaga tctttttgaa 960
ggaatccttc aggctgggtc aacaattgtt gagaacctta ggacatacaa tcagcctgcc 1020
tttgtatata tccccaaggc tgcagagcta cgtggagggg cttgggtcgt gattgatagc 1080
aagataaatc cagatcgcat tgagttctat gctgagagga ctgcaaaggg caatgttctc 1140
gaacctcaag gg 1152

<210> SEQ ID NO 2
<211> LENGTH: 1161
<212> TYPE: DNA
<213> ORGANISM: Triticum aestivum

<400> SEQUENCE: 2
atcttgcttc cgtgttggat ggtctgatga tggcagccct gaacgtgggt ttcaatatat 60
ttatctgact gaagaagacc atgctcgtat tagcgcttct gttatagcgc acaagatgca 120

```
gcttgataat ggtgaaatta ggtgggttat tgattctgtt gtagggaagg aggatgggct    180

aggtgtggag aacatacatg gaagtgctgc tattgccagt gcctattcta gggcctatga    240

ggagacattt acgcttacat ttgtgactgg aaggactgtt ggaataggag catatcttgc    300

tcgacttggc atacggtgca ttcagcgtac tgaccagccc attatcctaa ctgggttttc    360

tgccttgaac aagcttcttg gccgggaagt gtacagctcc cacatgcagt tgggtggccc    420

caaaattatg gccacaaacg gtgttgtcca tctgacagtt tcagatgacc ttgaaggtgt    480

atctaatata ttgaggtggc tcagctatgt tcctgccaac attggtggac ctcttcctat    540

tacaaaatct ttggacccac ctgacagacc cgttgcttac atccctgaga atacatgtga    600

tcctcgtgca gccatcagtg gcattgatga tagccaaggg aaatggttgg ggggcatgtt    660

cgacaaagac agttttgtgg agacatttga aggatgggcg aagtcagtag ttactggcag    720

agcgaaactc ggagggattc cggtgggtgt tatagctgtg gagacacaga ctatgatgca    780

gctcatccct gctgatccag gtcagcttga ttcccatgag cggtctgttc ctcgtgctgg    840

gcaagtctgg tttccagatt cagctactaa gacagcgcag gcaatgctgg acttcaaccg    900

tgaaggatta cctctgttca tccttgctaa ctggagaggc ttctctggtg ggcaaagaga    960

tctttttgaa ggaatccttc aggctgggtc aacaattgtt gagaacctta ggacatacaa   1020

tcagcctgcc tttgtatata tccccaaggc tgcagagcta cgtggagggg cttgggtcgt   1080

gattgatagc aagataaatc cagatcgcat tgagttctat gctgagagga ctgcaaaggg   1140

caatgttctg aacctcaagg g                                             1161


<210> SEQ ID NO 3
<211> LENGTH: 1129
<212> TYPE: DNA
<213> ORGANISM: Triticum aestivum

<400> SEQUENCE: 3

gtgttggatg gtctgatgat ggcagccctg aacgtgggtt tcagtacatt tatctgactg     60

aagaagacca tgctcgtatt agcacttctg ttatagcgca caagatgcag cttgataatg    120

gtgaaattag gtgggttatt gattctgttg tggggaagga ggatgggcta ggtgtggaga    180

acatacatgg aagtgctgct attgccagtg cctattctag ggcctatgag gagacattta    240

cgcttacatt tgtgactgga cggactgttg gaataggagc atatcttgct cgacttggca    300

tacggtgcat acagcgtact gaccagccca ttatcctaac cgggttctct gctttgaaca    360

agcttcttgg ccgggaagtg tacagctccc acatgcagtt gggtggcccc aaaattatgg    420

cgacaaacgg tgttgtccat ctgacagttt cagatgacct tgaaggtgtg tctaatatat    480

tgaggtggct cagctatgtt cctgccaaca ttggtggacc tcttcctatt acaaaatctt    540

tggacccacc tgacagaccc gttgcatata tccctgagaa tacatgtgat cctcgtgcag    600

ccatcagtgg cattgatgat agccaaggga aatggttggg ggcatgttc gacaaagaca     660

gttttgtgga gacatttgaa ggatgggcga agtcagtagt tactggcaga gcgaaactcg    720

gagggattcc ggtgggtgtt atagctgtgg agacacagac tatgatgcag ctcatccctg    780

ctgatccagg ccagcttgat tcccatgagc ggtctgttcc tcgtgctggg caagtctggt    840

ttccagattc agctactaag acagctcaag caatgctgga cttcaaccgt gaaggattac    900

ctctgttcat ccttgctaac tggagaggct tctctggtgg gcaaagagat ctttttgaag    960

gaatccttca ggctgggtca acaattgttg agaaccttag gacatacaat cagcctgcct   1020

ttgtatatat ccccaaggct gcagagctac gtggaggggc ttgggtcgtg attgatagca   1080
```

```
agataaatcc agatcgaatt gagttctatg ctgagaggac tgcaaaggg              1129


<210> SEQ ID NO 4
<211> LENGTH: 1188
<212> TYPE: DNA
<213> ORGANISM: Triticum aestivum

<400> SEQUENCE: 4

gatgaagtaa aatcgtgctt cgtgttggat ggtctgatga tggcagccct gaacgtgggt     60

ttcagtacat ttatctgact gaagaagacc atgctcgtat tagcacttct gttatagcgc    120

acaagatgca gcttgataat ggtgaaatta ggtgggttat tgattctgtt gtggggaagg    180

aggatgggct aggtgtggag aacatacatg gaagtgctgc tattgccagt gcctattcta    240

gggcctatga ggagacattt acgcttacat ttgtgactgg acggactgtt ggaataggag    300

catatcttgc tcgacttggc atacggtgca tacagcgtac tgaccagccc attatcctaa    360

ccgggttctc tgctttgaac aagcttcttg gccgggaagt gtacagctcc cacatgcagt    420

tgggtggccc caaaattatg gcgacaaacg gtgttgtcca tctgacagtt tcagatgacc    480

ttgaaggtgt gtctaatata ttgaggtggc tcagctatgt tcctgccaac attggtggac    540

ctcttcctat tacaaaatct ttggacccac ctgacagacc cgttgcatat atccctgaga    600

atacatgtga tcctcgtgca gccatcagtg gcattgatga tagccaaggg aaatggttgg    660

ggggcatgtt cgacaaagac agttttgtgg agacatttga aggatgggcg aagtcagtag    720

ttactggcag agcgaaactc ggagggattc cggtgggtgt tatagctgtg gagacacaga    780

ctatgatgca gctcatccct gctgatccag gccagcttga ttcccatgag cggtctgttc    840

ctcgtgctgg gcaagtctgg tttccagatt cagttactaa gacagctcaa gcaatgctgg    900

acttcaaccg tgaaggatta cctctgttca tccttgctaa ctggagaggc ttctctggtg    960

ggcaaagaga tctttttgaa ggaatccttc aggctgggtc aacaattgtt gagaacctta   1020

ggacatacaa tcagcctgcc tttgtatata tccccaaggc tgcagagcta cgtggagggg   1080

cttgggtcgt gattgatagc aagataaatc cagatcgaat tgagttctat gctgagagga   1140

ctgcaaaggg taatgttctt gaacctcaag ggttgattga gataccag               1188


<210> SEQ ID NO 5
<211> LENGTH: 1194
<212> TYPE: DNA
<213> ORGANISM: Triticum aestivum

<400> SEQUENCE: 5

ggcatagcag atgaagtaga gtcttgcttc cgtgttggat ggtctgatga tggcagccct     60

gaacgtgggt ttcagtacat ttatctgact gaagaagacc atgctcgtat tagcacttct    120

gttatagcgc acaagatgca gcttgataat ggtgaaatta ggtgggttat cgattctgtt    180

gtggggaagg aggatgggct aggtgtggag aacatacatg gaagtgctgc tattgccagt    240

gcctattcta gggcctatga ggagacattt acgcttacat ttgtgactgg acggactgtt    300

ggaataggag catatcttgc tcgacttggc atacggtgca tacagcgtac tgaccagccc    360

attatcctaa ctgggttctc tgccttgaac aagcttcttg gccgggaagt ttacagctcc    420

cacatgcagt tgggtggccc caaaattatg gcgacaaacg gtgttgtcca tctgacagtt    480

tcagatgacc ttgaaggtgt atctaatata ttgaggtggc tcagctatgt tcctgccaac    540

attggtggac ctcttcctat tacaaaatct ttggacccac ctgacagacc cgttgcttac    600
```

```
atccctgaga atacatgcga tcctcgtgct gccatcagtg gcattgatga tagccaaggg    660
aaatggttgg ggggcatgtt cgacaaagac agttttgtgg agacatttga aggatgggcg    720
aagtcagttg ttactggcag agctaaactc ggagggattc cggtgggtgt tatagctgtg    780
gagacacaga ctatgatgca gctcatccct gctgatccag gccagcttga ttcccatgag    840
cggtctgttc ctcgtgctgg gcaagtctgg tttccagatt cagttactaa gacagcgcag    900
gcaatgctgg acttcaaccg tgaaggatta cctctgttca tccttgctaa ctggagaggc    960
ttctctggtg gacaaagaga tctttttgaa ggaatccttc aggctgggtc aacaattgtt   1020
gagaacctta ggacatacaa tcagcctgcc tttgtatata tccccaaggc tgcagagcta   1080
cgtggagggg cttgggtcgt gattgatagc aagataaatc cagatcgcat tgagttctat   1140
gctgagagga ctgcaaaggg caatgttctc gaacctcaag ggttgattga gatg         1194
```

```
<210> SEQ ID NO 6
<211> LENGTH: 1184
<212> TYPE: DNA
<213> ORGANISM: Triticum aestivum

<400> SEQUENCE: 6

tgaagtaaaa tcttgcttcc gtgttggatg gtctgatgat ggcagccctg aacgtgggtt     60
tcaatatatt tatctgactg aagaagacca tgctcgtatt agcgcttctg ttatagcgca    120
caagatgcag cttgataatg gtgaaattag gtgggttatt gattctgttg tagggaagga    180
ggatgggcta ggtgtggaga acatacatgg aagtgctgct attgccagtg cctattctag    240
ggcctatgag gagacattta cgcttacatt tgtgactgga aggactgttg gaataggagc    300
atatcttgct cgacttggca tacggtgcat tcagcgtact gaccagccca ttatcctaac    360
tgggttttct gccttgaaca agcttcttgg ccgggaagtg tacagctccc acatgcagtt    420
gggtggcccc aaaattatgg ccacaaacgg tgttgtccat ctgacagttt cagatgacct    480
tgaaggtgta tctaatatat tgaggtggct cagctatgtt cctgccaaca ttggtggacc    540
tcttcctatt acaaaatctt tggacccacc tgacagaccc gttgcttaca tccctgagaa    600
tacatgtgat cctcgtgcag ccatcagtgg cattgatgat agccaaggga aatggttggg    660
gggcatgttc gacaaagaca gttttgtgga gacatttgaa ggatgggcga agtcagtagt    720
tactggcaga gcgaaactcg gagggattcc ggtgggtgtt atagctgtgg agacacagac    780
tatgatgcag ctcatccctg ctgatccagg tcagcttgat tcccatgagc ggtctgttcc    840
tcgtgctggg caagtctggt ttccagattc agttactaag acagcgcagg caatgctgga    900
cttcaaccgt gaaggattac ctctgttcat ccttgctaac tggagaggct tctctggtgg    960
gcaaagagat ctttttgaag gaatccttca ggctgggtca acaattgttg agaaccttag   1020
gacatacaat cagcctgcct ttgtatatat ccccaaggct gcagagctac gtggaggggc   1080
ttgggtcgtg attgatagca agataaatcc agatcgcatt gagttctatg ctgagaggac   1140
tgcaaagggc aatgttcttg aacctcaagg gttgattgag atgc                    1184
```

```
<210> SEQ ID NO 7
<211> LENGTH: 375
<212> TYPE: PRT
<213> ORGANISM: Triticum aestivum

<400> SEQUENCE: 7

Val Gly Trp Ser Asp Asp Gly Ser Pro Glu Arg Gly Phe Gln Tyr Ile
1               5                   10                  15
```

```
Tyr Leu Thr Glu Glu Asp His Ala Arg Ile Ser Thr Ser Val Ile Ala
            20                  25                  30

His Lys Met Gln Leu Asp Asn Gly Glu Ile Arg Trp Val Ile Asp Ser
        35                  40                  45

Val Val Gly Lys Glu Asp Gly Leu Gly Val Glu Asn Ile His Gly Ser
    50                  55                  60

Ala Ala Ile Ala Ser Ala Tyr Ser Arg Ala Tyr Glu Glu Thr Phe Thr
65                  70                  75                  80

Leu Thr Phe Val Thr Gly Arg Thr Val Gly Ile Gly Ala Tyr Leu Ala
                85                  90                  95

Arg Leu Gly Ile Arg Cys Ile Gln Arg Thr Asp Gln Pro Ile Ile Leu
            100                 105                 110

Thr Gly Phe Ser Ala Leu Asn Lys Leu Leu Gly Arg Glu Val Tyr Ser
        115                 120                 125

Ser His Met Gln Leu Gly Gly Pro Lys Ile Met Ala Thr Asn Gly Val
    130                 135                 140

Val His Leu Thr Val Ser Asp Asp Leu Glu Gly Val Ser Asn Ile Leu
145                 150                 155                 160

Arg Trp Leu Ser Tyr Val Pro Ala Asn Ile Gly Gly Pro Leu Pro Ile
                165                 170                 175

Thr Lys Ser Leu Asp Pro Pro Asp Arg Pro Val Ala Tyr Ile Pro Glu
            180                 185                 190

Asn Thr Cys Asp Pro Arg Ala Ala Ile Ser Gly Ile Asp Asp Ser Gln
        195                 200                 205

Gly Lys Trp Leu Gly Gly Met Phe Asp Lys Asp Ser Phe Val Glu Thr
    210                 215                 220

Phe Glu Gly Trp Ala Lys Ser Val Val Thr Gly Arg Ala Lys Leu Gly
225                 230                 235                 240

Gly Ile Pro Val Gly Val Ile Ala Val Glu Thr Gln Thr Met Met Gln
                245                 250                 255

Leu Ile Pro Ala Asp Pro Gly Gln Leu Asp Ser His Glu Arg Ser Val
            260                 265                 270

Pro Arg Ala Gly Gln Val Trp Phe Pro Asp Ser Ala Thr Lys Thr Ala
        275                 280                 285

Gln Ala Met Leu Asp Phe Asn Arg Glu Gly Leu Pro Leu Phe Ile Leu
    290                 295                 300

Ala Asn Trp Arg Gly Phe Ser Gly Gly Gln Arg Asp Leu Phe Glu Gly
305                 310                 315                 320

Ile Leu Gln Ala Gly Ser Thr Ile Val Glu Asn Leu Arg Thr Tyr Asn
                325                 330                 335

Gln Pro Ala Phe Val Tyr Ile Pro Lys Ala Ala Glu Leu Arg Gly Gly
            340                 345                 350

Ala Trp Val Val Ile Asp Ser Lys Ile Asn Pro Asp Arg Ile Glu Phe
        355                 360                 365

Tyr Ala Glu Arg Thr Ala Lys
    370                 375
```

<210> SEQ ID NO 8
<211> LENGTH: 394
<212> TYPE: PRT
<213> ORGANISM: Triticum aestivum

<400> SEQUENCE: 8

```
Ser Lys Ile Val Leu Arg Val Gly Trp Ser Asp Asp Gly Ser Pro Glu
1               5                   10                  15
```

```
Arg Gly Phe Gln Tyr Ile Tyr Leu Thr Glu Glu Asp His Ala Arg Ile
            20                  25                  30

Ser Thr Ser Val Ile Ala His Lys Met Gln Leu Asp Asn Gly Glu Ile
        35                  40                  45

Arg Trp Val Ile Asp Ser Val Val Gly Lys Glu Asp Gly Leu Gly Val
    50                  55                  60

Glu Asn Ile His Gly Ser Ala Ala Ile Ala Ser Ala Tyr Ser Arg Ala
65                  70                  75                  80

Tyr Glu Glu Thr Phe Thr Leu Thr Phe Val Thr Gly Arg Thr Val Gly
                85                  90                  95

Ile Gly Ala Tyr Leu Ala Arg Leu Gly Ile Arg Cys Ile Gln Arg Thr
            100                 105                 110

Asp Gln Pro Ile Ile Leu Thr Gly Phe Ser Ala Leu Asn Lys Leu Leu
        115                 120                 125

Gly Arg Glu Val Tyr Ser Ser His Met Gln Leu Gly Gly Pro Lys Ile
    130                 135                 140

Met Ala Thr Asn Gly Val Val His Leu Thr Val Ser Asp Asp Leu Glu
145                 150                 155                 160

Gly Val Ser Asn Ile Leu Arg Trp Leu Ser Tyr Val Pro Ala Asn Ile
                165                 170                 175

Gly Gly Pro Leu Pro Ile Thr Lys Ser Leu Asp Pro Pro Asp Arg Pro
            180                 185                 190

Val Ala Tyr Ile Pro Glu Asn Thr Cys Asp Pro Arg Ala Ala Ile Ser
        195                 200                 205

Gly Ile Asp Asp Ser Gln Gly Lys Trp Leu Gly Gly Met Phe Asp Lys
    210                 215                 220

Asp Ser Phe Val Glu Thr Phe Glu Gly Trp Ala Lys Ser Val Val Thr
225                 230                 235                 240

Gly Arg Ala Lys Leu Gly Gly Ile Pro Val Gly Val Ile Ala Val Glu
                245                 250                 255

Thr Gln Thr Met Met Gln Leu Ile Pro Ala Asp Pro Gly Gln Leu Asp
            260                 265                 270

Ser His Glu Arg Ser Val Pro Arg Ala Gly Gln Val Trp Phe Pro Asp
        275                 280                 285

Ser Val Thr Lys Thr Ala Gln Ala Met Leu Asp Phe Asn Arg Glu Gly
    290                 295                 300

Leu Pro Leu Phe Ile Leu Ala Asn Trp Arg Gly Phe Ser Gly Gly Gln
305                 310                 315                 320

Arg Asp Leu Phe Glu Gly Ile Leu Gln Ala Gly Ser Thr Ile Val Glu
                325                 330                 335

Asn Leu Arg Thr Tyr Asn Gln Pro Ala Phe Val Tyr Ile Pro Lys Ala
            340                 345                 350

Ala Glu Leu Arg Gly Gly Ala Trp Val Val Ile Asp Ser Lys Ile Asn
        355                 360                 365

Pro Asp Arg Ile Glu Phe Tyr Ala Glu Arg Thr Ala Lys Gly Asn Val
    370                 375                 380

Leu Glu Pro Gln Gly Leu Ile Glu Ile Pro
385                 390
```

<210> SEQ ID NO 9
<211> LENGTH: 384
<212> TYPE: PRT
<213> ORGANISM: Triticum aestivum

<400> SEQUENCE: 9

```
Arg Val Gly Trp Ser Asp Asp Gly Ser Pro Glu Arg Gly Phe Gln Tyr
1               5                   10                  15

Ile Tyr Leu Thr Glu Glu Asp His Ala Arg Ile Ser Thr Ser Val Ile
            20                  25                  30

Ala His Lys Met Gln Leu Asp Asn Gly Glu Ile Arg Trp Val Ile Asp
        35                  40                  45

Ser Val Val Gly Lys Glu Asp Gly Leu Gly Val Glu Asn Ile His Gly
    50                  55                  60

Ser Ala Ala Ile Ala Ser Ala Tyr Ser Arg Ala Tyr Glu Glu Thr Phe
65                  70                  75                  80

Thr Leu Thr Phe Val Thr Gly Arg Thr Val Gly Ile Gly Ala Tyr Leu
                85                  90                  95

Ala Arg Leu Gly Ile Arg Cys Ile Gln Arg Thr Asp Gln Pro Ile Ile
            100                 105                 110

Leu Thr Gly Phe Ser Ala Leu Asn Lys Leu Leu Gly Arg Glu Val Tyr
        115                 120                 125

Ser Ser His Met Gln Leu Gly Gly Pro Lys Ile Met Ala Thr Asn Gly
    130                 135                 140

Val Val His Leu Thr Val Ser Asp Asp Leu Glu Gly Val Ser Asn Ile
145                 150                 155                 160

Leu Arg Trp Leu Ser Tyr Val Pro Ala Asn Ile Gly Gly Pro Leu Pro
                165                 170                 175

Ile Thr Lys Ser Leu Asp Pro Pro Asp Arg Pro Val Ala Tyr Ile Pro
            180                 185                 190

Glu Asn Thr Cys Asp Pro Arg Ala Ala Ile Ser Gly Ile Asp Asp Ser
        195                 200                 205

Gln Gly Lys Trp Leu Gly Gly Met Phe Asp Lys Asp Ser Phe Val Glu
    210                 215                 220

Thr Phe Glu Gly Trp Ala Lys Ser Val Val Thr Gly Arg Ala Lys Leu
225                 230                 235                 240

Gly Gly Ile Pro Val Gly Val Ile Ala Val Glu Thr Gln Thr Met Met
                245                 250                 255

Gln Leu Ile Pro Ala Asp Pro Gly Gln Leu Asp Ser His Glu Arg Ser
            260                 265                 270

Val Pro Arg Ala Gly Gln Val Trp Phe Pro Asp Ser Ala Thr Lys Thr
        275                 280                 285

Ala Gln Ala Met Leu Asp Phe Asn Arg Glu Gly Leu Pro Leu Phe Ile
    290                 295                 300

Leu Ala Asn Trp Arg Gly Phe Ser Gly Gly Gln Arg Asp Leu Phe Glu
305                 310                 315                 320

Gly Ile Leu Gln Ala Gly Ser Thr Ile Val Glu Asn Leu Arg Thr Tyr
                325                 330                 335

Asn Gln Pro Ala Phe Val Tyr Ile Pro Lys Ala Ala Glu Leu Arg Gly
            340                 345                 350

Gly Ala Trp Val Val Ile Asp Ser Lys Ile Asn Pro Asp Arg Ile Glu
        355                 360                 365

Phe Tyr Ala Glu Arg Thr Ala Lys Gly Asn Val Leu Glu Pro Gln Gly
    370                 375                 380
```

<210> SEQ ID NO 10
<211> LENGTH: 398
<212> TYPE: PRT
<213> ORGANISM: Triticum aestivum

<400> SEQUENCE: 10

```
Gly Ile Ala Asp Glu Val Glu Ser Cys Phe Arg Val Gly Trp Ser Asp
1               5                   10                  15

Asp Gly Ser Pro Glu Arg Gly Phe Gln Tyr Ile Tyr Leu Thr Glu Glu
            20                  25                  30

Asp His Ala Arg Ile Ser Thr Ser Val Ile Ala His Lys Met Gln Leu
        35                  40                  45

Asp Asn Gly Glu Ile Arg Trp Val Ile Asp Ser Val Val Gly Lys Glu
    50                  55                  60

Asp Gly Leu Gly Val Glu Asn Ile His Gly Ser Ala Ala Ile Ala Ser
65                  70                  75                  80

Ala Tyr Ser Arg Ala Tyr Glu Glu Thr Phe Thr Leu Thr Phe Val Thr
                85                  90                  95

Gly Arg Thr Val Gly Ile Gly Ala Tyr Leu Ala Arg Leu Gly Ile Arg
            100                 105                 110

Cys Ile Gln Arg Thr Asp Gln Pro Ile Ile Leu Thr Gly Phe Ser Ala
        115                 120                 125

Leu Asn Lys Leu Leu Gly Arg Glu Val Tyr Ser Ser His Met Gln Leu
    130                 135                 140

Gly Gly Pro Lys Ile Met Ala Thr Asn Gly Val Val His Leu Thr Val
145                 150                 155                 160

Ser Asp Asp Leu Glu Gly Val Ser Asn Ile Leu Arg Trp Leu Ser Tyr
                165                 170                 175

Val Pro Ala Asn Ile Gly Gly Pro Leu Pro Ile Thr Lys Ser Leu Asp
            180                 185                 190

Pro Pro Asp Arg Pro Val Ala Tyr Ile Pro Glu Asn Thr Cys Asp Pro
        195                 200                 205

Arg Ala Ala Ile Ser Gly Ile Asp Asp Ser Gln Gly Lys Trp Leu Gly
    210                 215                 220

Gly Met Phe Asp Lys Asp Ser Phe Val Glu Thr Phe Glu Gly Trp Ala
225                 230                 235                 240

Lys Ser Val Val Thr Gly Arg Ala Lys Leu Gly Gly Ile Pro Val Gly
                245                 250                 255

Val Ile Ala Val Glu Thr Gln Thr Met Met Gln Leu Ile Pro Ala Asp
            260                 265                 270

Pro Gly Gln Leu Asp Ser His Glu Arg Ser Val Pro Arg Ala Gly Gln
        275                 280                 285

Val Trp Phe Pro Asp Ser Val Thr Lys Thr Ala Gln Ala Met Leu Asp
    290                 295                 300

Phe Asn Arg Glu Gly Leu Pro Leu Phe Ile Leu Ala Asn Trp Arg Gly
305                 310                 315                 320

Phe Ser Gly Gly Gln Arg Asp Leu Phe Glu Gly Ile Leu Gln Ala Gly
                325                 330                 335

Ser Thr Ile Val Glu Asn Leu Arg Thr Tyr Asn Gln Pro Ala Phe Val
            340                 345                 350

Tyr Ile Pro Lys Ala Ala Glu Leu Arg Gly Gly Ala Trp Val Val Ile
        355                 360                 365

Asp Ser Lys Ile Asn Pro Asp Arg Ile Glu Phe Tyr Ala Glu Arg Thr
    370                 375                 380

Ala Lys Gly Asn Val Leu Glu Pro Gln Gly Leu Ile Glu Met
385                 390                 395
```

```
<210> SEQ ID NO 11
<211> LENGTH: 386
<212> TYPE: PRT
<213> ORGANISM: Triticum aestivum

<400> SEQUENCE: 11

Ser Cys Phe Arg Val Gly Trp Ser Asp Asp Gly Ser Pro Glu Arg Gly
1               5                   10                  15

Phe Gln Tyr Ile Tyr Leu Thr Glu Glu Asp His Ala Arg Ile Ser Ala
            20                  25                  30

Ser Val Ile Ala His Lys Met Gln Leu Asp Asn Gly Glu Ile Arg Trp
        35                  40                  45

Val Ile Asp Ser Val Val Gly Lys Glu Asp Gly Leu Gly Val Glu Asn
    50                  55                  60

Ile His Gly Ser Ala Ala Ile Ala Ser Ala Tyr Ser Arg Ala Tyr Glu
65                  70                  75                  80

Glu Thr Phe Thr Leu Thr Phe Val Thr Gly Arg Thr Val Gly Ile Gly
                85                  90                  95

Ala Tyr Leu Ala Arg Leu Gly Ile Arg Cys Ile Gln Arg Thr Asp Gln
            100                 105                 110

Pro Ile Ile Leu Thr Gly Phe Ser Ala Leu Asn Lys Leu Leu Gly Arg
        115                 120                 125

Glu Val Tyr Ser Ser His Met Gln Leu Gly Gly Pro Lys Ile Met Ala
    130                 135                 140

Thr Asn Gly Val Val His Leu Thr Val Ser Asp Asp Leu Glu Gly Val
145                 150                 155                 160

Ser Asn Ile Leu Arg Trp Leu Ser Tyr Val Pro Ala Asn Ile Gly Gly
                165                 170                 175

Pro Leu Pro Ile Thr Lys Ser Leu Asp Pro Pro Asp Arg Pro Val Ala
            180                 185                 190

Tyr Ile Pro Glu Asn Thr Cys Asp Pro Arg Ala Ala Ile Ser Gly Ile
        195                 200                 205

Asp Asp Ser Gln Gly Lys Trp Leu Gly Gly Met Phe Asp Lys Asp Ser
    210                 215                 220

Phe Val Glu Thr Phe Glu Gly Trp Ala Lys Ser Val Val Thr Gly Arg
225                 230                 235                 240

Ala Lys Leu Gly Gly Ile Pro Val Gly Val Ile Ala Val Glu Thr Gln
                245                 250                 255

Thr Met Met Gln Leu Ile Pro Ala Asp Pro Gly Gln Leu Asp Ser His
            260                 265                 270

Glu Arg Ser Val Pro Arg Ala Gly Gln Val Trp Phe Pro Asp Ser Ala
        275                 280                 285

Thr Lys Thr Ala Gln Ala Met Leu Asp Phe Asn Arg Glu Gly Leu Pro
    290                 295                 300

Leu Phe Ile Leu Ala Asn Trp Arg Gly Phe Ser Gly Gly Gln Arg Asp
305                 310                 315                 320

Leu Phe Glu Gly Ile Leu Gln Ala Gly Ser Thr Ile Val Glu Asn Leu
                325                 330                 335

Arg Thr Tyr Asn Gln Pro Ala Phe Val Tyr Ile Pro Lys Ala Ala Glu
            340                 345                 350

Leu Arg Gly Gly Ala Trp Val Val Ile Asp Ser Lys Ile Asn Pro Asp
        355                 360                 365

Arg Ile Glu Phe Tyr Ala Glu Arg Thr Ala Lys Gly Asn Val Leu Asn
    370                 375                 380
```

```
Leu Lys
385


<210> SEQ ID NO 12
<211> LENGTH: 394
<212> TYPE: PRT
<213> ORGANISM: Triticum aestivum

<400> SEQUENCE: 12

Glu Val Lys Ser Cys Phe Arg Val Gly Trp Ser Asp Asp Gly Ser Pro
1               5                   10                  15

Glu Arg Gly Phe Gln Tyr Ile Tyr Leu Thr Glu Glu Asp His Ala Arg
            20                  25                  30

Ile Ser Ala Ser Val Ile Ala His Lys Met Gln Leu Asp Asn Gly Glu
        35                  40                  45

Ile Arg Trp Val Ile Asp Ser Val Val Gly Lys Glu Asp Gly Leu Gly
    50                  55                  60

Val Glu Asn Ile His Gly Ser Ala Ala Ile Ala Ser Ala Tyr Ser Arg
65                  70                  75                  80

Ala Tyr Glu Glu Thr Phe Thr Leu Thr Phe Val Thr Gly Arg Thr Val
                85                  90                  95

Gly Ile Gly Ala Tyr Leu Ala Arg Leu Gly Ile Arg Cys Ile Gln Arg
            100                 105                 110

Thr Asp Gln Pro Ile Ile Leu Thr Gly Phe Ser Ala Leu Asn Lys Leu
        115                 120                 125

Leu Gly Arg Glu Val Tyr Ser Ser His Met Gln Leu Gly Gly Pro Lys
    130                 135                 140

Ile Met Ala Thr Asn Gly Val Val His Leu Thr Val Ser Asp Asp Leu
145                 150                 155                 160

Glu Gly Val Ser Asn Ile Leu Arg Trp Leu Ser Tyr Val Pro Ala Asn
                165                 170                 175

Ile Gly Gly Pro Leu Pro Ile Thr Lys Ser Leu Asp Pro Pro Asp Arg
            180                 185                 190

Pro Val Ala Tyr Ile Pro Glu Asn Thr Cys Asp Pro Arg Ala Ala Ile
        195                 200                 205

Ser Gly Ile Asp Asp Ser Gln Gly Lys Trp Leu Gly Gly Met Phe Asp
    210                 215                 220

Lys Asp Ser Phe Val Glu Thr Phe Glu Gly Trp Ala Lys Ser Val Val
225                 230                 235                 240

Thr Gly Arg Ala Lys Leu Gly Gly Ile Pro Val Gly Val Ile Ala Val
                245                 250                 255

Glu Thr Gln Thr Met Met Gln Leu Ile Pro Ala Asp Pro Gly Gln Leu
            260                 265                 270

Asp Ser His Glu Arg Ser Val Pro Arg Ala Gly Gln Val Trp Phe Pro
        275                 280                 285

Asp Ser Val Thr Lys Thr Ala Gln Ala Met Leu Asp Phe Asn Arg Glu
    290                 295                 300

Gly Leu Pro Leu Phe Ile Leu Ala Asn Trp Arg Gly Phe Ser Gly Gly
305                 310                 315                 320

Gln Arg Asp Leu Phe Glu Gly Ile Leu Gln Ala Gly Ser Thr Ile Val
                325                 330                 335

Glu Asn Leu Arg Thr Tyr Asn Gln Pro Ala Phe Val Tyr Ile Pro Lys
            340                 345                 350

Ala Ala Glu Leu Arg Gly Gly Ala Trp Val Val Ile Asp Ser Lys Ile
        355                 360                 365
```

```
Asn Pro Asp Arg Ile Glu Phe Tyr Ala Glu Arg Thr Ala Lys Gly Asn
    370                 375                 380

Val Leu Glu Pro Gln Gly Leu Ile Glu Met
385                 390


<210> SEQ ID NO 13
<211> LENGTH: 12753
<212> TYPE: DNA
<213> ORGANISM: Alopecurus myosuroides

<400> SEQUENCE: 13

tcagtttatg gcagtctgtg tttgaagaac actgcaactc cgctgtctgt ccaaagggag      60

gacgatggga tccacacatc tgcccattgt cgggtttaat gcatccacaa caccatcgct     120

atccactctt cgccagataa actcagctgc tgctgcattc caatcttcgt ccccttcaag     180

gtcatccaag aagaaaagcc gacgtgttaa gtcaataagg gatgatggcg atggaagcgt     240

gccagaccct gcaggccatg gccagtctat tcgccaaggt gaacccagga ccatctcctt     300

actttttgt cgtcaacctc agacttgcat agatttactt tcttgattga gagcatgctt      360

gttttagtgt aagatatctc aatactgtat cacaaaatga tagttaagaa caaaccacta     420

caccaatctt cacatattgt tcttattggg tttgctaaat cttagttcgc attagatttt     480

tttatgtcta tgtcgacacc ctgagcctcc ccgtgtctct gcattgagat tcaagcaggg     540

ataggggaaa tcacgactgg atccttagcc ataattaaat ctctgtcaac ttaggtgtag     600

atggactctg tttttaatat tcagtatgat gttttcttaa gggagaggga cacaaaaata     660

catgtatgtt gcagtttaag aatttatgac tgaatgtttt gatgatataa tagttctgga     720

aaagaaggat gcctagattt tgtatttttg ataaatgtag ttataaaatt cgaaaggttg     780

gcaaaccatt gcttcttctt agctattgtg ttggcttgct cagtttccaa tgcatatctg     840

gatgtaggtc tcgctggcat catcgacctc ccaaaggagg gcgcatcagc tccagatgtg     900

gacatttcac agtaagtacc tcagcacact cacattatag cttagtcctc ttgaaagaac     960

aggcaaaaat gtataacgca tgtataattc ctagatttca cttgtcttat tatcgttacg    1020

ctgaaatgtt gaagttgtaa attcgttatt ctcatagatt tacacctcta tgtacatcat    1080

agttatgcac tatgcacctg ctgtgagttc tggaaattga accattcagc gcactgcaat    1140

ctgtaaggtt ttgtttttat ataatatggt tataaatcat gttcaacctc tgcatctaca    1200

acattattta tgtgtggtat agtatatagt aatgttacag ggtgagattt tgctatataa    1260

gttatgaaac ttgtgtttaa ctttgtaaag ggaaacatcc tcaaacctgt tcttagtggt    1320

tacagcccag gcacatggcc gttgcactgt atggagtatt gttgggcact tacagaacat    1380

tttattggaa agactttttc atataagtat tgtttaaatt taattgccaa ctgaaaccct    1440

tacccggata acaagatgaa taacccactt gcgtttttga ttcatactag gcattactat    1500

gtcatatgta ttacggtgac cgcagtaata actttgctct ttcttttcta gtgggtctga    1560

agaccacaag gcctcctacc aaatgaatgg gatactgaat gaatcacata acgggaggca    1620

cgcctctctg tctaaagttt atgaattttg cacggaattg ggtggaaaaa caccaattca    1680

cagtgtatta gtcgccaaca atggaatggc agcagctaag ttcatgcgga gtgtccggac    1740

atgggctaat gatacatttg ggtcagagaa ggcgattcag ttgatagcta tggcaactcc    1800

ggaagacatg agaataaatg cagagcacat tagaattgct gatcagtttg ttgaagtacc    1860

tggtggaaca aacaataaca actatgcaaa tgtccaactc atagtggagg tcagtactgg    1920
```

```
tcatcccttg atgtgcagtt atgcacaagc tcctctttgg tctttagcat gacatggcaa   1980
cttcactttt gcagatagca gagagaactg gtgtctccgc cgtttggcct ggttggggcc   2040
atgcatctga gaatcctgaa cttccagatg cactaactgc aaaaggaatt gtttttcttg   2100
ggccaccagc atcatcaatg aacgcactag gcgacaaggt tggttcagct ctcattgctc   2160
aagcagcagg ggttcccact cttgcttgga gtggatcaca tgtaagcctc acattctctc   2220
tgataaatca tcacctgata tttatggtgg atgcattatg taacctatga catttttatt   2280
ctaggtggaa attccattag aactttgttt ggactcgata cctgaggaga tgtataggaa   2340
agcctgtgtt acaaccgctg atgaagcagt tgcaagttgt cagatgattg gttaccctgc   2400
catgatcaag gcatcctggg gtggtggtgg taaagggatt agaaaggtac attattcatt   2460
tgattggact gtacacaaga gattgtgtgg gctgtgatat tttgtgcaca gtgttagccc   2520
taaccttttt aacatattaa ctcgatatct cttgcaggtt aataatgatg acgaggtgaa   2580
agcactgttt aagcaagtac agggtgaagt tcctggctcc ccgatattta tcatgagact   2640
tgcatctcag gttagacttc tctggaagtt ctattttcca agcgtgctgt atctgggttg   2700
tatattgtac gtatggaagc tttatttgct ctttcttaca ggctaaaatt gtatcctgta   2760
atctgtacta atattgtaat tttcatttaa atccctctcc cctttccttt tgtagagtcg   2820
tcatcttgaa gtccagctgc tttgtgatga atatggcaat gtagcagcac ttcacagtcg   2880
tgattgcagt gtgcaacgac gacaccaaaa ggtatgctgc tccaaactga aatcatcact   2940
tttatttcgg ttctgcttta cgtgtagttt tgatcaaatg gttcaactgt gtccattttg   3000
tttgtttata acagattatc gaggaaggac cagttactgt tgctcctcgt gaaacagtga   3060
aagagctaga gcaagcagca aggaggcttg ctaaggccgt gggttacgtc ggtgctgcta   3120
ctgttgaata tctctacagc atggagactg gtgaatacta ttttctggag cttaatccac   3180
ggttgcaggt ttgttctttt ggacactctc caggacttct attttgttgg cagtcgttta   3240
cattgttaaa tggtctatat tcaggttgag cacccagtca ccgagtcgat agctgaagta   3300
aatttgcctg cagcccaagt tgcagttggg atgggtatac ccctttggca gattccaggt   3360
aataataata tcattgtaaa gagtttcgtt tctgtcccat gttctttctg tctaactatc   3420
tccttattca gagatcagac gtttctacgg aatggacaat ggaggaggct atgatatttg   3480
gaggaaaaca gcagctctcg ctactccatt caactttgat gaagtagatt ctcaatggcc   3540
gaagggtcat tgtgtggcag ttaggataac cagtgagaat ccagatgatg gattcaagcc   3600
tactggtgga aaagtaaagg tgggatttcc taatgttata tctatgtttc aattacacta   3660
cggttagtaa actgatctga tcttgatttt tttcgtatat ttcaggagat aagttttaaa   3720
agtaagccaa atgtctgggg atatttctca gttaaggtaa gctgttcata gctctgttgc   3780
agggtcatct tgttttgagt tccgcagaag attagtctgc aagattttta ttcgaattag   3840
tattctcatt ttggtttttg actaagtatt gatccaatca acaaatattg tctctccctt   3900
catctgtttt cagtctggtg gaggcattca tgaatttgcg gattctcagt ttggtatgta   3960
aaatgtaacg taatgaatat tcctctttgc tattcgtact gatccttaca ttggaattgc   4020
tcctttcatt acaggacacg tttttgccta tggagagact agatcagcag caataaccag   4080
catgtctctt gcactaaaag agattcaaat tcgtggagaa attcatacaa acgttgatta   4140
cacggttgat ctcttgaatg taagtaacaa taacaatttg ttgaatccta cttttgatgt   4200
gatacaacca ttttacatcc ggctttcctt caaaataatc ccattctgtg gtttctcgta   4260
tctttaattc aggccccaga cttcagagaa aacacgatcc ataccggttg gctggatacc   4320
```

```
agaatagcta tgcgtgttca agctgagagg cctccctggt atatttcagt ggttggagga   4380
gctctatatg taagatatga aactatgtta atgttactgc aacttttggc aagccaatct   4440
tgaaaaacac tagtgtttaa ttgaaataat tgttttgtgc tgtagaaaac aataaccacc   4500
aatgcggaga ccgtttctga atatgttagc tatctcatca agggtcagat tccaccaaag   4560
gtagtgtctt aatgggctta aactctgtat attgcttgaa ggtggacatt gctgaccagt   4620
gtttttgtgc agcacatatc ccttgtccat tcaactattt ctttgaatat agaggaaagc   4680
aaatatacag taagtgtgac attccttaaa aaaagactct cagttacaat gaaatgatac   4740
ttacactgat gctcatctac accatgccac agattgagat tgtgaggagt ggacagggta   4800
gctacagatt gagactgaat ggatcactta ttgaagccaa tgtacaaaca ttatgtgatg   4860
gaggcctttt aatgcaggta ccttctttct tttacttgct cataaatgtg atataatgtc   4920
tgctgaaata gttctgattc tttagttgta atgtctccag ctggatggaa atagccatgt   4980
tatttatgct gaagaagaag cgggtggtac acggcttctt attgatggaa aaacatgctt   5040
gctacaggta agaatattct gtttgtttgc tcctttataa tcttagtgtt tgatggtagg   5100
actttatatt cttatttgtg actttttaga gcatccacaa cccaaagcgc ttaggtagac   5160
gcttaaatac aaaaaaataa atacttaaaa agagtaaaac ggataagagt tgctacctgc   5220
aacgcccggc gcttaatctg aggcgcttaa tccggtatag ctacaggccg tcgctgcctt   5280
tttgctgcaa aaagaaaggg taagcgtcag gcgcatactt tggcgtcgat gtcatcccga   5340
cgctaggatt tgtgggcata accgtcgggt tggccaggat tttcttccta gcatcggagg   5400
ctaagcgccc cgttgtggct gctcttactg cattcacctc ttgaccatta gcacttcatt   5460
ttttacactt catctgtatt gcttctgctg tttctcaatt atagttattc caatgaccac   5520
tctttagtaa ttttaacaat tgccaattta tcataatacg gggcaaaaaa gtaggcgtcc   5580
ttaacaccat gtcatgtaac ctataataag cttgtgataa aatcatttgt gatacaatag   5640
aacagttgaa tactttatga tttctttctt acatgaatac tttatgattc ttgatgacgc   5700
tgcactgtat cctaagctac ataaattaca aatcgttttg cagaatgacc atgatccgtc   5760
aaggttatta gctgagacac cctgcaaact tcttcgtttc ttgattgccg atggtgctca   5820
tgttgatgct gatgtaccat acgcggaagt tgaggttatg aagatgtgca tgcccctctt   5880
gtcgcctgct gctggtgtca ttaatgtttt gttgtctgag ggccaggcga tgcaggttat   5940
attactgccc ttttgttgct tctgctgtta aaagccattg catgcgaagc atctgaactt   6000
aatatatttt gtttcaggct ggtgatctta tagcgagact tgatctcgat gacccttctg   6060
ctgtgaagag agccgagcca tttgaaggat cttttccaga aatgagcctt cctattgctg   6120
cttctggcca agttcacaaa agatgtgctg caagtttgaa cgctgctcga atggtccttg   6180
caggatatga ccatgcggcc aacaaagtaa acatcaagac attttatctc atgtttcctg   6240
cttttctcaa ataccattct ttaatagtat gaattctgga ttattctgac ttattggcat   6300
tttctgcctt ttgctaccaa atggtttcta atctatagaa gttcttgagc ttgtctttgc   6360
aaatcttgat ttaatgcttt tcttgtatgt tcatcatact catttatgat aggttgcatt   6420
tatccttctg ctattttcct ttctctcagt aaatcatgat ggatgctctt tctgttatgt   6480
tcatcatgct gtctattatc cttgtgctat ttttctattt ccagtagtgg atgtattggt   6540
ttaataattc ctgatcaaac tttgtatttt gttgttattt atacttggct cccttttcag   6600
gttgtgcaag atttggtatg gtgccttgat acacctgctc ttcctttcct acaatgggaa   6660
```

```
gagcttatgt ctgttttagc aactagactt ccaagacgtc ttaagagcga ggtatgtgat   6720
aattgatatg atatgcagaa tcaggcataa agggacattg atacatttaa tttatgatat   6780
agaagggtct tcatcctcga ttaaaagatc aattcactta tcatgattta cattctacat   6840
tgttgaatca ccttggtaat ttgccgtaac ttattgggca actattagct tttctaataa   6900
cgtaatcaaa attcagaata ttttacttca attcttcgta acatggaaca tttggtactt   6960
cgtctcattt atttgcactg tacgctgttt tagttggttt gccattctaa ctgaatcttt   7020
aaagttctta cttatttggt tttaacccag atcttgttta tttatctttt ataactttct   7080
tatgttctgc ctcaacggtt tatacttttt atgcatccag ttggagggca aatacaatga   7140
atacaagtta aatgttgacc atgtgaagat caaggatttc cctaccgaga tgcttagaga   7200
gacaatcgag gtcagttttt gtttcttatg gcaccccagt ctaaattata ctatttttg    7260
taacaagttt tcttttagga aaatcttgca tgtgtttccg agaaggaaat ggtgacaatt   7320
gagaggcttg ttgaccctct gatgagcctg ctgaagtcat acgagggtgg gagagaaagc   7380
catgcccact ttattgtcaa gtccctttt gaggagtatc tctcggttga ggaactattc    7440
agtgatggca ttcaggttat ctaacacttc taaactgagc agatctacta gagtcatttt   7500
ctaagggtca taattttcca gaacctcttg ggtgattaag tagcaaaaat aatttgtaca   7560
cgacttacga cttgcttcct tcgaaacact tttcactcat tattttcctc aaaatgtgcc   7620
attttgtagt ctgacgtgat tgaacgcctg cgcctacaat atagtaaaga cctccagaag   7680
gttgtagaca ttgttttgtc tcaccaggta aactactttt tggcctaatg acttggtgca   7740
aatgatcaca gaaacaatct ttgttactga tagtttgatt tgttctaggg tgtgagaaac   7800
aaaacaaagc tgatactcgc gctcatggag aaactggtct atccaaaccc tgctgcctac   7860
agagatcagt tgattcgctt ttcttccctc aaccataaaa gatattataa ggtgacaatg   7920
gcgacctaaa gtaatggaag ctttttgatt aatttgttgt gatattttag gctaatgaat   7980
tactttcatt gtaattatgc agttggctct taaagctagt gaacttcttg aacaaaccaa   8040
gctcagcgaa ctccgcacaa gcattgcaag gaacctttca gcgctggata tgttcaccga   8100
ggaaaaggca gatttctcct tgcaagacag aaaattggcc attaatgaga gcatgggaga   8160
tttagtcact gccccactgc cagttgaaga tgcacttgtt tctttgtttg attgtactga   8220
tcaaactctt cagcagagag tgattgagac atacatatct cgattatacc aggtattaca   8280
tgagctattt ttttctggat tttattatac tctctctcag catttctgga agcataaact   8340
aaggttccta atgaaataag atactcagtg tttcattaag ataaatccta gataatctag   8400
gcgtgggaag atttgattta gaacttgtag gcatgttact gctctgtaag ttggctaact   8460
tgccaatgat attttcagcc tcaacttgtg aaggatagca tccagctgaa atatcaggat   8520
tctggtgtta ttgctttatg ggaattcact gaaggaaatc atgagaagag attgggtgct   8580
atggttatcc tgaagtcact agaatctgtg tcaacagcca ttggagctgc tctaaaggat   8640
gcatcacatt atgcaagctc tgcgggcaac acggtgcata ttgctttgtt ggatgctgat   8700
acccaactga atacaactga agataggtat gttcatgtgc agtattagtg cagatgagtt   8760
tatttggtgc aaaaataagt taatctattt ctttcagtgg tgataatgac caagctcaag   8820
acaagatgga taaactttct tttgtactga aacaagatgt tgtcatggct gatctacgtg   8880
ctgctgatgt caaggttgtt agttgcattg ttcaaagaga tggagcaatc atgcctatgc   8940
gccgtacctt cctcttgtca gaggaaaaac tttgttacga ggaagagccg attcttcggc   9000
atgtggagcc tccactttct gcacttcttg agttggtatg caactccatc aaactgacta   9060
```

```
cgtgctgttt tgatatattt taatgctttc attttgttat ttgctacttg tattcactta   9120
gcttgctgtg gatacaggat aaattgaaag tgaaaggata caatgagatg aagtatacac   9180
cgtcacgtga tcgtcagtgg catatataca cacttagaaa tactgaaaat ccaaaaatgc   9240
tgcacagggt atttttccga acacttgtca gacaacccag tgcaggcaac aggtttacat   9300
cagaccatat cactgatgtt gaagtaggac atgcagagga acctctttca tttacttcaa   9360
gcagcatatt aaaatcgttg atgattgcta aagaagaatt ggagcttcac gcgatcagga   9420
ctggccattc tcatatgtac ttgtgcatat tgaaagagca aaagcttctt gaccttgttc   9480
ctgtttcagg gtaagcctgc acatcgttct ttttgcagaa catgtattcc ttgctcttgt   9540
gttctgcctt ctcaatgagc ttttcatcgt actcaggaac actgttgtgg atgttggtca   9600
agatgaagct actgcatgct ctcttttgaa agaaatggct ttaaagatac atgaacttgt   9660
tggtgcaaga atgcatcatc tttctgtatg ccagtgggaa gtgaaactta agttggtgag   9720
cgatgggcct gccagtggta gctggagagt tgtaacaacc aatgttactg gtcacacctg   9780
cactgtggat gtgagtttta tctccttgct tcctgttttt ctgcatggaa ctaatgaaac   9840
tgaagtgaac atattatata tgtgacatac ataggactat catctttgat tatcataaaa   9900
aaagaactat catcttcgtt tcgtttgttg tcatttccac ctcatttttg gtctgaatct   9960
catggtgctt ttaatgcttt tagatctacc gggaggtcga agatacagaa tcacagaaac  10020
tagtatacca ctccaccgca ttgtcatctg gtcctttgca tggtgttgca ctgaatactt  10080
cgtatcaacc tttgagtgtt attgatttaa aacgttgctc tgccaggaac aacaaaacta  10140
catactgcta tgattttcca ttggttagta tctatctcta tatgtattat gttagcaggt  10200
tcttattggt attacatgtc ctaaatctga caacaactca aaatgtagac atttgaagct  10260
gcagtgcaga agtcgtggtc taacatttcc agtgaaaaca accaatgtta tgttaaagcg  10320
acagagcttg tgtttgctga aaagaatggg tcgtggggca ctcctataat tcctatgcag  10380
cgtgctgctg ggctgaatga cattggtatg gtagcctgga tcttggacat gtccactcct  10440
gaatttccca gcggcagaca gatcattgtt atcgcaaatg atattacatt tagagctgga  10500
tcatttggcc caagggaaga tgcatttttc gaagctgtaa ccaacctggc ttgtgagaag  10560
aagcttccac ttatctactt ggctgcaaac tctggtgctc ggattggcat tgctgatgaa  10620
gtaaaatctt gcttccgtgt tggatggact gatgatagca gccctgaacg tggatttagg  10680
tacatttata tgactgacga agaccatgat cgtattggct cttcagttat agcacacaag  10740
atgcagctag atagtggcga gatcaggtgg gttatcgatt ctgttgtggg aaaagaggat  10800
ggactaggtg tggagaacat acatggaagt gctgctattg ccagtgccta ttctagggcg  10860
tacgaggaga catttacact tacattcgtt actggacgaa ctgttggaat cggagcctat  10920
cttgctcgac ttggcatacg gtgcatacag cgtattgacc agcccattat tttgactggg  10980
ttttctgccc tgaacaagct tcttgggcgg gaggtgtaca gctcccacat gcagttgggt  11040
ggtcccaaaa tcatggcgac gaatggtgtt gtccatctga ctgttccaga tgaccttgaa  11100
ggtgtttcta atatattgag gtggctcagc tatgttcctg caaacattgg tggacctctt  11160
cctattacaa aatctttgga cccaatagac agacccgttg catacatccc tgagaataca  11220
tgtgatcctc gtgcagccat cagtggcatt gatgacagcc aagggaaatg gttgggtggc  11280
atgtttgaca aagacagttt tgtggagaca tttgaaggat gggcgaagac agtagttact  11340
ggcagagcaa aacttggagg gattcctgtt ggtgttatag ctgtggagac acagaccatg  11400
```

```
atgcagctcg tccccgctga tccaggccag cctgattccc acgagcggtc tgttcctcgt  11460

gctgggcaag tttggtttcc agattctgct accaagacag cgcaggcgat gttggacttc  11520

aaccgtgaag gattacctct gttcatactt gctaactgga gaggcttctc tggagggcaa  11580

agagatcttt ttgaaggaaa tctgcaggct gggtcaacaa ttgttgagaa ccttaggaca  11640

tacaatcagc ctgcctttgt atatatcccc aaggctgcag agctacgtgg aggagcctgg  11700

gtcgtgattg atagcaagat aaacccagat cgcatcgagt gctatgctga gaggactgca  11760

aagggtaatg ttctcgaacc tcaagggttg attgagatca agttcaggtc agaggaactc  11820

aaagaatgca tgggtaggct tgatccagaa ttgatagatc tgaaagcaag actccaggga  11880

gcaaatggaa gcctatctga tggagaatcc cttcagaaga gcatagaagc tcggaagaaa  11940

cagttgctgc ctctgtacac ccaaatcgcg gtacgttttg cggaattgca cgacacttcc  12000

cttagaatgg ctgctaaagg tgtgatcagg aaagttgtag actgggaaga ctctcggtct  12060

ttcttctaca agagattacg gaggaggcta tccgaggacg ttctggcaaa ggagattaga  12120

ggtgtaattg gtgagaagtt tcctcacaaa tcagcgatcg agctgatcaa gaaatggtac  12180

ttggcttctg aggcagctgc agcaggaagc accgactggg atgatgacga tgcttttgtc  12240

gcctggaggg agaaccctga aaactataag gaatatatca aagagcttag ggctcaaagg  12300

gtatctcggt tgctctcaga tgttgcaggc tccagttcgg atttacaagc cttgccgcag  12360

ggtctttcca tgctactaga taaggtacgc atacttacag ttttacctgc atctgtttat  12420

ttgcaagtat tttatcgagg ttgagtatgt cctgctatct tattcaaata tagtatctta  12480

ccaaataata tctaagacgc tggatacttt gttcagatgg atccctctaa gagagcacag  12540

tttatcgagg aggtcatgaa ggtcctgaaa tgatcaaatg ataccaacac atccaataca  12600

gtatgtgcat gatatctgtt tctcttgaag tacatatata gatggataca aggcggctgt  12660

aactgatggt agctaatctg ggccaaccat tacttttgtg aacttgctgg tggtctttat  12720

tattcaaggc acagctcgcc ttcggacccc ctc                               12753
```

<210> SEQ ID NO 14
<211> LENGTH: 2320
<212> TYPE: PRT
<213> ORGANISM: Alopecurus myosuroides

<400> SEQUENCE: 14

```
Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
```

```
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
    290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
        355                 360                 365

His Leu Glu Val Gln Leu Leu Cys Asp Glu Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Ser
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510

Pro Phe Asn Phe Asp Glu Val Asp Ser Gln Trp Pro Lys Gly His Cys
        515                 520                 525

Val Ala Val Arg Ile Thr Ser Glu Asn Pro Asp Asp Gly Phe Lys Pro
    530                 535                 540

Thr Gly Gly Lys Val Lys Glu Ile Ser Phe Lys Ser Lys Pro Asn Val
545                 550                 555                 560
```

```
Trp Gly Tyr Phe Ser Val Lys Ser Gly Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
        595                 600                 605

Glu Ile His Thr Asn Val Asp Tyr Thr Val Asp Leu Leu Asn Ala Pro
    610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
            660                 665                 670

Glu Tyr Val Ser Tyr Leu Ile Lys Gly Gln Ile Pro Pro Lys His Ile
        675                 680                 685

Ser Leu Val His Ser Thr Ile Ser Leu Asn Ile Glu Glu Ser Lys Tyr
    690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
            740                 745                 750

Glu Ala Gly Gly Thr Arg Leu Leu Ile Asp Gly Lys Thr Cys Leu Leu
        755                 760                 765

Gln Asn Asp His Asp Pro Ser Arg Leu Leu Ala Glu Thr Pro Cys Lys
    770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
        835                 840                 845

Val Lys Arg Ala Glu Pro Phe Glu Gly Ser Phe Pro Glu Met Ser Leu
    850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
        915                 920                 925

Arg Leu Lys Ser Glu Leu Glu Gly Lys Tyr Asn Glu Tyr Lys Leu Asn
    930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975
```

```
Ile Glu Arg Leu Val Asp Pro Leu Met Ser Leu Leu Lys Ser Tyr Glu
            980                 985                 990

Gly Gly Arg Glu Ser His Ala His  Phe Ile Val Lys Ser  Leu Phe Glu
        995                 1000                1005

Glu Tyr  Leu Ser Val Glu Glu  Leu Phe Ser Asp Gly  Ile Gln Ser
    1010                 1015                 1020

Asp Val  Ile Glu Arg Leu Arg  Leu Gln Tyr Ser Lys  Asp Leu Gln
    1025                 1030                 1035

Lys Val  Val Asp Ile Val Leu  Ser His Gln Gly Val  Arg Asn Lys
    1040                 1045                 1050

Thr Lys  Leu Ile Leu Ala Leu  Met Glu Lys Leu Val  Tyr Pro Asn
    1055                 1060                 1065

Pro Ala  Ala Tyr Arg Asp Gln  Leu Ile Arg Phe Ser  Ser Leu Asn
    1070                 1075                 1080

His Lys  Arg Tyr Tyr Lys Leu  Ala Leu Lys Ala Ser  Glu Leu Leu
    1085                 1090                 1095

Glu Gln  Thr Lys Leu Ser Glu  Leu Arg Thr Ser Ile  Ala Arg Asn
    1100                 1105                 1110

Leu Ser  Ala Leu Asp Met Phe  Thr Glu Glu Lys Ala  Asp Phe Ser
    1115                 1120                 1125

Leu Gln  Asp Arg Lys Leu Ala  Ile Asn Glu Ser Met  Gly Asp Leu
    1130                 1135                 1140

Val Thr  Ala Pro Leu Pro Val  Glu Asp Ala Leu Val  Ser Leu Phe
    1145                 1150                 1155

Asp Cys  Thr Asp Gln Thr Leu  Gln Gln Arg Val Ile  Glu Thr Tyr
    1160                 1165                 1170

Ile Ser  Arg Leu Tyr Gln Pro  Gln Leu Val Lys Asp  Ser Ile Gln
    1175                 1180                 1185

Leu Lys  Tyr Gln Asp Ser Gly  Val Ile Ala Leu Trp  Glu Phe Thr
    1190                 1195                 1200

Glu Gly  Asn His Glu Lys Arg  Leu Gly Ala Met Val  Ile Leu Lys
    1205                 1210                 1215

Ser Leu  Glu Ser Val Ser Thr  Ala Ile Gly Ala Ala  Leu Lys Asp
    1220                 1225                 1230

Ala Ser  His Tyr Ala Ser Ser  Ala Gly Asn Thr Val  His Ile Ala
    1235                 1240                 1245

Leu Leu  Asp Ala Asp Thr Gln  Leu Asn Thr Thr Glu  Asp Ser Gly
    1250                 1255                 1260

Asp Asn  Asp Gln Ala Gln Asp  Lys Met Asp Lys Leu  Ser Phe Val
    1265                 1270                 1275

Leu Lys  Gln Asp Val Val Met  Ala Asp Leu Arg Ala  Ala Asp Val
    1280                 1285                 1290

Lys Val  Val Ser Cys Ile Val  Gln Arg Asp Gly Ala  Ile Met Pro
    1295                 1300                 1305

Met Arg  Arg Thr Phe Leu Leu  Ser Glu Glu Lys Leu  Cys Tyr Glu
    1310                 1315                 1320

Glu Glu  Pro Ile Leu Arg His  Val Glu Pro Pro Leu  Ser Ala Leu
    1325                 1330                 1335

Leu Glu  Leu Asp Lys Leu Lys  Val Lys Gly Tyr Asn  Glu Met Lys
    1340                 1345                 1350

Tyr Thr  Pro Ser Arg Asp Arg  Gln Trp His Ile Tyr  Thr Leu Arg
    1355                 1360                 1365

Asn Thr  Glu Asn Pro Lys Met  Leu His Arg Val Phe  Phe Arg Thr
```

```
    1370                1375                1380

Leu Val  Arg Gln Pro Ser Ala  Gly Asn Arg Phe Thr  Ser Asp His
    1385                1390                1395

Ile Thr  Asp Val Glu Val Gly  His Ala Glu Glu Pro  Leu Ser Phe
    1400                1405                1410

Thr Ser  Ser Ser Ile Leu Lys  Ser Leu Met Ile Ala  Lys Glu Glu
    1415                1420                1425

Leu Glu  Leu His Ala Ile Arg  Thr Gly His Ser His  Met Tyr Leu
    1430                1435                1440

Cys Ile  Leu Lys Glu Gln Lys  Leu Leu Asp Leu Val  Pro Val Ser
    1445                1450                1455

Gly Asn  Thr Val Val Asp Val  Gly Gln Asp Glu Ala  Thr Ala Cys
    1460                1465                1470

Ser Leu  Leu Lys Glu Met Ala  Leu Lys Ile His Glu  Leu Val Gly
    1475                1480                1485

Ala Arg  Met His His Leu Ser  Val Cys Gln Trp Glu  Val Lys Leu
    1490                1495                1500

Lys Leu  Val Ser Asp Gly Pro  Ala Ser Gly Ser Trp  Arg Val Val
    1505                1510                1515

Thr Thr  Asn Val Thr Gly His  Thr Cys Thr Val Asp  Ile Tyr Arg
    1520                1525                1530

Glu Val  Glu Asp Thr Glu Ser  Gln Lys Leu Val Tyr  His Ser Thr
    1535                1540                1545

Ala Leu  Ser Ser Gly Pro Leu  His Gly Val Ala Leu  Asn Thr Ser
    1550                1555                1560

Tyr Gln  Pro Leu Ser Val Ile  Asp Leu Lys Arg Cys  Ser Ala Arg
    1565                1570                1575

Asn Asn  Lys Thr Thr Tyr Cys  Tyr Asp Phe Pro Leu  Thr Phe Glu
    1580                1585                1590

Ala Ala  Val Gln Lys Ser Trp  Ser Asn Ile Ser Ser  Glu Asn Asn
    1595                1600                1605

Gln Cys  Tyr Val Lys Ala Thr  Glu Leu Val Phe Ala  Glu Lys Asn
    1610                1615                1620

Gly Ser  Trp Gly Thr Pro Ile  Ile Pro Met Gln Arg  Ala Ala Gly
    1625                1630                1635

Leu Asn  Asp Ile Gly Met Val  Ala Trp Ile Leu Asp  Met Ser Thr
    1640                1645                1650

Pro Glu  Phe Pro Ser Gly Arg  Gln Ile Ile Val Ile  Ala Asn Asp
    1655                1660                1665

Ile Thr  Phe Arg Ala Gly Ser  Phe Gly Pro Arg Glu  Asp Ala Phe
    1670                1675                1680

Phe Glu  Ala Val Thr Asn Leu  Ala Cys Glu Lys Lys  Leu Pro Leu
    1685                1690                1695

Ile Tyr  Leu Ala Ala Asn Ser  Gly Ala Arg Ile Gly  Ile Ala Asp
    1700                1705                1710

Glu Val  Lys Ser Cys Phe Arg  Val Gly Trp Thr Asp  Asp Ser Ser
    1715                1720                1725

Pro Glu  Arg Gly Phe Arg Tyr  Ile Tyr Met Thr Asp  Glu Asp His
    1730                1735                1740

Asp Arg  Ile Gly Ser Ser Val  Ile Ala His Lys Met  Gln Leu Asp
    1745                1750                1755

Ser Gly  Glu Ile Arg Trp Val  Ile Asp Ser Val Val  Gly Lys Glu
    1760                1765                1770
```

```
Asp Gly  Leu Gly Val Glu Asn  Ile His Gly Ser Ala  Ala Ile Ala
    1775                 1780                 1785

Ser Ala  Tyr Ser Arg Ala Tyr  Glu Glu Thr Phe Thr  Leu Thr Phe
    1790                 1795                 1800

Val Thr  Gly Arg Thr Val Gly  Ile Gly Ala Tyr Leu  Ala Arg Leu
    1805                 1810                 1815

Gly Ile  Arg Cys Ile Gln Arg  Ile Asp Gln Pro Ile  Ile Leu Thr
    1820                 1825                 1830

Gly Phe  Ser Ala Leu Asn Lys  Leu Leu Gly Arg Glu  Val Tyr Ser
    1835                 1840                 1845

Ser His  Met Gln Leu Gly Gly  Pro Lys Ile Met Ala  Thr Asn Gly
    1850                 1855                 1860

Val Val  His Leu Thr Val Pro  Asp Asp Leu Glu Gly  Val Ser Asn
    1865                 1870                 1875

Ile Leu  Arg Trp Leu Ser Tyr  Val Pro Ala Asn Ile  Gly Gly Pro
    1880                 1885                 1890

Leu Pro  Ile Thr Lys Ser Leu  Asp Pro Ile Asp Arg  Pro Val Ala
    1895                 1900                 1905

Tyr Ile  Pro Glu Asn Thr Cys  Asp Pro Arg Ala Ala  Ile Ser Gly
    1910                 1915                 1920

Ile Asp  Asp Ser Gln Gly Lys  Trp Leu Gly Gly Met  Phe Asp Lys
    1925                 1930                 1935

Asp Ser  Phe Val Glu Thr Phe  Glu Gly Trp Ala Lys  Thr Val Val
    1940                 1945                 1950

Thr Gly  Arg Ala Lys Leu Gly  Gly Ile Pro Val Gly  Val Ile Ala
    1955                 1960                 1965

Val Glu  Thr Gln Thr Met Met  Gln Leu Val Pro Ala  Asp Pro Gly
    1970                 1975                 1980

Gln Pro  Asp Ser His Glu Arg  Ser Val Pro Arg Ala  Gly Gln Val
    1985                 1990                 1995

Trp Phe  Pro Asp Ser Ala Thr  Lys Thr Ala Gln Ala  Met Leu Asp
    2000                 2005                 2010

Phe Asn  Arg Glu Gly Leu Pro  Leu Phe Ile Leu Ala  Asn Trp Arg
    2015                 2020                 2025

Gly Phe  Ser Gly Gly Gln Arg  Asp Leu Phe Glu Gly  Asn Leu Gln
    2030                 2035                 2040

Ala Gly  Ser Thr Ile Val Glu  Asn Leu Arg Thr Tyr  Asn Gln Pro
    2045                 2050                 2055

Ala Phe  Val Tyr Ile Pro Lys  Ala Ala Glu Leu Arg  Gly Gly Ala
    2060                 2065                 2070

Trp Val  Val Ile Asp Ser Lys  Ile Asn Pro Asp Arg  Ile Glu Cys
    2075                 2080                 2085

Tyr Ala  Glu Arg Thr Ala Lys  Gly Asn Val Leu Glu  Pro Gln Gly
    2090                 2095                 2100

Leu Ile  Glu Ile Lys Phe Arg  Ser Glu Glu Leu Lys  Glu Cys Met
    2105                 2110                 2115

Gly Arg  Leu Asp Pro Glu Leu  Ile Asp Leu Lys Ala  Arg Leu Gln
    2120                 2125                 2130

Gly Ala  Asn Gly Ser Leu Ser  Asp Gly Glu Ser Leu  Gln Lys Ser
    2135                 2140                 2145

Ile Glu  Ala Arg Lys Lys Gln  Leu Leu Pro Leu Tyr  Thr Gln Ile
    2150                 2155                 2160
```

```
Ala Val  Arg Phe Ala Glu Leu  His Asp Thr Ser Leu  Arg Met Ala
    2165                 2170                 2175

Ala Lys  Gly Val Ile Arg Lys  Val Val Asp Trp Glu  Asp Ser Arg
    2180                 2185                 2190

Ser Phe  Phe Tyr Lys Arg Leu  Arg Arg Arg Leu Ser  Glu Asp Val
    2195                 2200                 2205

Leu Ala  Lys Glu Ile Arg Gly  Val Ile Gly Glu Lys  Phe Pro His
    2210                 2215                 2220

Lys Ser  Ala Ile Glu Leu Ile  Lys Lys Trp Tyr Leu  Ala Ser Glu
    2225                 2230                 2235

Ala Ala  Ala Ala Gly Ser Thr  Asp Trp Asp Asp Asp  Asp Ala Phe
    2240                 2245                 2250

Val Ala  Trp Arg Glu Asn Pro  Glu Asn Tyr Lys Glu  Tyr Ile Lys
    2255                 2260                 2265

Glu Leu  Arg Ala Gln Arg Val  Ser Arg Leu Leu Ser  Asp Val Ala
    2270                 2275                 2280

Gly Ser  Ser Ser Asp Leu Gln  Ala Leu Pro Gln Gly  Leu Ser Met
    2285                 2290                 2295

Leu Leu  Asp Lys Met Asp Pro  Ser Lys Arg Ala Gln  Phe Ile Glu
    2300                 2305                 2310

Glu Val  Met Lys Val Leu Lys
    2315                 2320
```

<210> SEQ ID NO 15
<211> LENGTH: 12683
<212> TYPE: DNA
<213> ORGANISM: Alopecurus myosuroides

<400> SEQUENCE: 15

```
tcagtttatg gcagtctgtg tttgaagaac actgcaactc cgctgtctgt ccaaagggag     60

gacgatggga tccacacatc tgcccattgt cgggtttaat gcatccacaa caccatcgct    120

atccactctt cgccagataa actcagctgc tgctgcattc caatcttcgt cccttcaag    180

gtcatccaag aagaaaagcc gacgtgttaa gtcaataagg gatgatggcg atggaagcgt    240

gccagaccct gcaggccatg gccagtctat tcgccaaggt gaacctagga ccatctcctt    300

actttttgt cgtcaacctc agacttgcat agatttactt tcttgattga gagcatgctt    360

gttttagtgt aagatatctc aatactgtat cacaaaatga tagttaagaa caaatcacta    420

caccaatctt cacatattgt tcttattggg tttgctaaat cttagttcgc attagatttt    480

tttatgtcta tgtcgacacc ctgagcctcc ccgtgtctct gcattgagat tcaagcaggg    540

attagggaaa tcacgactgg atcagaaggc aagcaccatc gccttagcca taattaaatc    600

tctgtcaacc taggtgtaga tggactctgt ttttaatatt cagtatgatg ttttcttaag    660

ggagagggac acaaaaatat agtaagtaga agccttacct tcggaaaata cccatttaac    720

ctctgggagc atttgctact gcctagaaaa atccactttt taaagtttca ataattgcaa    780

agacaagtta ctatgtgata gtacaaagtt tggtggagaa acaacttttt ggtctatgta    840

ataaaaaaga caaatatatg acacatgtat gttgcagttt aagaatttat gactgaatgt    900

tttgatgata taatagttct ggaaaagaag gatgcctaga ttttgttttt tgataaatgt    960

agttataaaa ttcgaaaggt tggcaaacca ttgcttcttc ttagctattg tgttggcttg   1020

ctcagtttcc aatgcatatc tggatgtagg tctcgctggc atcatcgacc tcccaaagga   1080

gggcgcatca gctccagatg tggacatttc acagtaagta cctcagcaca ctcacattat   1140
```

-continued

```
agcttagttc tcttgaaaga acagcaaaaa tgtataacgc atgtatagtt cctagatttc   1200
acttgtctta ttatcgttac gctgaaatgt tgaagttgta aattcgttat tctcatagat   1260
ttacacctct atgtacatct atgcactatg cacctgctgt gagttctgga aattgaacca   1320
ttcagcgcac tgcaatctgt aaggttttgt ttttatataa tatggttata aatcatgttc   1380
aacctctgca tctacaacat tatttatgtg tggtatagta tatagtaatg ttacagggtg   1440
agattttgct atataagtta tgaaacttgt gttcaacttt gtaaagggaa acatcctcaa   1500
acctgttctt agtggttaca gcccaggcac atggccgttg cactgtatgg agtattgttg   1560
ggcacttaca aaacatttta ttggaaagat tttttgatat aagtattgtt taaatttaat   1620
tgccaactga aacccttacc cggataacaa gatgaataac ccacttgcgt ttttgattca   1680
tactaggcat tactacgtca tatgtattac ggtgaccgca gtaataactt tgctctttct   1740
tttctagtgg gtctgaagac cacaaggcct cctaccaaat gaatgggata ctgaatgaat   1800
cacataacgg gaggcacgcc tctctgtcta aagtttatga attttgcacg gaattgggtg   1860
gaaaaacacc aattcacagt gtattagtcg ccaacaatgg aatggcagca gctaagttca   1920
tgcggagtgt ccggacatgg gctaatgata catttgggtc agagaaggcg attcagttga   1980
tagctatggc aactccggaa gacatgagaa taaatgcaga gcacattaga attgctgatc   2040
agtttgttga agtacctggt ggaacaaaca ataacaacta tgcaaatgtc caactcatag   2100
tggaggtcag tactggtcat cccttgatgt gcagttatgc acaagctcct ctttggtctt   2160
tagcatgaca tggcaacttc acttttgcag atagcagaga gaactggtgt ctccgccgtt   2220
tggcctggtt ggggccatgc atctgagaat cctgaacttc cagatgcact aactgcaaaa   2280
ggaattgttt ttcttgggcc accagcatca tcaatgaacg cactaggcga caaggttggt   2340
tcagctctca ttgctcaagc agcaggggtt cccactcttg cttggagtgg atcacacgta   2400
agcctcacat tctctctgat aaatcatcac ctgatatttg tggtggatgc attatgtaac   2460
ctatgacatt tttattatag gtggaaattc cattagaact ttgtttggac tcgatacctg   2520
aggagatgta taggaaagcc tgtgttacaa ccgctgatga agcagttgca agttgtcaga   2580
tgattggtta ccctgccatg atcaaggcat cctggggtgg tggtggtaaa gggattagaa   2640
aggtacatta ttcatttgat tggactgtac acaagagatt gtgtgggctg tgatattttg   2700
tgcacagtgt tagccctaac ctttttaaca tattaactcg atatctcttg caggttaata   2760
atgatgacga ggtgaaagca ctgtttaagc aagtacaggg tgaagttcct ggctccccga   2820
tatttatcat gagacttgca tctcaggtta gacttctcta gaagttctat tttccaagcg   2880
tgctgtatct gggttgtata ttgtacgtat ggaagcttta tttgctcttt cttacaggct   2940
aaaattgtat cctgtaatct gtactaatat tgtaattttc atttaaatcc ctctcccctt   3000
tccctttgta gagtcgtcat cttgaagtcc agctgctttg tgatgaatat ggcaatgtag   3060
cagcacttca cagtcgtgat tgcagtgtgc aacgacgaca ccaaaaggta tgctgctcca   3120
aactgaaatc atcactttta tttcggttct gctttacgtg tagttttgat caaatggttc   3180
aactgtgtcc attttgtttg tttataacag attatcgagg aaggaccagt tactgttgct   3240
cctcgtgaaa cagtgaaaga gctagagcaa gcagcaagga ggcttgctaa ggccgtgggt   3300
tacgtcggtg ctgctactgt tgaatatctc tacagcatgg agactggtga atactatttt   3360
ctggagctta atccacggtt gcaggtttgt tcttttggac actctccagg acttctattt   3420
tgttggcagt cgtttacatt gttaaatggt ctatattcag gttgagcacc cagtcaccga   3480
gtcgatagct gaagtaaatt tgcctgcagc ccaagttgca gttgggatgg gtatacccct   3540
```

```
ttggcagatt ccaggtaata ataatatcat tgtaaagagt ttcgtttctg tcccatgttc   3600
tttctgtcta actatctcct tattcagaga tcagacgttt ctacggaatg gacaatggag   3660
gaggctatga tatttggagg aaaacagcag ctctcgctac tccattcaac tttgatgaag   3720
tagattctca atggccgaag ggtcattgtg tggcagttag gataaccagt gagaatccag   3780
atgatggatt caagcctact ggtggaaaag taaaggtggg atttcctaat gttatatcta   3840
tgtttcaatt acactacggt tagtaaactg atctgatctt gattttttc gtatatttca    3900
ggagataagt tttaaaagta agccaaatgt ctggggatat ttctcagtta aggtaagctg   3960
ttcatagctc tgttgcaggg tcatcttgtt ttgagttccg cagaagatta gtctgcaaga   4020
tttttattcg aattagtatt ctcattttgg tttttgacta agtattgatc caatcaacaa   4080
atattgtctc tcccttcatc tgttttcagt ctggtggagg cattcatgaa tttgcggatt   4140
ctcagtttgg tatgtaaaat gtgacgtaat gaatattcct ctttgctatt cgtattgatc   4200
cttacattgg aattgctcct ttcattacag gacatgtttt tgcctatgga gagactagat   4260
cagcagcaat aaccagcatg tctcttgcac taaaagagat tcaaattcgt ggagaaattc   4320
atacaaacgt tgattacacg gttgatctct tgaatgtaag taacaataac aatttgttga   4380
atcctacttt tgatgtgata caaccatttt acatccggtt ttccttcaaa ataatcccat   4440
tctgtggttt ctcgtatctt taattcaggc cccagacttc agagaaaaca cgatccatac   4500
cggttggctg gataccagaa tagctatgcg tgttcaagct gagaggcctc cctggtatat   4560
ttcagtggtt ggaggagctc tatatgtaag atatgaaact atgttaatgt tactgcaact   4620
tttggcaagc caatcttgaa aaacagtagt gtttaattga aataattgtt ttgtgctgta   4680
gaaaacaata accaccaatg cggagaccgt ttctgaatat gttagctatc tcatcaaggg   4740
tcagattcca ccaaaggtag tgtcttaatg ggcttaaact ctgtatattg cttgaaggtg   4800
gacattgctg accattgttt ttgtgcagca tatatccctt gtccattcaa ctatttcttt   4860
gaatatagag gaaagcaaat atacagtaag tgtgacattc cttaaaaaaa gactctcagt   4920
tacaatgaaa tgatacttac actgatgctc atctacacca tgccacagat tgagattgtg   4980
aggagtggac agggtagcta cagattgaga atgaatggat cacttattga agccaatgta   5040
caaacattat gtgatggagg ccttttaatg caggtacctt ctttctttta cttgctcata   5100
aatgtgatat aatgtctgct gaaagagttc tgattcttta gttgtaatgt ctccagctgg   5160
atggaaatag ccatgttatt tatgctgaag aagaagcggg tggtacacag cttcttattg   5220
atggaaaaac atgcttgcta caggtaagaa tattctgttt gtttgctcct tttataatctt  5280
agtgtttgat ggtaggactt tatattctta tttgtgactt tttactgcat tcacctcttg   5340
accattagca cttcattttt tacacttcat ctgtattgct tctgctgttt ctcaattata   5400
gttattccaa tgaccactct ttagtaattt taacaattgc caatttatca taatacgggg   5460
caaaaaagta ggtgtcctta acaccatgtc atgtaaccta taataagctt gtgataaaat   5520
catttgtgat ataatagaac aattgaatac tttatgattt ctttcttaca tgaatacttt   5580
atgattcttg atgacgctgc actgtatcct aaactacata aattacaaat cgttttgcag   5640
aatgaccatg atccgtcaag gttattagct gagacaccct gcaaacttct tcgtttcttg   5700
attgccgatg gtgctcatgt tgatgctgat gtaccatacg cggaagttga ggttatgaag   5760
atgtgcatgc ccctcttgtc gcctgctgct ggtgtcatta atgttttgtt gtctgagggc   5820
caggcgatgc aggttatatt actgcccttt tgttgcttct gctgataaaa gccattgcat   5880
```

```
gtgaagcatc tgaacttaat atattttgtt tcaggctggt gatcttatag cgagacttga   5940
tctcgatgac ccttctgctg tgaagagagc tgagccattt gaaggatctt ttccagaaat   6000
gagccttcct attgctgctt ctggccaagt tcacaaaaga tgtgctgcaa gtttgaacgc   6060
tgctcgaatg gtccttgcag gatatgacca tgcggccaac aaagtaaaca tcaagacatt   6120
ttatctcatg tttcctgctt ttctcaaata ccattcttta atagtatgaa ttctggatta   6180
ttctgactta ttggcatttt ctgccttttg ctaccaaatg gtttctaatc tatagaagtt   6240
cttgagcttg tctttgcaaa tctcgattta atgcttttct tgtatgttca tcatactcat   6300
ttatgatagg ttgcatttat ccttctgcta ttttcctttc tctcagtaaa tcatgatgga   6360
tgctctttct gttatgttca tcatgctgtc tattatcctt gtgctatttt tctatttcca   6420
gtagtggatg tattggttta ataattcctg atcaaacttt gtattttgtt gttatttata   6480
cttggcttcc ttttcaggtt gtgcaagatt tggtatggtg ccttgataca cctgctcttc   6540
ctttcctaca atgggaagag cttatgtctg ttttagcaac tagacttcca agacgtctta   6600
agagcgaggt atgtgataat tgatatgata tgcagaatca ggcataaagg gacattgata   6660
catttaattt atgatataga agggtcttca tcctcgatta aaagatcaat tcacttatca   6720
tgatttacat tctacattgt tgaatcacct tggtaatttg ccgtaactta ttgggcaact   6780
attagctttt ctaataacgt aatcaaaatt cagaatattt tacttcaatt cttcgtaaca   6840
tggaacattt ggtacttcgt ctcatttatt tgcactgtac gctgttttag ttggtttgcc   6900
attctaactg aatctttaaa gttcttactt atttggtttt aacccagatc ttgtttattt   6960
atcttttata actttcttat gttctgcctc aacggttcat actttttatg catccagttg   7020
gagggcaaat acaatgaata caagttaaat gttgaccatg tgaagatcaa ggatttccct   7080
accgagatgc ttagagagac aatcgaggtc agtttttgtt tcttatggca tcccagtcta   7140
aattatacta ttttttgtaa caagttttct tttaggaaaa tcttgcatgt gtttccgaga   7200
aggaaatggt gacaattgag aggcttgttg accctctgat gaacctgctg aagtcatacg   7260
agggtgggag agaaagccat gcccacttta ttgtcaagtc ccttttttgag gagtatctct   7320
cggttgagga actattcagt gatggcattc aggttatcta acacttctaa actgagcaga   7380
tctactagag tcattttcta agggtcataa ttttccagaa cctcttgggt gattaagtag   7440
caaaaataat ttgtacacga cttacgactt acttccttcg aaacactttt cactcattat   7500
tttcctcaaa atgtgccatt ttgtagtctg acgtgattga acgcctgcgc ctacaatata   7560
gtaaagacct ccagaaggtt gtagacattg ttttgtctca ccaggtaaac tactttttgg   7620
cctaatgact tggtgcaagt gatcacagaa acaatctttg ttactgatag tttgatttgt   7680
tctagggtgt gagaaacaaa acaaagctga tactcgcgct catggagaaa ctggtctatc   7740
caaaccctgc tgcctacaga gatcagttga ttcgcttttc ttccctcaac cataaaagat   7800
attataaggt gacaatggcg acctaaagta atggaagctt tttgattaat ttgttgtgat   7860
attttaggct aatgaattac tttcattgta attctgcagt tggctcttaa agctagtgaa   7920
cttcttgaac aaaccaagct cagcgaactc cgcacaagca ttgcaaggaa cctttcaacg   7980
ctggatatgt tcaccgagga aaaggcagat ttctccttgc aagacagaaa attggccatt   8040
aatgagagca tgggagattt agtcactgcc ccactgccag ttgaagatgc acttgtttct   8100
ttgtttgatt gtactgatca aactcttcag cagagagtga ttgagacata catatctcga   8160
ttataccagg tattacatga gctatttttt tctggatttt attatactct ctctcagcat   8220
ttctggaagc ataaactaag gttcctaatg aaataagata ctcagtgttt cattaagata   8280
```

```
aatcctagat aatctaggcg tgggaagatt tgatttagaa cttgtaggca tgttactgct   8340
ctgtaagttg gctaacttgc caatgatatt ttcagcctca acttgtgaag gatagcatcc   8400
agctgaaata tcaggattct ggtgttattg ctttatggga attcactgaa ggaaatcatg   8460
agaagagatt gggtgctatg gttatcctga agtcactaga atctgtgtca acagccattg   8520
gagctgctct aaaggatgca tcacattatg caagctctgc gggcaacacg gtgcatattg   8580
ctttgttgga tgctgatacc caactgaata caactgaaga taggtatgtt catgtgcagt   8640
attagtgcag atgagtttat ttggtgcaaa aataagttaa tctatttctt tcagtggtga   8700
taatgaccaa gctcaagaca agatggataa actttctttt gtactgaaac aagatgttgt   8760
catggctgat ctacgtgctg ctgatgtcaa ggttgttagt tgcattgttc aaagagatgg   8820
agcaatcatg cctatgcgcc gtaccttcct cttgtcagag gaaaaacttt gttacgagga   8880
agagccgatt cttcggcatg tggagcctcc actttctgca cttcttgagt tggtatgcaa   8940
ctccatcaaa ctgactacgt gctgttttga tatattttaa tgctttcact ttgttatttg   9000
ctacttgtat tcacttagct tgctgtggat acaggataaa ttgaaagtga aaggatacaa   9060
tgagatgaag tatacaccgt cacgtgatcg tcagtggcat atatacacac ttagaaatac   9120
tgaaaatcca aaaatgctgc acagggtatt tttccgaaca ctagtcagac aacccagtgc   9180
aggcaacagg tttacatcag accatatcac tgatgttgaa gtaggacacg cagaggaacc   9240
tctttcattt acttcaagca gcatattaaa atcgttgatg attgctaaag aagaattgga   9300
gcttcacgcg atcaggactg gccattctca tatgtacttg tgcatattga aagagcaaaa   9360
gcttcttgac cttgttcctg tttcagggta agcctgcaca tcgttctttt tgcagaacat   9420
gtattccttg ctcttgtgtt ttgccttctc aatgagcttt tcatcgtact caggaacact   9480
gttgtggatg ttggtcaaga tgaagctact gcatgctctc ttttgaaaga aatggcttta   9540
aagatacatg aacttgttgg tgcaagaatg catcatcttt ctgtttgcca gtgggaagtg   9600
aaacttaagt tggtgagcga tgggcctgcc agtggtagct ggagagttgt aacaaccaat   9660
gttactggtc acacctgcac tgtggatgtg agttttatct ccttgcttcc tgtttttctg   9720
catggaacta atgaaactga agtgaacata ttatatatgt gacatacata tgactatcat   9780
ctttgattat cataaaaaaa gaactatcat cttcgtttag tttgttgtca tttccacctc   9840
atttttggtc tgaatctcat ggtgctttta atgcttttag atctaccggg aggtcgaaga   9900
tacagaatca cagaaactag tataccactc caccgcattg tcatctggtc ctttgcatgg   9960
tgttgcactg aatacttcgt atcagccttt gagtgttatt gatttaaaac gttgctctgc  10020
caggaacaac aaaactacat actgctatga ttttccattg gttagtatct atctctctct  10080
atatgtatta tgttagcagg ttcttattgg tattacatgt cctaaatctg acaacaactc  10140
aaaatgtaga catttgaagc tgcagtgcag aagtcgtggt ctaacatttc cagtgaaaac  10200
aaccaatgtt atgttaaagc gacagagctt gtgtttgctg aaaagaatgg gtcgtggggc  10260
actcctataa ttcctatgca gcgtgctgct gggctgaatg acattggtat ggtagcctgg  10320
atcttggaca tgtccactcc tgaatttccc agcggcagac agatcattgt tatcgcaaat  10380
gatattacat ttagagctgg atcatttggc ccaagggaag atgcattttt cgaagctgta  10440
accaacctgg cttgtgagaa gaagcttcca cttatctact tggctgcaaa ctctggtgct  10500
cggattggca ttgctgatga agtaaaatct tgcttccgtg ttggatggac tgatgatagc  10560
agccctgaac gtggatttag gtacatttat atgactgacg aagaccatga tcgtataggc  10620
```

```
tcttcagtta tagcacacaa gatgcagcta gatagtggcg agatcaggtg ggttatcgat  10680

tctgttgtgg gaaaagagga tggactaggt gtggagaaca tacatggaag tgctgctatt  10740

gccagtgcct attctagggc gtacgaggag acatttacac ttacattcgt tactggacga  10800

actgttggaa tcggagccta tcttgctcga cttggcatac ggtgcataca gcgtattgac  10860

cagcccatta ttttgaccgg gttttctgcc ctgaacaagc ttcttgggcg ggaggtgtac  10920

agctcccaca tgcagttggg tggtcccaaa atcatggcga cgaatggtgt tgtccatctg  10980

actgttccag atgaccttga aggtgtttct aatatattga ggtggctcag ctatgttcct  11040

gcaaacattg gtggacctct tcctattaca aaatctttgg acccaataga cagacccgtt  11100

gcatacatcc ctgagaatac atgtgatcct cgtgcagcca tcagtggcat tgatgacagc  11160

caagggaaat ggttgggtgg catgtttgac aaagacagtt ttgtggagac atttgaagga  11220

tgggcgaaga cagtagttac tggcagagca aaacttggag ggattcctgt tggtgttata  11280

gctgtggaga cacagaccat gatgcagctc gtccccgctg atccaggcca gcctgattcc  11340

catgagcggt ctgttcctcg tgctgggcaa gtttggtttc cagattctgc taccaagaca  11400

gcgcaggcga tgttggactt caaccgtgaa ggattacctc tgttcatact tgctaactgg  11460

agaggcttct ctggagggca aagagatctt tttgaaggaa atctgcaggc tgggtcaaca  11520

attgttgaga accttaggac atacaatcag cctgcctttg tatatatccc caaggctgca  11580

gagctacgtg gaggagcctg ggtcgtgatt gatagcaaga taaacccaga tcgcatcgag  11640

tgctatgctg agaggactgc aaagggtaat gttctcgaac ctcaagggtt gattgagatc  11700

aagttcaggt cagaggaact caaagaatgc atgggtaggc ttgatccaga attgatagat  11760

ctgaaagcaa gactccaggg agcaaatgga agcctatctg atggagaatc ccttcagaag  11820

agcatagaag ctcggaagaa acagttgctg cctctgtaca cccaaatcgc ggtacgtttt  11880

gcggaattgc acgacacttc ccttagaatg gctgctaaag gtgtgatcag gaaagttgta  11940

gactgggaag actctcggtc tttcttctac aagagattac ggaggaggct atccgaggac  12000

gttctggcaa aggagattag aggtgtaatt ggtgagaagt ttcctcacaa atcagcgatc  12060

gagctgatca agaaatggta cttggcttcc gaggcagctg cagcaggaag caccgactgg  12120

gatgacgacg atgcttttgt cgcctggagg gagaaccctg aaaactataa ggagtatatc  12180

aaagagctta gggctcaaag ggtatctcgg ttgctctcag atgttgcagg ctccagttcg  12240

gatttacaag ccttgccgca gggtctttcc atgctactag ataaggtacg catacttaca  12300

gttttacctg catctgttta tttgcaagta ttttatcgag gttgagtaaa atgctgctat  12360

cttcatatac acttgtatgt cctgctatct tattcaaata tagtatctta ccaaataata  12420

tctaagacgc tggatacttt gttcagatgg atccctctaa gagagcacag tttatcgagg  12480

aggtcatgaa ggtcctgaaa tgatcaaatg ataccaacac atccaataca gtatgtgcat  12540

gatatctgtt tctcttgaag tacatatata gatggataca aggcggctgt aactgatggt  12600

agctaatctg ggccaaccat tacttttgtg aacttgctgg tggtctttat tattcaaggc  12660

acagctcgcc ttcggacccc ctc                                          12683
```

<210> SEQ ID NO 16
<211> LENGTH: 2320
<212> TYPE: PRT
<213> ORGANISM: Alopecurus myosuroides

<400> SEQUENCE: 16

Met Gly Ser Thr His Leu Pro Ile Val Gly Phe Asn Ala Ser Thr Thr

```
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Ser Lys Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95

Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
        115                 120                 125

Leu Gly Gly Lys Thr Pro Ile His Ser Val Leu Val Ala Asn Asn Gly
    130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Asn Tyr Ala Asn Val Gln
        195                 200                 205

Leu Ile Val Glu Ile Ala Glu Arg Thr Gly Val Ser Ala Val Trp Pro
    210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
    290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
        355                 360                 365

His Leu Glu Val Gln Leu Leu Cys Asp Glu Tyr Gly Asn Val Ala Ala
    370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430
```

```
Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Ser
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510

Pro Phe Asn Phe Asp Glu Val Asp Ser Gln Trp Pro Lys Gly His Cys
        515                 520                 525

Val Ala Val Arg Ile Thr Ser Glu Asn Pro Asp Asp Gly Phe Lys Pro
    530                 535                 540

Thr Gly Gly Lys Val Lys Glu Ile Ser Phe Lys Ser Lys Pro Asn Val
545                 550                 555                 560

Trp Gly Tyr Phe Ser Val Lys Ser Gly Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
        595                 600                 605

Glu Ile His Thr Asn Val Asp Tyr Thr Val Asp Leu Leu Asn Ala Pro
    610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
            660                 665                 670

Glu Tyr Val Ser Tyr Leu Ile Lys Gly Gln Ile Pro Pro Lys His Ile
        675                 680                 685

Ser Leu Val His Ser Thr Ile Ser Leu Asn Ile Glu Glu Ser Lys Tyr
    690                 695                 700

Thr Ile Glu Ile Val Arg Ser Gly Gln Gly Ser Tyr Arg Leu Arg Met
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
            740                 745                 750

Glu Ala Gly Gly Thr Gln Leu Leu Ile Asp Gly Lys Thr Cys Leu Leu
        755                 760                 765

Gln Asn Asp His Asp Pro Ser Arg Leu Leu Ala Glu Thr Pro Cys Lys
    770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
            820                 825                 830

Gln Ala Gly Asp Leu Ile Ala Arg Leu Asp Leu Asp Asp Pro Ser Ala
        835                 840                 845
```

```
Val Lys Arg Ala Glu Pro Phe Glu Gly Ser Phe Pro Glu Met Ser Leu
    850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
        915                 920                 925

Arg Leu Lys Ser Glu Leu Glu Gly Lys Tyr Asn Glu Tyr Lys Leu Asn
    930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975

Ile Glu Arg Leu Val Asp Pro Leu Met Asn Leu Leu Lys Ser Tyr Glu
            980                 985                 990

Gly Gly Arg Glu Ser His Ala His  Phe Ile Val Lys Ser  Leu Phe Glu
        995                 1000                1005

Glu Tyr  Leu Ser Val Glu Glu  Leu Phe Ser Asp Gly  Ile Gln Ser
    1010                 1015                 1020

Asp Val  Ile Glu Arg Leu Arg  Leu Gln Tyr Ser Lys  Asp Leu Gln
    1025                 1030                 1035

Lys Val  Val Asp Ile Val Leu  Ser His Gln Gly Val  Arg Asn Lys
    1040                 1045                 1050

Thr Lys  Leu Ile Leu Ala Leu  Met Glu Lys Leu Val  Tyr Pro Asn
    1055                 1060                 1065

Pro Ala  Ala Tyr Arg Asp Gln  Leu Ile Arg Phe Ser  Ser Leu Asn
    1070                 1075                 1080

His Lys  Arg Tyr Tyr Lys Leu  Ala Leu Lys Ala Ser  Glu Leu Leu
    1085                 1090                 1095

Glu Gln  Thr Lys Leu Ser Glu  Leu Arg Thr Ser Ile  Ala Arg Asn
    1100                 1105                 1110

Leu Ser  Thr Leu Asp Met Phe  Thr Glu Glu Lys Ala  Asp Phe Ser
    1115                 1120                 1125

Leu Gln  Asp Arg Lys Leu Ala  Ile Asn Glu Ser Met  Gly Asp Leu
    1130                 1135                 1140

Val Thr  Ala Pro Leu Pro Val  Glu Asp Ala Leu Val  Ser Leu Phe
    1145                 1150                 1155

Asp Cys  Thr Asp Gln Thr Leu  Gln Gln Arg Val Ile  Glu Thr Tyr
    1160                 1165                 1170

Ile Ser  Arg Leu Tyr Gln Pro  Gln Leu Val Lys Asp  Ser Ile Gln
    1175                 1180                 1185

Leu Lys  Tyr Gln Asp Ser Gly  Val Ile Ala Leu Trp  Glu Phe Thr
    1190                 1195                 1200

Glu Gly  Asn His Glu Lys Arg  Leu Gly Ala Met Val  Ile Leu Lys
    1205                 1210                 1215

Ser Leu  Glu Ser Val Ser Thr  Ala Ile Gly Ala Ala  Leu Lys Asp
    1220                 1225                 1230

Ala Ser  His Tyr Ala Ser Ser  Ala Gly Asn Thr Val  His Ile Ala
    1235                 1240                 1245

Leu Leu  Asp Ala Asp Thr Gln  Leu Asn Thr Thr Glu  Asp Ser Gly
```

```
    1250                1255                1260

Asp Asn  Asp Gln Ala Gln Asp  Lys Met Asp Lys Leu  Ser Phe Val
    1265                1270                1275

Leu Lys  Gln Asp Val Val Met  Ala Asp Leu Arg Ala  Ala Asp Val
    1280                1285                1290

Lys Val  Val Ser Cys Ile Val  Gln Arg Asp Gly Ala  Ile Met Pro
    1295                1300                1305

Met Arg  Arg Thr Phe Leu Leu  Ser Glu Glu Lys Leu  Cys Tyr Glu
    1310                1315                1320

Glu Glu  Pro Ile Leu Arg His  Val Glu Pro Pro Leu  Ser Ala Leu
    1325                1330                1335

Leu Glu  Leu Asp Lys Leu Lys  Val Lys Gly Tyr Asn  Glu Met Lys
    1340                1345                1350

Tyr Thr  Pro Ser Arg Asp Arg  Gln Trp His Ile Tyr  Thr Leu Arg
    1355                1360                1365

Asn Thr  Glu Asn Pro Lys Met  Leu His Arg Val Phe  Phe Arg Thr
    1370                1375                1380

Leu Val  Arg Gln Pro Ser Ala  Gly Asn Arg Phe Thr  Ser Asp His
    1385                1390                1395

Ile Thr  Asp Val Glu Val Gly  His Ala Glu Glu Pro  Leu Ser Phe
    1400                1405                1410

Thr Ser  Ser Ser Ile Leu Lys  Ser Leu Met Ile Ala  Lys Glu Glu
    1415                1420                1425

Leu Glu  Leu His Ala Ile Arg  Thr Gly His Ser His  Met Tyr Leu
    1430                1435                1440

Cys Ile  Leu Lys Glu Gln Lys  Leu Leu Asp Leu Val  Pro Val Ser
    1445                1450                1455

Gly Asn  Thr Val Val Asp Val  Gly Gln Asp Glu Ala  Thr Ala Cys
    1460                1465                1470

Ser Leu  Leu Lys Glu Met Ala  Leu Lys Ile His Glu  Leu Val Gly
    1475                1480                1485

Ala Arg  Met His His Leu Ser  Val Cys Gln Trp Glu  Val Lys Leu
    1490                1495                1500

Lys Leu  Val Ser Asp Gly Pro  Ala Ser Gly Ser Trp  Arg Val Val
    1505                1510                1515

Thr Thr  Asn Val Thr Gly His  Thr Cys Thr Val Asp  Ile Tyr Arg
    1520                1525                1530

Glu Val  Glu Asp Thr Glu Ser  Gln Lys Leu Val Tyr  His Ser Thr
    1535                1540                1545

Ala Leu  Ser Ser Gly Pro Leu  His Gly Val Ala Leu  Asn Thr Ser
    1550                1555                1560

Tyr Gln  Pro Leu Ser Val Ile  Asp Leu Lys Arg Cys  Ser Ala Arg
    1565                1570                1575

Asn Asn  Lys Thr Thr Tyr Cys  Tyr Asp Phe Pro Leu  Thr Phe Glu
    1580                1585                1590

Ala Ala  Val Gln Lys Ser Trp  Ser Asn Ile Ser Ser  Glu Asn Asn
    1595                1600                1605

Gln Cys  Tyr Val Lys Ala Thr  Glu Leu Val Phe Ala  Glu Lys Asn
    1610                1615                1620

Gly Ser  Trp Gly Thr Pro Ile  Ile Pro Met Gln Arg  Ala Ala Gly
    1625                1630                1635

Leu Asn  Asp Ile Gly Met Val  Ala Trp Ile Leu Asp  Met Ser Thr
    1640                1645                1650
```

```
Pro Glu  Phe Pro Ser Gly Arg  Gln Ile Ile Val Ile  Ala Asn Asp
    1655                 1660                 1665

Ile Thr  Phe Arg Ala Gly Ser  Phe Gly Pro Arg Glu  Asp Ala Phe
    1670                 1675                 1680

Phe Glu  Ala Val Thr Asn Leu  Ala Cys Glu Lys Lys  Leu Pro Leu
    1685                 1690                 1695

Ile Tyr  Leu Ala Ala Asn Ser  Gly Ala Arg Ile Gly  Ile Ala Asp
    1700                 1705                 1710

Glu Val  Lys Ser Cys Phe Arg  Val Gly Trp Thr Asp  Asp Ser Ser
    1715                 1720                 1725

Pro Glu  Arg Gly Phe Arg Tyr  Ile Tyr Met Thr Asp  Glu Asp His
    1730                 1735                 1740

Asp Arg  Ile Gly Ser Ser Val  Ile Ala His Lys Met  Gln Leu Asp
    1745                 1750                 1755

Ser Gly  Glu Ile Arg Trp Val  Ile Asp Ser Val Val  Gly Lys Glu
    1760                 1765                 1770

Asp Gly  Leu Gly Val Glu Asn  Ile His Gly Ser Ala  Ala Ile Ala
    1775                 1780                 1785

Ser Ala  Tyr Ser Arg Ala Tyr  Glu Glu Thr Phe Thr  Leu Thr Phe
    1790                 1795                 1800

Val Thr  Gly Arg Thr Val Gly  Ile Gly Ala Tyr Leu  Ala Arg Leu
    1805                 1810                 1815

Gly Ile  Arg Cys Ile Gln Arg  Ile Asp Gln Pro Ile  Ile Leu Thr
    1820                 1825                 1830

Gly Phe  Ser Ala Leu Asn Lys  Leu Leu Gly Arg Glu  Val Tyr Ser
    1835                 1840                 1845

Ser His  Met Gln Leu Gly Gly  Pro Lys Ile Met Ala  Thr Asn Gly
    1850                 1855                 1860

Val Val  His Leu Thr Val Pro  Asp Asp Leu Glu Gly  Val Ser Asn
    1865                 1870                 1875

Ile Leu  Arg Trp Leu Ser Tyr  Val Pro Ala Asn Ile  Gly Gly Pro
    1880                 1885                 1890

Leu Pro  Ile Thr Lys Ser Leu  Asp Pro Ile Asp Arg  Pro Val Ala
    1895                 1900                 1905

Tyr Ile  Pro Glu Asn Thr Cys  Asp Pro Arg Ala Ala  Ile Ser Gly
    1910                 1915                 1920

Ile Asp  Asp Ser Gln Gly Lys  Trp Leu Gly Gly Met  Phe Asp Lys
    1925                 1930                 1935

Asp Ser  Phe Val Glu Thr Phe  Glu Gly Trp Ala Lys  Thr Val Val
    1940                 1945                 1950

Thr Gly  Arg Ala Lys Leu Gly  Gly Ile Pro Val Gly  Val Ile Ala
    1955                 1960                 1965

Val Glu  Thr Gln Thr Met Met  Gln Leu Val Pro Ala  Asp Pro Gly
    1970                 1975                 1980

Gln Pro  Asp Ser His Glu Arg  Ser Val Pro Arg Ala  Gly Gln Val
    1985                 1990                 1995

Trp Phe  Pro Asp Ser Ala Thr  Lys Thr Ala Gln Ala  Met Leu Asp
    2000                 2005                 2010

Phe Asn  Arg Glu Gly Leu Pro  Leu Phe Ile Leu Ala  Asn Trp Arg
    2015                 2020                 2025

Gly Phe  Ser Gly Gly Gln Arg  Asp Leu Phe Glu Gly  Asn Leu Gln
    2030                 2035                 2040
```

```
Ala Gly Ser Thr Ile Val Glu Asn Leu Arg Thr Tyr Asn Gln Pro
    2045                2050                2055

Ala Phe Val Tyr Ile Pro Lys Ala Ala Glu Leu Arg Gly Gly Ala
    2060                2065                2070

Trp Val Val Ile Asp Ser Lys Ile Asn Pro Asp Arg Ile Glu Cys
    2075                2080                2085

Tyr Ala Glu Arg Thr Ala Lys Gly Asn Val Leu Glu Pro Gln Gly
    2090                2095                2100

Leu Ile Glu Ile Lys Phe Arg Ser Glu Glu Leu Lys Glu Cys Met
    2105                2110                2115

Gly Arg Leu Asp Pro Glu Leu Ile Asp Leu Lys Ala Arg Leu Gln
    2120                2125                2130

Gly Ala Asn Gly Ser Leu Ser Asp Gly Glu Ser Leu Gln Lys Ser
    2135                2140                2145

Ile Glu Ala Arg Lys Lys Gln Leu Leu Pro Leu Tyr Thr Gln Ile
    2150                2155                2160

Ala Val Arg Phe Ala Glu Leu His Asp Thr Ser Leu Arg Met Ala
    2165                2170                2175

Ala Lys Gly Val Ile Arg Lys Val Val Asp Trp Glu Asp Ser Arg
    2180                2185                2190

Ser Phe Phe Tyr Lys Arg Leu Arg Arg Arg Leu Ser Glu Asp Val
    2195                2200                2205

Leu Ala Lys Glu Ile Arg Gly Val Ile Gly Glu Lys Phe Pro His
    2210                2215                2220

Lys Ser Ala Ile Glu Leu Ile Lys Lys Trp Tyr Leu Ala Ser Glu
    2225                2230                2235

Ala Ala Ala Ala Gly Ser Thr Asp Trp Asp Asp Asp Asp Ala Phe
    2240                2245                2250

Val Ala Trp Arg Glu Asn Pro Glu Asn Tyr Lys Glu Tyr Ile Lys
    2255                2260                2265

Glu Leu Arg Ala Gln Arg Val Ser Arg Leu Leu Ser Asp Val Ala
    2270                2275                2280

Gly Ser Ser Ser Asp Leu Gln Ala Leu Pro Gln Gly Leu Ser Met
    2285                2290                2295

Leu Leu Asp Lys Met Asp Pro Ser Lys Arg Ala Gln Phe Ile Glu
    2300                2305                2310

Glu Val Met Lys Val Leu Lys
    2315                2320


<210> SEQ ID NO 17
<211> LENGTH: 93
<212> TYPE: DNA
<213> ORGANISM: Triticum aestivum

<400> SEQUENCE: 17

gtctgttcct cgtgctgggc aagtctggtt tccagattca gytactaaga cagcgccagg     60

caatgctgga cttcaaccgt gaaggattac ctc                                  93


<210> SEQ ID NO 18
<211> LENGTH: 85
<212> TYPE: PRT
<213> ORGANISM: Triticum aestivum
<220> FEATURE:
<221> NAME/KEY: misc_feature
<222> LOCATION: (42)..(42)
<223> OTHER INFORMATION: Xaa can be any naturally occurring amino acid
```

-continued

```
<400> SEQUENCE: 18

Gly Val Ile Ala Val Glu Thr Gln Thr Met Gln Leu Ile Pro Ala Asp
1               5                   10                  15

Pro Ala Asp Pro Gly Gln Leu Asp Ser His Glu Arg Ser Val Pro Arg
            20                  25                  30

Ala Gly Gln Val Trp Phe Pro Asp Ser Xaa Thr Lys Thr Ala Gln Ala
        35                  40                  45

Met Leu Asp Phe Asn Arg Glu Gly Leu Pro Leu Phe Ile Leu Ala Asn
    50                  55                  60

Trp Arg Gly Phe Ser Gly Gly Gln Arg Asp Leu Phe Glu Gly Ile Leu
65                  70                  75                  80

Gln Ala Gly Ser Thr
                85
```